(12) United States Patent
Spence

(10) Patent No.: US 11,432,884 B1
(45) Date of Patent: Sep. 6, 2022

(54) METHOD FOR DELIVERY OF PROSTHETIC AORTIC VALVE

(71) Applicant: HBX, Inc., Louisville, KY (US)

(72) Inventor: Paul A. Spence, Aventura, FL (US)

(73) Assignee: HBX, Inc., Louisville, KY (US)

( * ) Notice: Subject to any disclaimer, the term of this patent is extended or adjusted under 35 U.S.C. 154(b) by 0 days.

(21) Appl. No.: 17/547,588

(22) Filed: Dec. 10, 2021

Related U.S. Application Data

(63) Continuation of application No. 16/881,900, filed on May 22, 2020, which is a continuation of application
(Continued)

(51) Int. Cl.
*A61F 2/24* (2006.01)
*A61M 25/01* (2006.01)
(Continued)

(52) U.S. Cl.
CPC ............ *A61B 34/20* (2016.02); *A61F 2/2418* (2013.01); *A61F 2/2433* (2013.01);
(Continued)

(58) Field of Classification Search
CPC .... A61F 2/2418; A61F 2/2433; A61F 2/2436; A61F 2/24; A61B 2090/3762; A61B 2250/0098; A61M 25/0108
See application file for complete search history.

(56) References Cited

U.S. PATENT DOCUMENTS

| 5,554,179 A | 9/1996 | Stroetmann et al. |
| 7,374,571 B2 | 5/2008 | Pease et al. |
| (Continued) | | |

FOREIGN PATENT DOCUMENTS

WO     WO-2018026904 A1     2/2018

OTHER PUBLICATIONS

International Search Report and Written Opinion for International Application No. PCT/US2017/045070 dated Dec. 7, 2017, 9 pages.
(Continued)

*Primary Examiner* — Jocelin C Tanner

(57) ABSTRACT

Methods of delivering a prosthetic aortic heart valve are disclosed. The disclosed methods include loading a prosthetic aortic valve in a collapsed configuration into a delivery sheath so that a selected point on the prosthetic valve is rotationally aligned relative to a long axis of the delivery sheath with a selected radiopaque marker on the delivery sheath, while under fluoroscopic imaging, rotating the delivery sheath about its long axis to align a selected radiopaque marker on the delivery sheath with the selected point on the native aortic valve in a fluoroscopic imaging plane, thereby establishing a desired orientation of the prosthetic aortic valve with respect to the native aortic valve in which the prosthetic valve commissures are rotationally aligned with commissures of the native aortic valve, further advancing the delivery sheath along its long axis until the prosthetic aortic valve is disposed inside the native aortic valve, and deploying the prosthetic aortic valve into an implanted state inside the native aortic valve with the prosthetic aortic valve aligned in the desired orientation with respect to the native aortic valve.

11 Claims, 75 Drawing Sheets

Related U.S. Application Data

No. 15/873,932, filed on Jan. 18, 2018, now Pat. No. 10,722,352, which is a continuation of application No. PCT/US2017/045070, filed on Aug. 2, 2017.

(60) Provisional application No. 62/467,394, filed on Mar. 6, 2017, provisional application No. 62/445,420, filed on Jan. 12, 2017, provisional application No. 62/445,446, filed on Jan. 12, 2017, provisional application No. 62/411,153, filed on Oct. 21, 2016, provisional application No. 62/381,885, filed on Aug. 31, 2016, provisional application No. 62/370,435, filed on Aug. 3, 2016.

(51) Int. Cl.
 *A61B 90/00* (2016.01)
 *A61B 34/20* (2016.01)

(52) U.S. Cl.
 CPC .... *A61F 2/2436* (2013.01); *A61B 2090/3762* (2016.02); *A61F 2250/0098* (2013.01); *A61M 25/0108* (2013.01)

(56) References Cited

U.S. PATENT DOCUMENTS

| | | | |
|---|---|---|---|
| 8,475,522 B2* | 7/2013 | Jimenez | A61M 25/0147 623/2.11 |
| 9,579,197 B2 | 2/2017 | Duffy et al. | |
| 10,722,352 B2 | 7/2020 | Spence | |
| 2002/0143384 A1 | 10/2002 | Ozasa | |
| 2004/0162603 A1 | 8/2004 | Golds et al. | |
| 2004/0167619 A1 | 8/2004 | Case et al. | |
| 2005/0240200 A1 | 10/2005 | Bergheim | |
| 2006/0074485 A1 | 4/2006 | Realyvasquez | |
| 2008/0208314 A1 | 8/2008 | Skerven | |
| 2010/0036479 A1 | 2/2010 | Hill et al. | |
| 2010/0168839 A1 | 7/2010 | Braido et al. | |
| 2010/0172556 A1* | 7/2010 | Cohen | A61B 18/1492 600/407 |
| 2011/0251676 A1* | 10/2011 | Sweeney | A61F 2/2436 623/1.23 |
| 2012/0022633 A1 | 1/2012 | Olson et al. | |
| 2012/0041530 A1 | 2/2012 | Gaudiani | |
| 2012/0158129 A1 | 6/2012 | Duffy et al. | |
| 2013/0144373 A1 | 6/2013 | Shahriari | |
| 2013/0184812 A1 | 7/2013 | Cai et al. | |
| 2013/0274618 A1 | 10/2013 | Hou et al. | |
| 2014/0073978 A1 | 3/2014 | Shuros et al. | |
| 2014/0107763 A1 | 4/2014 | Layne et al. | |
| 2014/0142694 A1* | 5/2014 | Tabor | A61F 2/013 623/2.18 |
| 2014/0172080 A1 | 6/2014 | Bruchman et al. | |
| 2014/0172377 A1 | 6/2014 | Taubin et al. | |
| 2014/0276616 A1 | 9/2014 | Smith et al. | |
| 2014/0336744 A1* | 11/2014 | Tani | A61F 2/966 623/1.11 |
| 2014/0371841 A1 | 12/2014 | Casley et al. | |
| 2015/0209140 A1 | 7/2015 | Bell et al. | |
| 2016/0120643 A1 | 5/2016 | Kupumbati | |
| 2016/0354164 A1 | 12/2016 | Nichogi et al. | |
| 2017/0360558 A1 | 12/2017 | Ma | |
| 2018/0116843 A1 | 5/2018 | Schreck et al. | |
| 2018/0153690 A1* | 6/2018 | Spence | A61F 2/90 |
| 2018/0325666 A1 | 11/2018 | Ma | |
| 2020/0170812 A1* | 6/2020 | White | A61F 2/2427 |
| 2020/0281717 A1 | 9/2020 | Spence | |
| 2021/0186690 A1 | 6/2021 | Spence | |
| 2021/0220128 A1 | 7/2021 | Spence | |

OTHER PUBLICATIONS

Office Action for U.S. Appl. No. 16/881,900, dated Nov. 19, 2021, 19 pages.
Office Action for U.S. Appl. No. 17/224,793 dated Nov. 16, 2021, 15 pages.
Office Action for U.S. Appl. No. 15/873,932, dated Dec. 20, 2019, 9 pages.
Office Action for U.S. Appl. No. 17/195,207, dated Jun. 7, 2021, 18 pages.
Office Action for U.S. Appl. No. 17/195,207, dated Sep. 17, 2021, 15 pages.

* cited by examiner

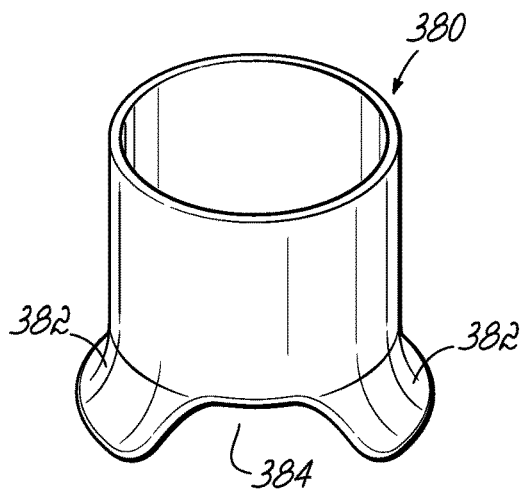
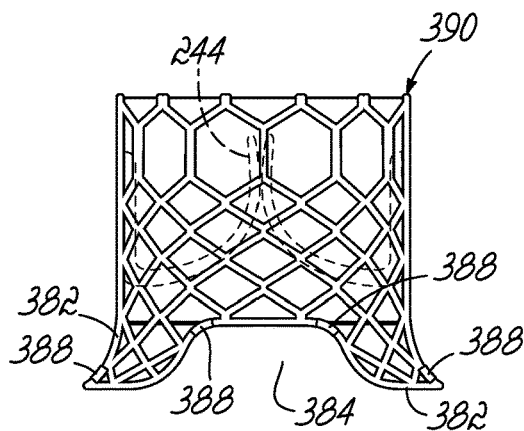
FIG. 29A  FIG. 29B
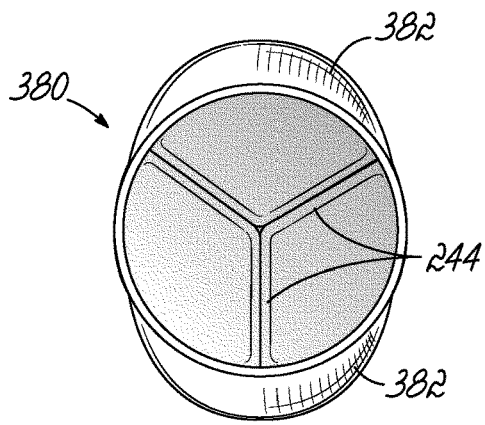
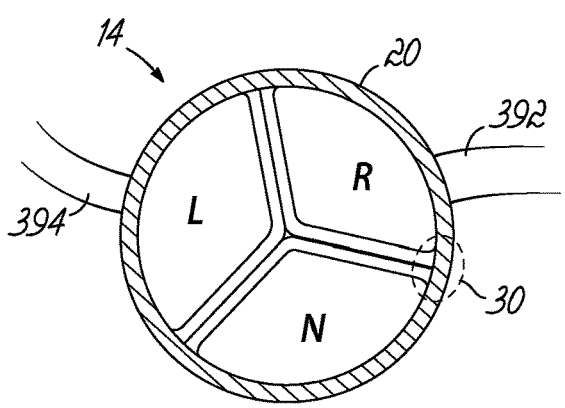
FIG. 29C  FIG. 30A
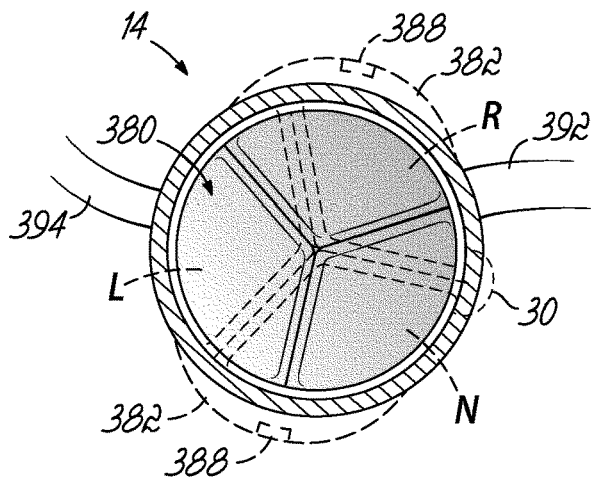
FIG. 30B

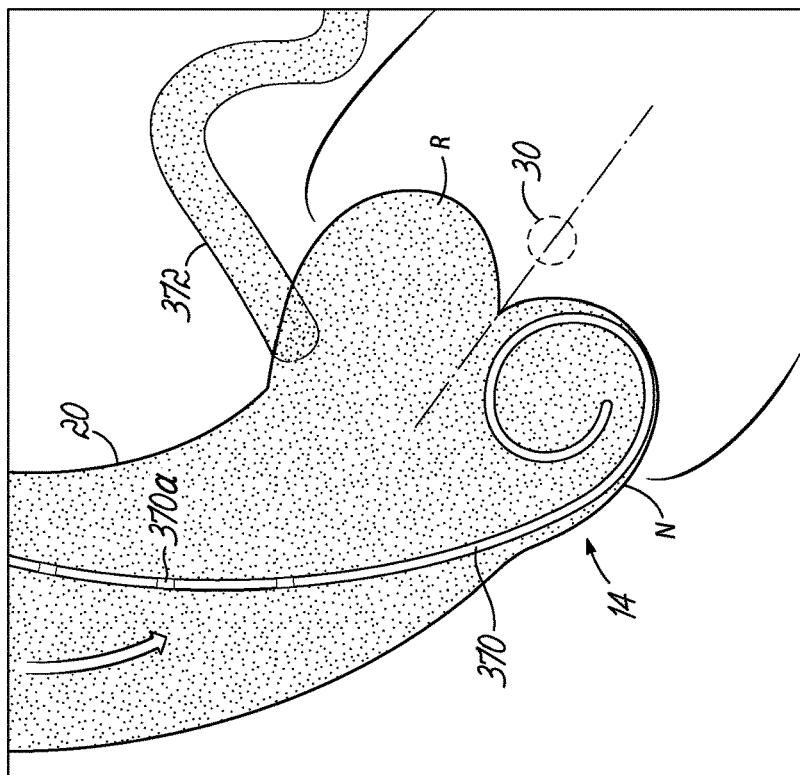
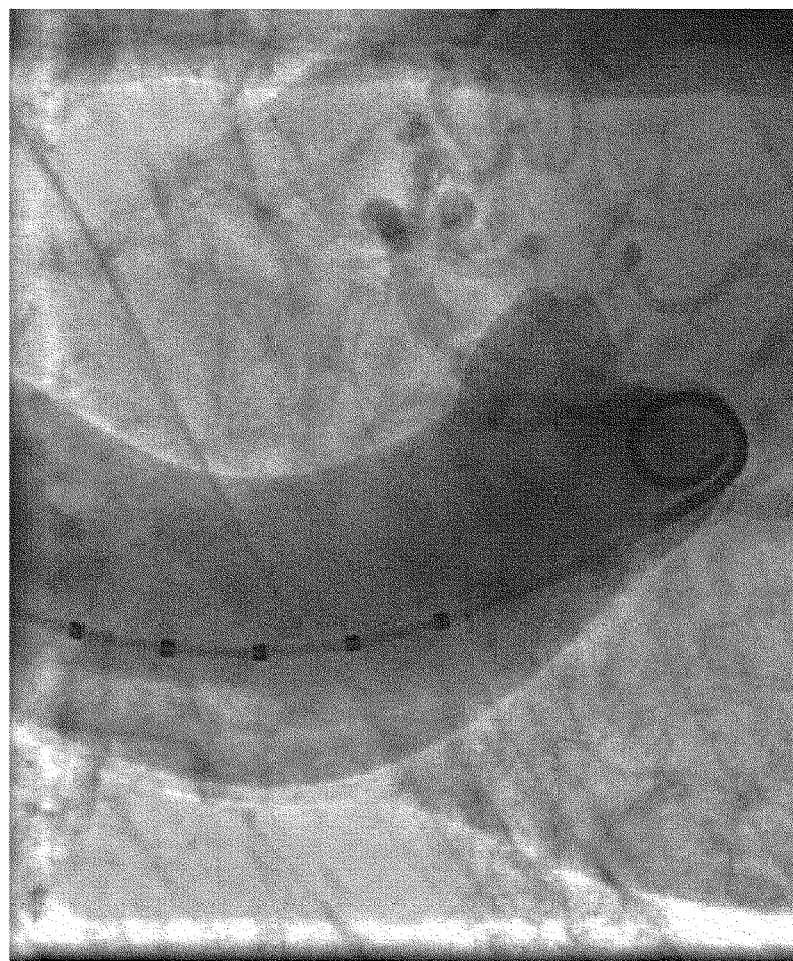
FIG. 31B-2
FIG. 31B-1

METHOD FOR DELIVERY OF PROSTHETIC AORTIC VALVE

CROSS REFERENCE TO RELATED APPLICATIONS

This application is a continuation of U.S. patent application Ser. No. 16/881,900, filed May 22, 2020, which is a continuation of U.S. patent application Ser. No. 15/873,932, filed Jan. 18, 2018, now U.S. Pat. No. 10,722,352, which is a continuation of PCT Application Serial No. PCT/US2017/045070, filed Aug. 2, 2017, which relates to and claims the priority of U.S. Provisional Patent Application Ser. No. 62/467,394 filed Mar. 6, 2017; U.S. Provisional Patent Application Ser. No. 62/445,446, filed Jan. 12, 2017; U.S. Provisional Patent Application Ser. No. 62/445,420, filed Jan. 12, 2017; U.S. Provisional Patent Application Ser. No. 62/411,153, filed Oct. 21, 2016; U.S. Provisional Patent Application Ser. No. 62/381,885, filed Aug. 31, 2016; and U.S. Provisional Patent Application Ser. No. 62/370,435, filed on Aug. 3, 2016, the disclosures of which are incorporated by reference herein in their entirety.

BACKGROUND

Aortic valve replacement has changed considerably in the last decade. Previously, valve replacement required a major procedure with cardiopulmonary bypass, stopping of the heart, excision of the diseased valve and then suture implantation of a valve prosthesis at the site of the excised valve. The procedure was often difficult for patients and some older patients were too ill to undergo surgery.

This all changed when it was found that the old diseased valve could be left in place and a prosthetic valve could be implanted inside the diseased valve using a catheter procedure. There was no need for cardiopulmonary bypass, no need to stop the heart and no need to suture a valve in position. In many countries the percutaneous procedure has become the most common and preferred way to treat patients.

The valve implant procedure involves using catheters to implant one of a variety of prostheses inside the old diseased valve. In general, the prosthetic valves use leaflets fashioned from tissue taken from pigs or cows. The leaflets sit inside mounting structures or frames. Common structures to support the leaflets include stents (self-expanding type stents such as used by Medtronic, balloon expanding stents such as used by Edwards, and a number of other companies), activatable frames (Sadra, Boston Scientific) and even inflatable frames (Direct Flow). To implant these devices, the leaflets are mounted on a frame, collapsed in catheters and then introduced inside the aorta of the patient. The valves are positioned inside the diseased native leaflets and then deployed and expanded to replace the function of the native aortic valve.

Development of this procedure has been complex and is a remarkable tribute to the doctors, engineers and companies who have overcome so many obstacles. There is one particularly vexing problem that still remains. A considerable number of patients develop complete heart block after the procedure. Complete heart block can occur immediately or it can be delayed days or weeks. The atrium sets the rate of contraction for the normal heart. The rate signal that originates in the atrium passes into the ventricles through specialized muscular conduction or conductive tissue at the top of the interventricular septum—just a short distance below the aortic valve. From the top of the septum, the signal passes to both ventricles and the ventricles contract and eject blood to the circulation. If the conduction tissue at the top of the ventricular septum is damaged, the signal does not pass and the ventricles do not receive the signal to contract. This condition is called heart block or complete heart block. The patient's heart may then stop completely, or it may contract at a very slow rate that is not consistent with survival. The patient may die suddenly or become very ill. This event can happen unexpectedly and there is a lingering risk for development of heart block for a prolonged period after percutaneous valve implantation.

Heart block has been seen with all of the prostheses used to date. It appears that the frame for the valve impacts against the conduction tissue and after a variable period of time damages the tissue and the tissue ceases to conduct the signal to contract to the ventricles. Heart block then occurs.

Heart block can result in sudden death or a hemodynamic crisis. The risk of heart block requires prolonged monitoring because of the unpredictable nature of the event. The treatment for heart block is implantation of a pacemaker. While this is a common and quite benign procedure, the effectiveness of the heart's contraction with a pacemaker never reproduces the contraction that results from a healthy native conduction system. And pacemakers are expensive and require lifelong surveillance necessitating visits by the patients to ensure their device is functioning properly and that the battery is still effective.

The rate of heart block that has been observed ranges from about 10% to as high as 30%. Despite the fact that almost a decade of work has been conducted, no valve and no procedure to date has been shown to eliminate the problem.

Considerable research has been conducted to understand this problem. Recently, interventional cardiologists have found that if the frame of the prosthetic valve sits less than 4 mm to 5 mm below the lowest point of the native valve, heart block almost never occurs. If the prosthesis sits lower than this the risk of heart block rises.

This makes good anatomic sense. Just beneath the aortic valve sits the membranous septum. The septum is a small region of non-muscular tissue that separates the two ventricles. It sits on the top of the interventricular septum. The conduction system that passes the signal to contract into the ventricle sits on the crest of the interventricular septum. The distance from the nadir of the aortic valve leaflets to the conduction tissue is approximately 4 mm. This corresponds exactly with the clinical observation by the interventional cardiologists.

The current trend is to make every effort possible to implant a prosthetic valve to ensure that its lowest point is positioned less than 4 mm below the nadir of the native aortic valve leaflets. This is no easy feat since the valves are introduced on long catheters passing from an entry point in the groin, up the aorta, around the aortic arch and then into the ventricle. The heart is beating and ejecting blood, and this makes accurate positioning difficult as well. It is extremely difficult to be sure that a valve will be deployed in the perfect position. The person performing the procedure is also concerned that if the valve sits too high, it may not engage inside the native leaflets and it may be ejected out of the correct position into the aorta.

It would be very useful to have devices, systems and methods to help the interventionist to place a prosthetic valve in the ideal position and/or otherwise reliably prevent damage to the conductive tissue. A goal should be to prevent force from being applied to the conductive tissue after implantation. And the prosthetic valve must not sit so high that it does not engage securely against the native leaflets and eject out of the correct position.

SUMMARY

In a first general embodiment, the invention provides a prosthetic aortic valve for mounting at an implant site associated with the native aortic valve of a patient. The prosthetic aortic valve comprises a stent frame formed from wire. The stent frame includes an upper margin or edge, a lower margin or edge, and an interior. The stent frame includes only a single cut-out, opening or recess along the lower margin or edge configured to align with conduction tissue below the native aortic valve to prevent contact by any structural element of the stent frame with the conduction tissue. The prosthetic aortic valve further includes a plurality of prosthetic valve leaflets mounted within the interior of the stent frame to provide unidirectional flow of blood through the prosthetic aortic valve. The provision of only a single cut-out, opening or recess helps maximize the amount of material of the prosthetic aortic valve that assists with sealing against native heart tissue, while providing for no engagement or contact between any structural element of the stent frame with the conduction tissue that would otherwise promote the undesired condition of heart block. This provides the dual benefit of adequate sealing, while preventing disruption of signals that could lead to complete heart block.

The cut-out, opening or recess may be generally U-shaped, V-shaped or generally square shaped, although other configurations or shapes are possible as well, such as circular or other rounded shapes. The cut-out, opening or recess could further comprise an indentation in the stent frame so that the frame avoids compression and contact with the conduction tissue at the location of the indentation. The prosthetic valve may further comprise a covering material, such as a fabric or mesh material, or other type of material, attached over the cut-out, opening or recess. One or more radiopaque markers may be placed adjacent opposite edges of the cut-out, opening or recess to aid in the correct orientation of the valve during implantation in relationship to the conduction tissue, i.e., for avoiding any negative contact or engagement with the conduction tissue that might lead to complete heart block. For example, the marker(s) may comprise a continuous marker outlining the cut-out, opening or recess, or discrete markers on opposite sides of the cut-out, opening or recess.

In another general embodiment, the invention provides a prosthetic aortic valve for mounting at an implant site associated with the native aortic valve of a patient, comprising a stent frame formed from wire. The stent frame includes an upper margin or edge, a lower margin or edge, and an interior. The stent frame includes a plurality of spaced apart cut-outs, openings or recesses located along the lower margin or edge. One of the cut-outs, openings or recesses may be aligned with the conduction tissue located below the native aortic valve annulus to prevent contact by any structural element of the stent frame with the conduction tissue. Prosthetic valve leaflets are mounted within the interior of the stent frame to provide unidirectional flow of blood through the prosthetic aortic valve. A covering material is fixed on the outside surface of the stent frame to enclose the interior, but the covering material includes a plurality of cut-outs respectively aligned with the plurality of cut-outs, openings or recesses in the stent frame. In this manner, one of the cut-outs in the covering material are designed to align with the conduction tissue depending on the rotational orientation of the prosthetic aortic valve when implanted, and the lack of contact between the covering material and the conduction tissue will further minimize the occurrences or chances of complete heart block.

In another embodiment or aspect of the invention, a method of implanting a prosthetic aortic valve is provided, with the prosthetic aortic valve taking on a construction such as one of the constructions described herein. The method generally comprises inserting the prosthetic valve into a native aortic valve, and aligning a cut-out, opening or recess in the prosthetic valve with the conduction tissue located below the native aortic annulus. The method may further comprise placing the prosthetic valve, in a collapsed condition, into a delivery sheath in a femoral artery of the patient and the prosthetic aortic valve in a predetermined rotational orientation for ensuring that the cut-out, opening or recess is at least substantially aligned with the conduction tissue at the native aortic valve. The method may further comprise using at least one radiopaque marker placed on the prosthetic aortic valve adjacent opposite edges of the cut-out, opening or recess to align the cut-out, opening or recess with the conduction tissue.

In another embodiment of the invention, a system is provided to assist percutaneous aortic valve replacement. The system generally comprises a prosthetic aortic valve movable between a collapsed condition suitable for percutaneous delivery into a native aortic valve and an expanded condition within the native aortic valve. The system further includes a guide device configured to engage native heart tissue and guiding valve deployment and expansion away from the conduction tissue of the heart. The system may further involve integrating the guide device with the prosthetic aortic valve. In another aspect, the guide device is comprised of wire and takes on the form of at least one of: a helix, a basket, and a plurality of radiating arms.

In another embodiment or aspect, the invention provides a method of implanting a prosthetic aortic valve, comprising using a guide device to identify the nadir of the aortic valve leaflets or the left ventricular outflow tissue, and percutaneously implanting a prosthetic aortic valve having a valve frame so that no portion of the valve frame contacts conduction tissue located below the native aortic annulus. The method may further comprise removing the guide device from the patient through a catheter after implanting the prosthetic aortic valve, and avoiding trapping the guide device with the expanding prosthetic valve. The method may also or alternatively comprise using at least one radiopaque marker on the guide device and the prosthetic aortic valve to locate the prosthetic aortic valve relative to the guide device at the native aortic valve. The method may additionally involve using the guide device, or a separate centering guide, to center the placement of the prosthetic aortic valve within the native aortic valve during implantation.

Various other embodiments, aspects, features and attendant advantages will become apparent upon review of the following more detailed description of the illustrative versions of devices, systems and methods constructed consistent with the inventive concepts.

BRIEF DESCRIPTION OF THE DRAWINGS

FIG. 28A-1 is a photographic image of a native aortic valve.

FIG. 28A-2 is a drawing of the image shown in FIG. 28A-1.

FIG. 29A is a perspective view of a prosthetic, expandable stent valve similar to the valve shown in FIG. 28D and including a fabric or other type of covering.

FIG. 29B is an elevational view of the valve shown in FIG. 29A, but with the covering removed.

FIG. 29C is a top view of the prosthetic valve shown in FIG. 29A.

FIG. 30A is a top view of the native aortic anatomy.

FIG. 30B is a top view schematically illustrating the valve of FIG. 29C inserted into the anatomy shown in FIG. 30A.

FIGS. 31A-1 and 31A-2 are respective views similar to those of FIGS. 28A-1 and 28A-2.

FIG. 31B-1 is a photographic image showing the native aortic valve and aorta from an angle illustrating the non and right coronary cusps.

FIG. 31B-2 is a drawing illustrating the features shown in the image of FIG. 31B-1.

FIG. 33A-1 is a photographic image illustrating the native aortic valve and adjacent anatomy or components.

FIG. 33A-2 is a drawing illustrating the features shown in the photographic image of FIG. 33A-1, and illustrating the initial implantation of an expandable stent valve within the native aortic valve.

DETAILED DESCRIPTION

Figure 1:
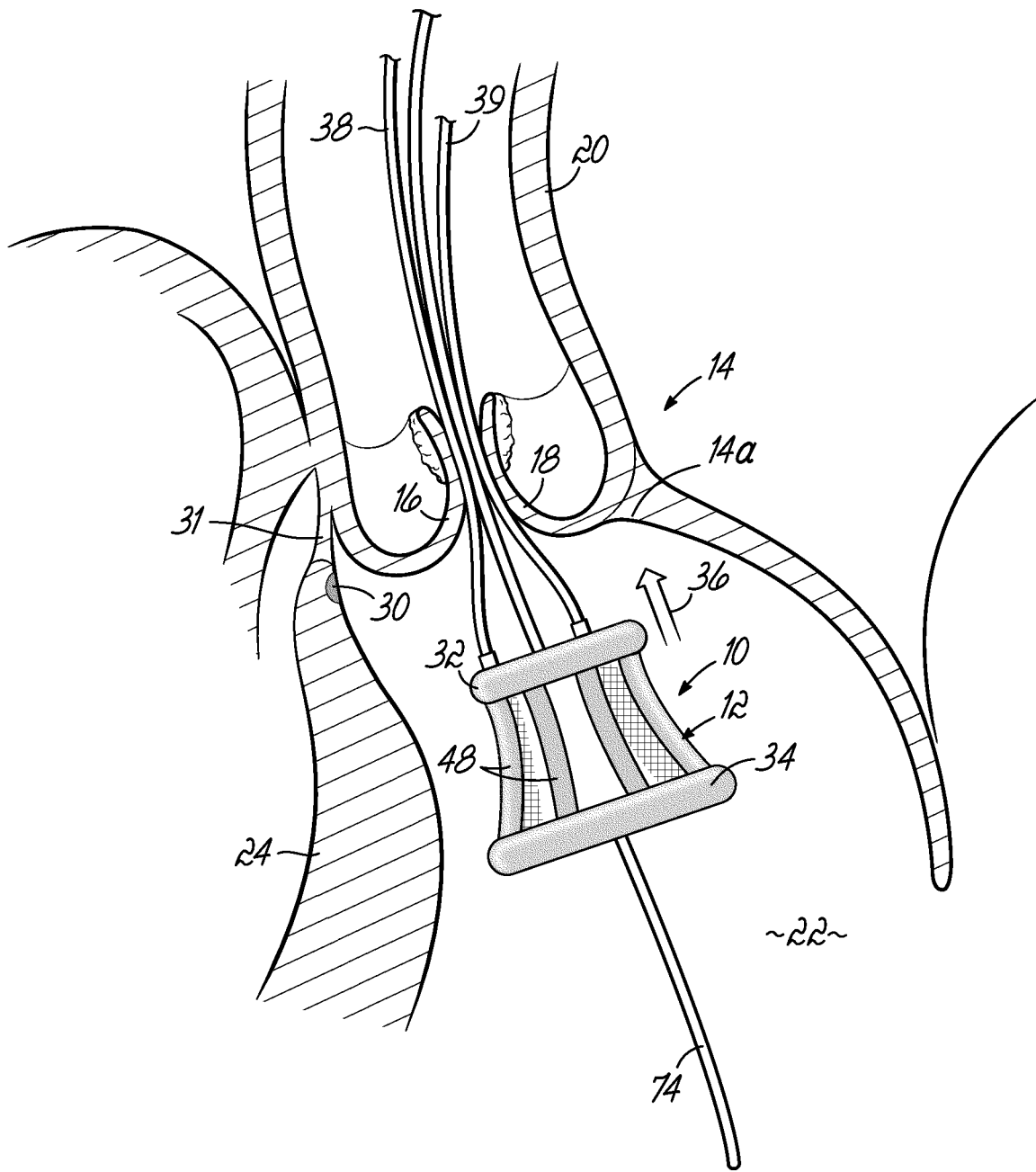
FIG. 1 is a perspective view illustrating an inflatable prosthetic aortic valve being inserted into a native aortic valve in accordance with a prior art method.

In this description, like reference numerals refer to like structure. Such structure may have different forms, as will be apparent from the description and/or drawings, but the same or analogous function. In later figures, description of repetitious subject matter or elements with the same reference numbers as earlier described is avoided for conciseness. Any of the features, uses, components or other aspects of an embodiment may be combined with any other embodiment.

FIG. 1 shows the implant of a percutaneous, prosthetic aortic valve 10 of the prior art that is supported by an inflatable frame 12. The figure shows a diseased native aortic valve 14 with stiff and thickened leaflets 16, 18. The aorta 20 sits above the valve 14. Below the valve 14 is the inside of the left ventricle 22. Beneath the valve 14 one side the anterior leaflet 16 of the aortic valve 14 is shown. On the other side is the interventricular septum 24. The conduction tissue 30 is identified by a small region located just below the valve leaflets 16, 18. The conduction tissue 30 sits on the crest of the muscular interventricular septum 24. The tissue above the conduction tissue 30 is the membranous septum 31. This is not muscular tissue.

The inflatable prosthetic valve 10 is introduced into the circulation in a collapsed state through introducers often at the groin of the patient. The collapsed valve and its delivery system are then passed up the aorta, through the disease aortic valve 14 and into the left ventricle 22. The valve 10 is then partially inflated for full deployment. It is particularly useful to inflate the upper circular element 32 of the support frame less and the lower element 34 of the support frame more as shown in this figure. This arrangement allows the interventionist to pull the valve prosthesis 10 inside the diseased leaflets 16, 18. The arrow 36 indicates the planned direction of pull.

Small narrow catheters 38, 39 are shown that are attached to the inflatable frame of the prosthesis 10 to inject fluids to inflate and expand the support structures.

Figure 2:
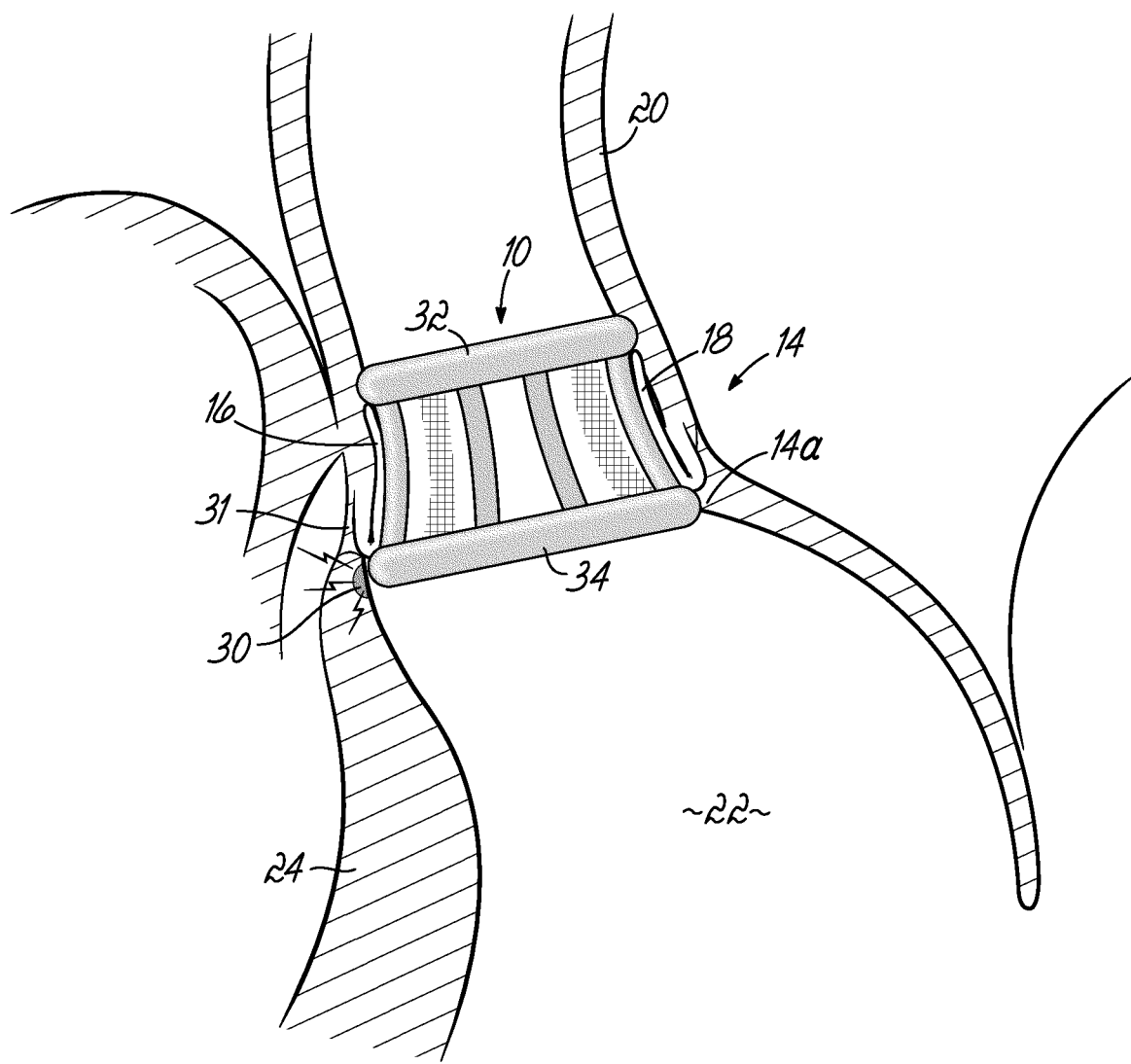
FIG. 2 is a perspective view, partially cross sectioned and schematic illustrating the prosthetic valve of FIG. 1 implanted and engaging conduction tissue in a manner that may promote heart block.

As shown in FIG. 2, the valve 10 has been pulled up into its final position. The lower element 34 of the valve frame, being inflated more, acts as a "stopper" and positions the valve 10 inside the diseased native leaflets 16, 18. The upper element 32 and the rest of the frame is then fully inflated.

FIG. 2 also shows why heart block is common. The lowest circular frame support 34 impinges against the conduction tissue 30 (shown by the irregular lines surrounding the conduction tissue 30). After an unpredictable period of time the conduction tissue 30 becomes damaged and it ceases to conduct the signal to contract. Heart block then results.

Figure 3A:
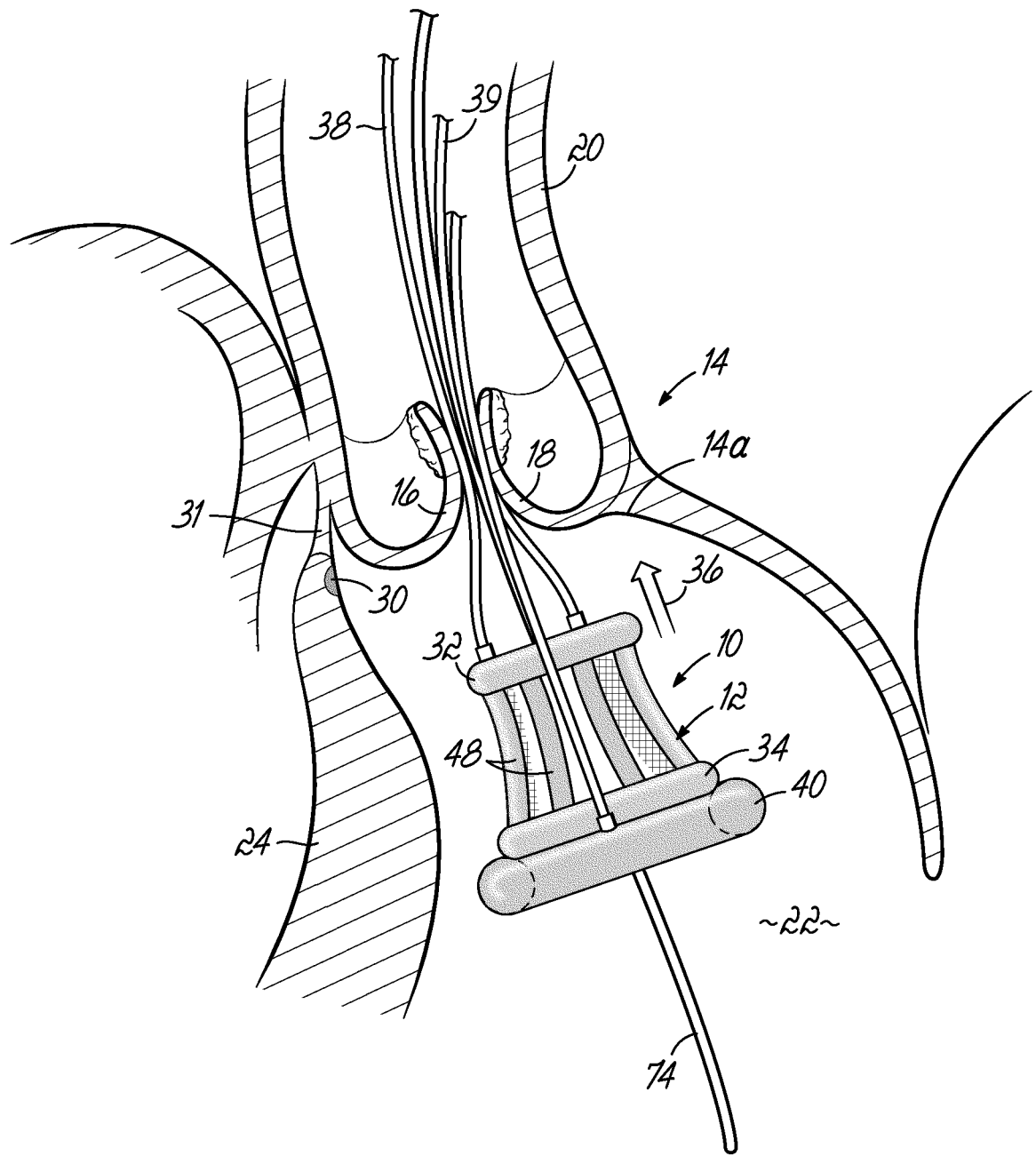
FIG. 3A is a perspective view, partially cross sectioned and schematic illustrating a guide device used in conjunction with the system and prosthetic valve shown in FIGS. 1 and 2 for preventing engagement between the prosthetic valve and the conduction tissue.

FIG. 3A illustrates a device, system and method in accordance with an exemplary embodiment of the invention to avoid the development of heart block. The same inflatable prosthesis 10 is shown as in the prior two figures. What is added is an additional item, i.e., an inflatable balloon guide or locator device 40. Although this guide or locator device 40 is an inflatable device, it will be understood that this is just an illustrative example and other types of locator devices may be used instead. For example, as will be further illustrated and discussed herein, various mechanical locator devices may be utilized instead. In this example, the locator device or guide 40 is an additional balloon that sits under the prosthesis 10. It is used only during the implant procedure and is removed or otherwise deactivated after the procedure so as not to negatively affect the heart. The inflatable balloon guide 40 has a separate inflation catheter 42 shown in the figure. The balloon can be inflated with air or fluid (with or without contrast material to identify it on fluoroscopy). The balloon 40 can be constructed from any typical plastic material that is used for medical devices. It can also have radiopaque markers to help visualize it on fluoroscopy.

The implant procedure is similar to what has been described previously. The inflatable frame for the valve is directed into the left ventricle 22 and then partially expanded. The guiding balloon 40 is expanded. The balloon guide 40 is linked to the valve prosthesis 10.

The balloon guide 40 is pulled back until it engages against the under surface of the left ventricle 22 (the left ventricular surface) of the lowest point of the diseased native aortic valve leaflets 16, 18 (the nadir of the leaflets 16, 18). The leaflets 16, 18 are typically sclerotic and often calcified and will reliably produce a resistance when the balloon guide 40 is pulled back toward the leaflets 16, 18.

Figure 3B:
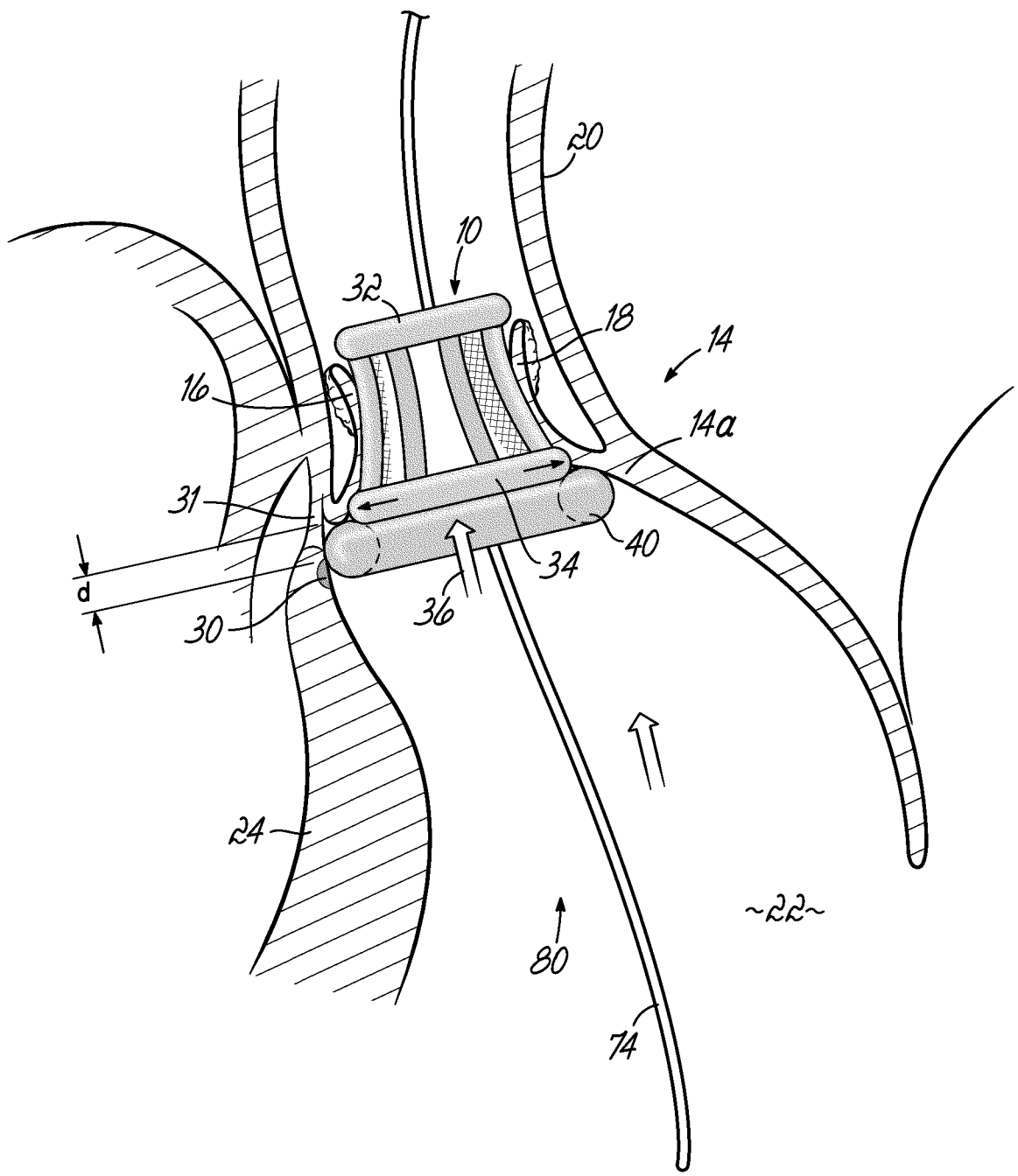
FIG. 3B is an illustration similar to FIG. 3A, but illustrating the prosthetic valve implanted at the native aortic valve with the guide device, e.g., guide balloon also in place.

As shown in FIG. 3B, the balloon guide 40 has been pulled upwards toward the diseased valve 14 until it stops under the diseased valve leaflets 16, 18. The balloon guide 40 will be engaged by the leaflets 16, 18.

The left ventricular outflow narrows under the aortic valve 14. The balloon guide 40 can also be engaged against the left ventricular outflow.

A sounding device (i.e., the locator device or guide) 40 could also engage against both the narrowing left ventricular outflow and the underside of the leaflets 16, 18.

The inflatable valve prosthesis 10 is now ready to be expanded. The diseased aortic valve leaflets 16, 18 are pushed aside and they engage against the frame of the prosthesis 10 to hold it in place.

FIG. 3B shows that the prosthesis 10 now sits at a slightly higher position than in the previous figures (FIGS. 1 and 2) where the balloon guide 40 was not used.

The lowest circular frame element 34 sits well above the conduction tissue 30.

After the implant, the balloon guide 40 is deflated and removed. Only the valve prosthesis 10 is left in place.

FIG. 3B schematically indicates that the conduction tissue 30 is approximately 4 mm below the native leaflets 16, 18, as shown by distance "d".

Figure 3C:
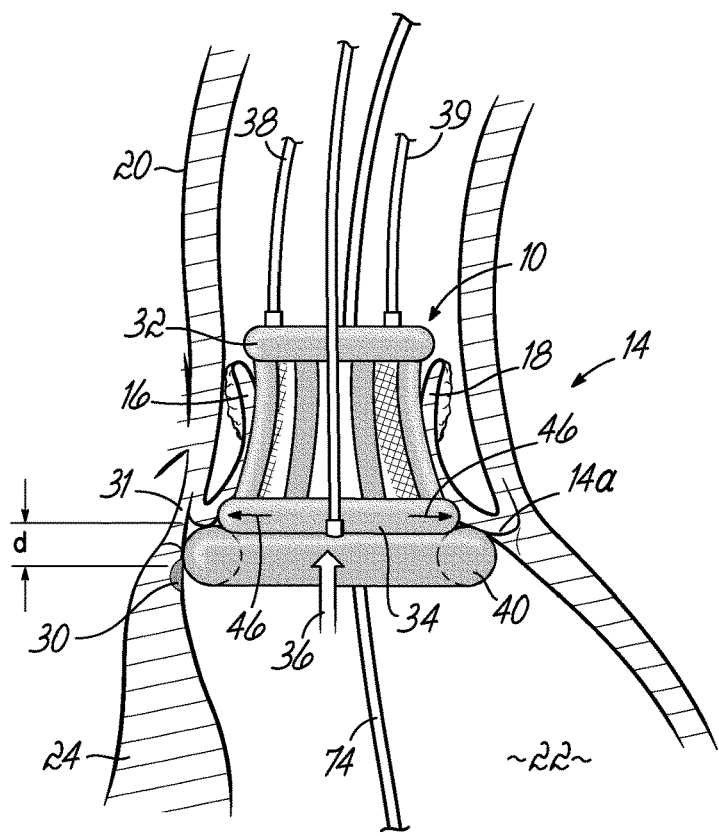
FIGS. 3C and 3D are respective illustrations similar to FIG. 3B, but illustrating further inflation of the inflatable valve and the inflatable balloon guide device.

FIG. 3C shows the prosthesis 10 with attached inflation catheters 38, 39 sitting in an ideal position well above the conduction tissue 30.

An arrow 46 shows the lowest element 34 of the frame being inflated and expanded inside the diseased leaflets 16, 18.

Figure 3D:
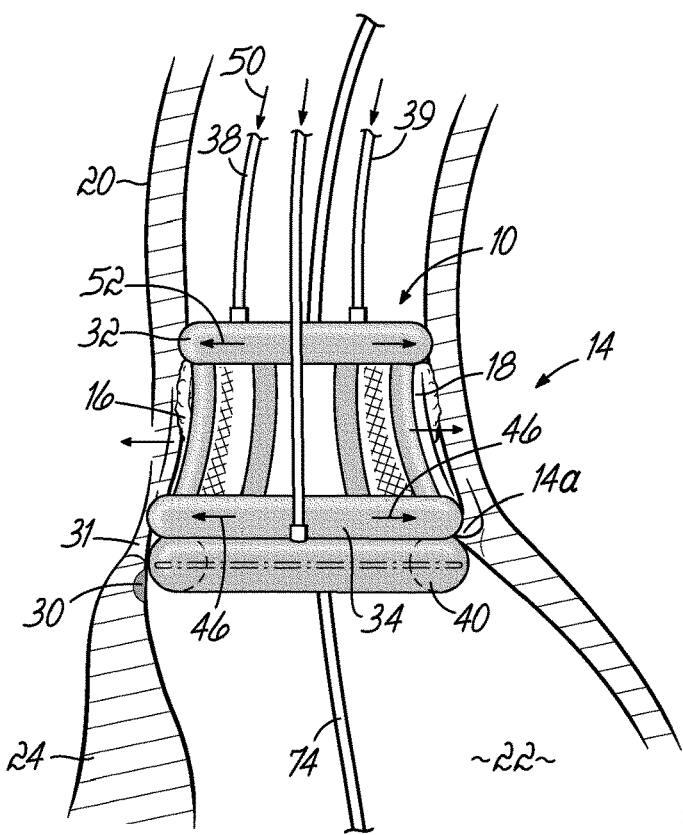

FIG. 3D shows the upper element 32 and the vertical support members 48 of the prosthesis 10 being expanded. Arrows 50 on the inflation catheters 38, 39, 42 show the direction of flow of the filling material.

Additional arrows 52 show the prosthetic valve 10 expanding into the diseased native leaflets 16, 18.

Figure 3E:
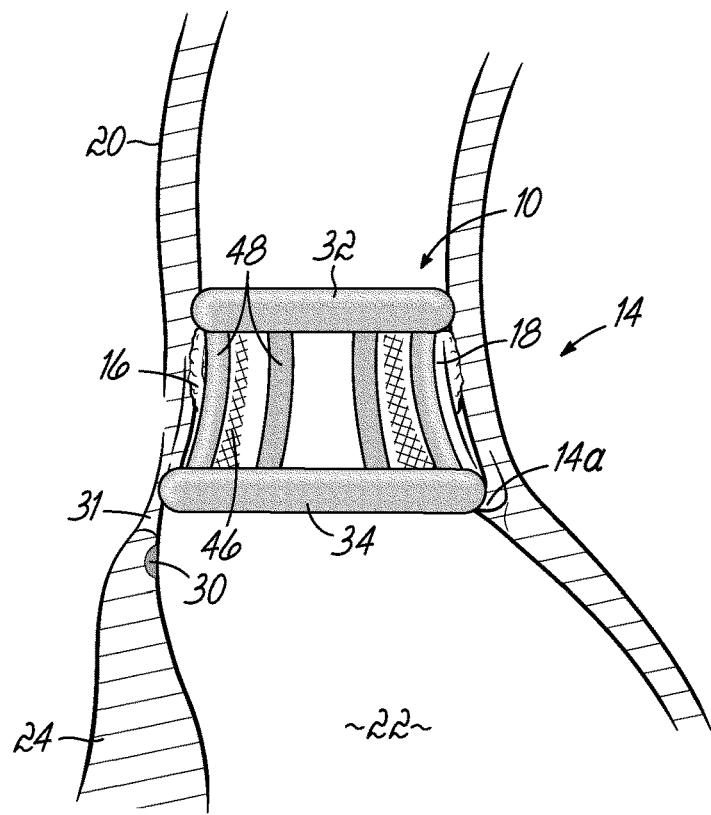
FIG. 3E is an illustration similar to FIG. 3D, but showing the fully implanted inflatable valve prosthesis out of engagement with the conduction tissue.

FIG. 3E shows the final implant location. Both the upper and lower circular supports 32, 34 as well as the vertical supports 48 are expanded. The balloon guide 40 has been removed. The valve 10 does not contact the conduction tissue 30.

Figure 3F:
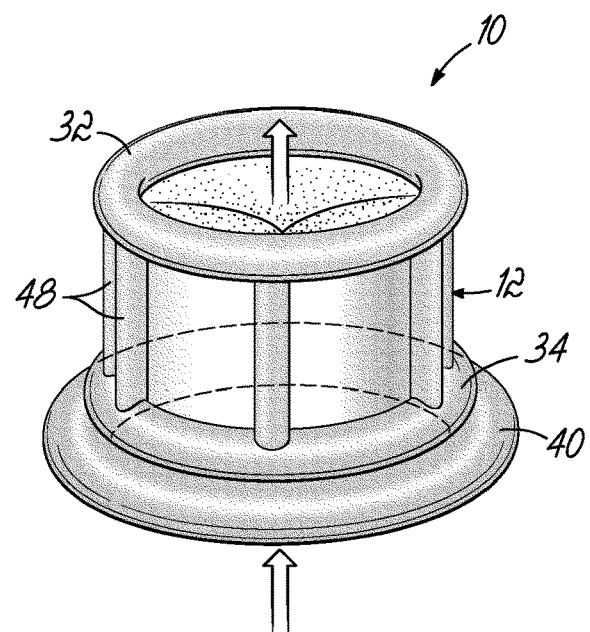
FIG. 3F is a perspective view illustrating the inflatable valve prosthesis and inflatable guide device in isolation from the anatomy.

FIG. 3F shows the temporary guide balloon 40 with the valve prosthesis 10. In this figure the temporary guiding balloon 40 is very close or touching the lowest circular inflatable member 34. There could also be a gap between the temporary inflatable balloon 40 and the valve prosthesis 10. It is also possible to have an overlap between any adjacent balloons. These constructions will help establish the ideal final position (higher or lower) of the prosthesis 10 inside the native aortic valve 14.

The inflatable guide 40 is shown here as a "doughnut" shaped structure. It could be a sphere or disc, but this would block the ejection of the blood out of the left ventricle 22. Any balloon guide shape that allows the guide to set a reliable position relative to the aortic valve leaflets 16, 18 and left ventricular outflow path can be used. For example, a cylinder or a tapered cylinder could be used. The cylinder would allow blood to flow through the native aortic valve 14 during the procedure.

These figures have shown a temporary guide 40 that is used to find the ideal position for the valve 10 and that is removed at the end of the procedure. It is also possible to integrate this delivery concept with the prosthesis design. For example, there could be two lower circular support rings in the valve prosthesis 10. The lowest one could be inflated to guide the position of the valve 10. The circular ring or element just above the lowest ring could then be inflated inside the diseased valve 14. The lowest ring could be deflated partially or completely so that it does not contact conducting tissue 30. Although it seems more reasonable at this time to have a temporary and separate balloon guide, it may prove easier to construct the devices or implant the devices in an integrated format.

Figure 4A:
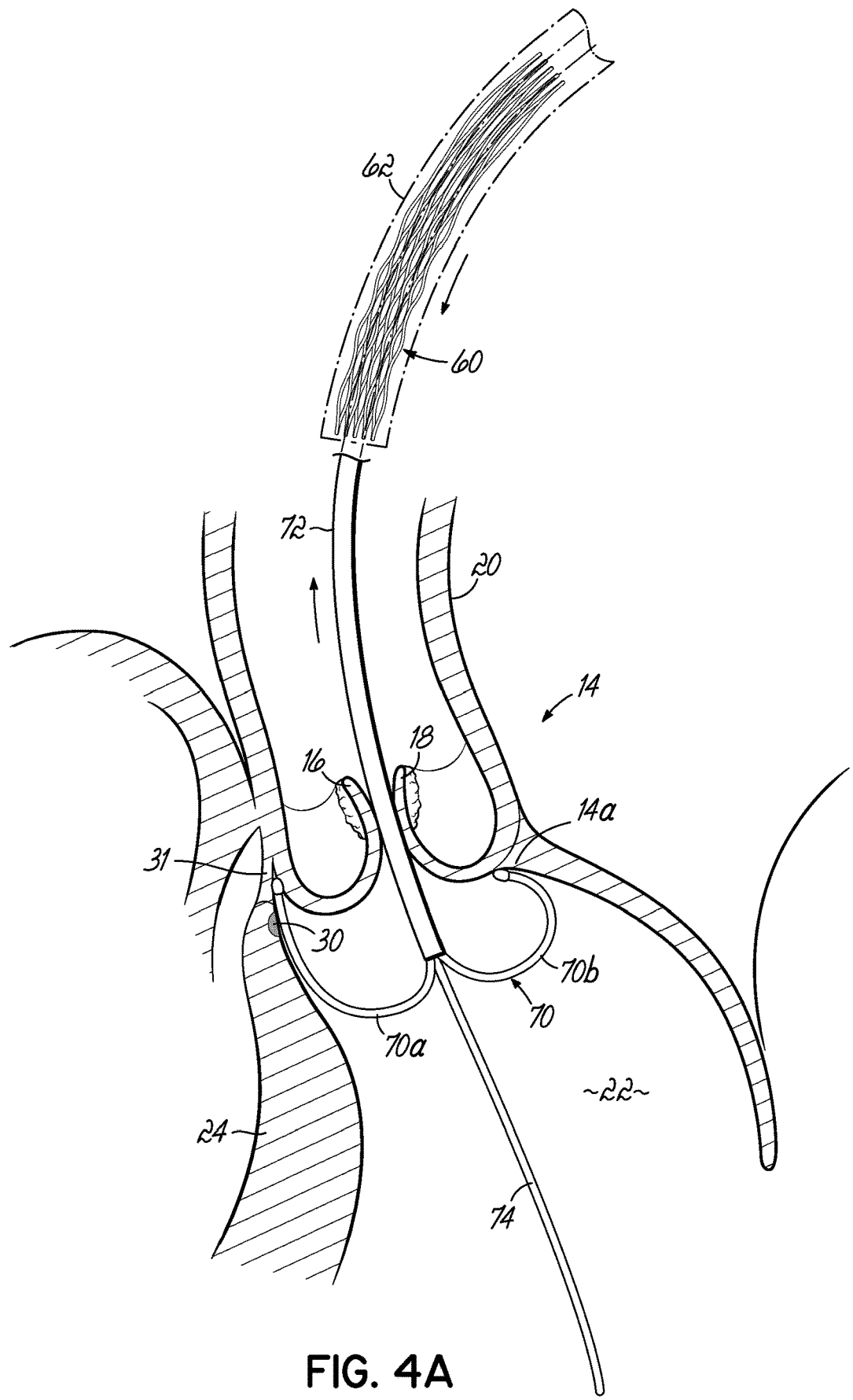
FIG. 4A is a schematic view with the anatomy again cross sectioned to illustrate the implantation of a self-expanding stent valve, in conjunction with another embodiment of a guide device for ensuring that the stent valve does not engage or contact the conduction tissue in a negative manner.

FIG. 4A shows a self-expanding aortic prosthesis 60 compressed inside a sheath or catheter 62. The prosthesis 60 is located in the aorta 20 and ready to be passed into the correct position inside the diseased and thickened leaflets 16, 18 for deployment.

A different guiding or locator device 70 is shown here. There is a catheter 72 passing into the left ventricle 22. The catheter 72 has a guide wire 74 in it passing toward the apex of the left ventricle 22.

Also passing through the catheter 72 is the locating or guiding device 70. This device 70 is not a balloon. A series of curved arms 70a, 70b are straightened and passed through the catheter 72 into the left ventricle 22. Once inside the left ventricle 22, the arms 70a, 70b spring into their preformed curved shape. The arms 70a, 70b of the sounding or guiding device 70 are then pulled back until it engages against the underside of the diseased aortic leaflets 16, 18. The operator will feel the arms 70a, 70b pulling against the leaflets 16, 18 and know that the tips of the arms 70a, 70b are now just underneath the aortic leaflets 16, 18. Also, using fluoroscopy, the operator will be able to see the arms 70a, 70b begin to buckle or bend as they are engaged under the leaflets 16, 18.

The sounding or locator device 70 could be made with shape memory material such as Nitinol so that it can be straightened for insertion and then assume its functioning shape. As Nitinol is sometime hard to see on fluoroscopy, radiopaque markers (such as gold), could be added. Or the Nitinol could be mixed with a radiopaque material for easy identification on fluoroscopy during the procedure.

Figure 4B:
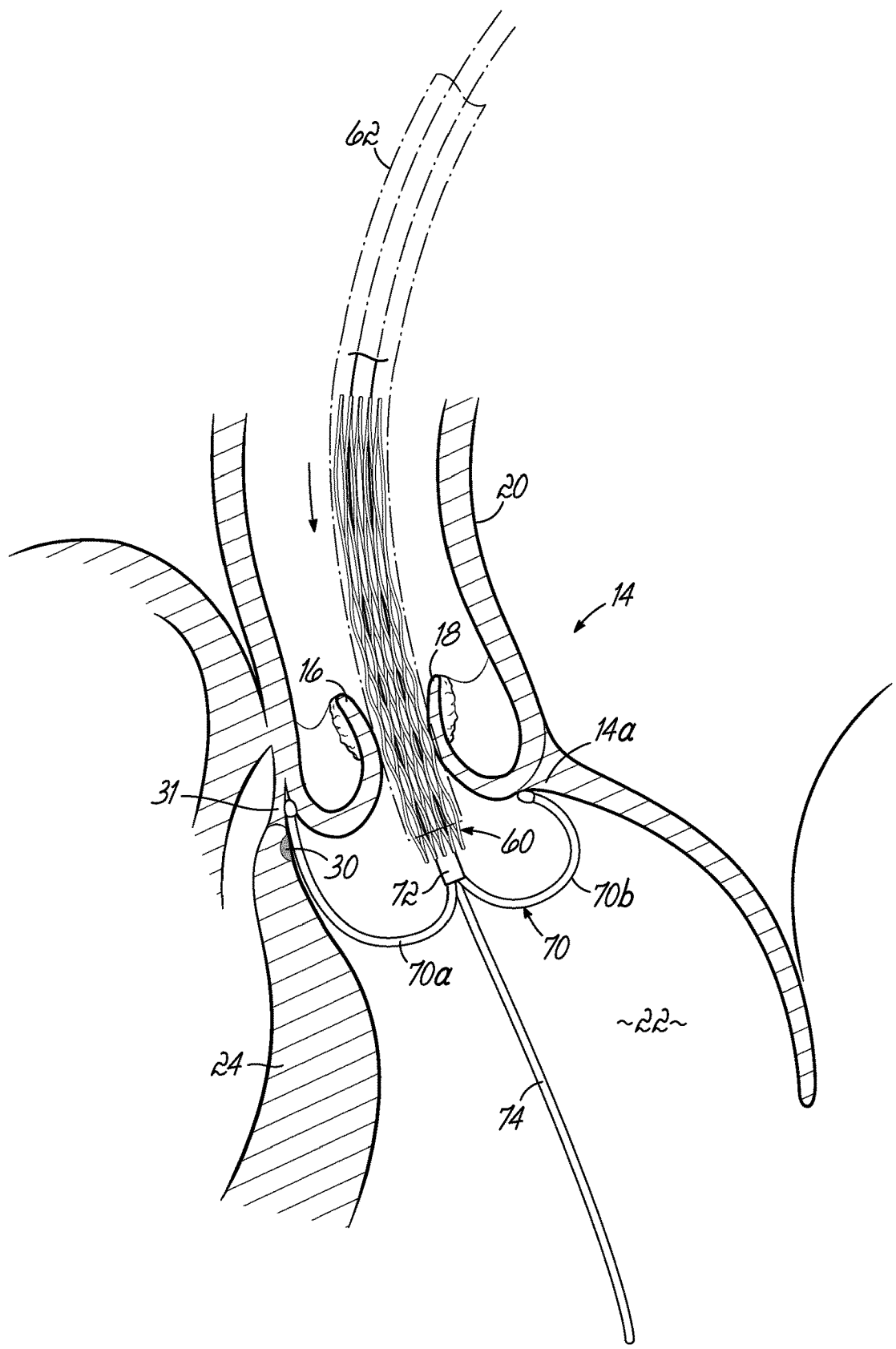
FIG. 4B is an illustration similar to FIG. 4A, but illustrating a further point in the method during which the self-expanding stent valve and its delivery system are inserted through the native aortic valve.

As shown in FIG. 4B, the sheath 62 holding the self-expanding stent valve 60 inside is advanced so that its tip is in the left ventricle 22 and the end of the catheter 62 is "stopped" in the correct position by the sounding or guiding device 70. As explained, the stop point can be identified by tactile feedback and visually from fluoscopy or other image guidance.

It is important to note that the guiding or locator device 70 is keeping the implant of the prosthesis 60 away from the conduction tissue 30. It will identify the lowest safe location that the interventionist can release the implant 70 once the system is fully implanted.

The relative positions of the catheter 62 that delivers the valve 60 and the guiding device 70 could be fixed by the manufacturer. The stent of a prosthetic valve 60 is lengthened when it is loaded inside the catheter 62. The prosthetic valve 60 shortens as the sheath 62 is withdrawn. A careful study of the amount of shortening would be necessary to set the distance between the "stop" point on the guide or sounding device 70 and the end of the sheath 62 that contains the valve prosthesis 60 to ensure the valve 60 deploys correctly.

Figure 4C:
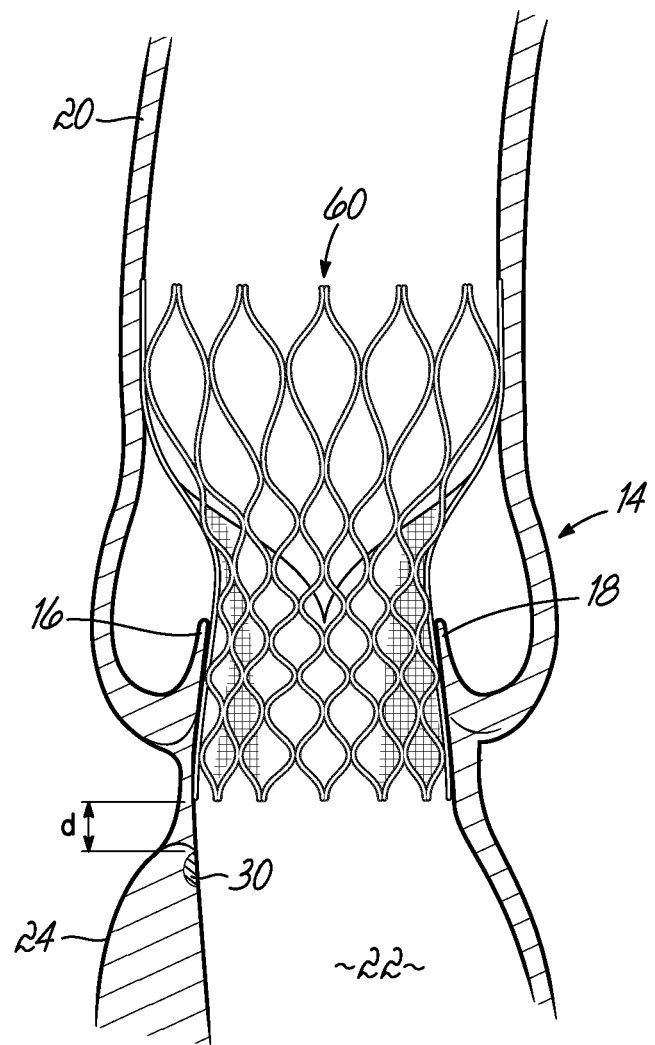
FIG. 4C is a schematic cross sectional view illustrating the fully implanted self-expanding stent valve, again out of negative contact or engagement with the conduction tissue.

FIG. 4C shows the implanted device 60. The retaining sheath 62 has been fully removed. The prosthetic valve 60 is fully deployed and engaged against the diseased native leaflets 16, 18.

Most importantly, the small circle of conduction tissue 30 at the top of the septum 24 is not contacted by the frame of the valve 60. A distance "d" separates the lowest part of the stent 60 from the conduction tissue 30.

Figure 5A:
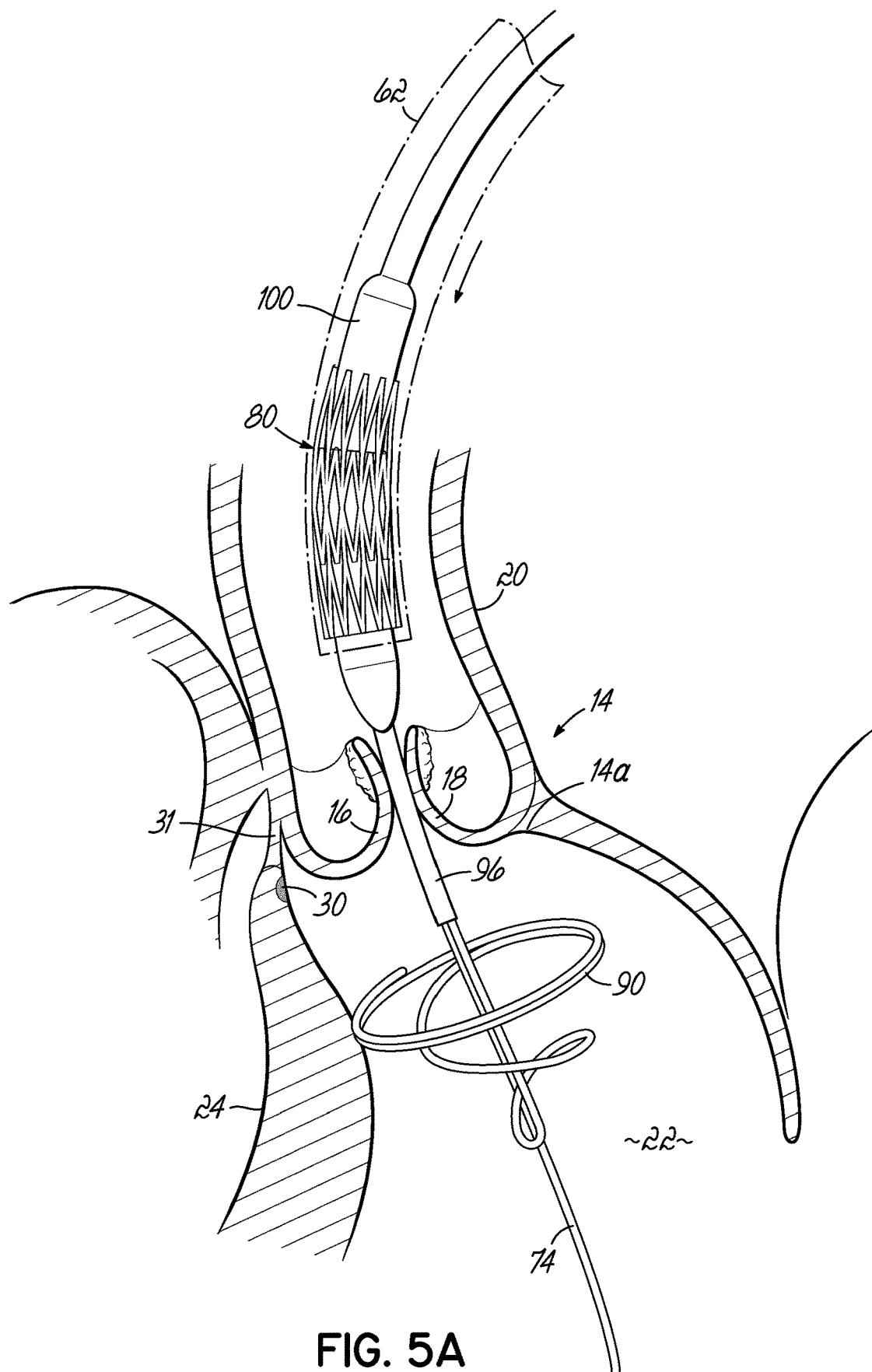
FIG. 5A is an illustration similar to FIG. 4A, but illustrating another alternative, or additional embodiment of a locating or guide device positioned in the left ventricle.

FIG. 5A shows another type of prosthesis 80 being delivered. This prosthesis 80 is a balloon expandable stented valve. The stent valve 80 is typically made from stainless steel alloys.

The prosthesis 80 has been introduced into the aorta 20 and is about to be guided into position inside the diseased leaflets 16, 18.

Inside the left ventricle 22 is a guide wire 82 which is passed toward the apex of the ventricle 22.

There is also another variation of a locator or sounding device 90. This device 90 is shown as a helical wire. The wire 90 can typically be composed of Nitinol. The Nitinol can be straightened for delivery inside a catheter 96 that may also carry the guide wire 82. The helix 90 will form inside the ventricle 22 as the Nitinol locator device 90 is extruded out of the catheter 96. The turns or coils of the helix 90 can be fabricated with a gap. A larger or smaller gap may be desirable in a clinical procedure.

Figure 5B:
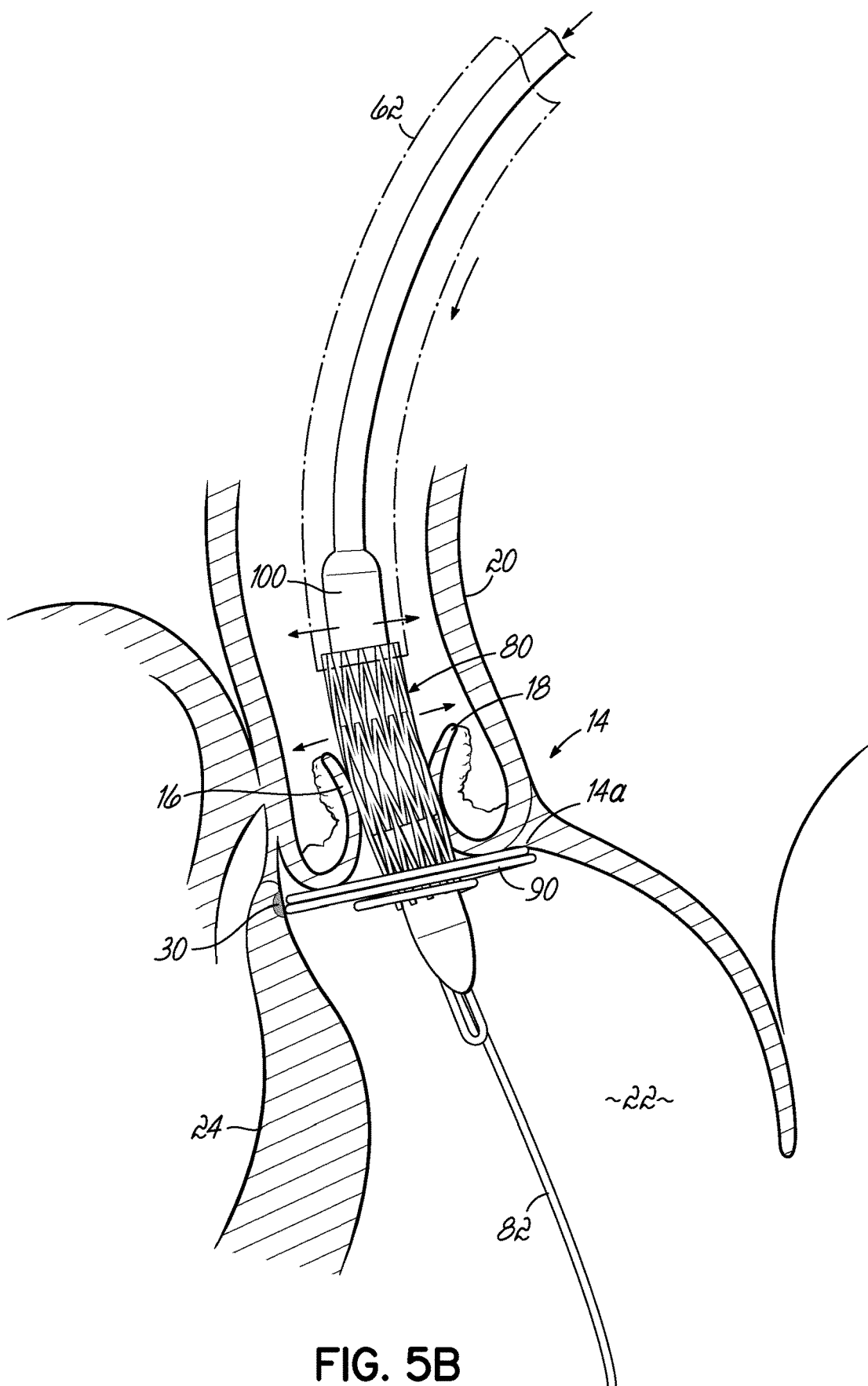
FIG. 5B is an illustration similar to FIG. 5A, but illustrating a further point in the method during which the delivery system and unexpanded stent valve are inserted through the native aortic valve and the guide device is drawn against an underside of the native aortic valve.

In FIG. 5B, the helical locator or sounding device 90 has been pulled back against the underside of the diseased aortic valve leaflets 16, 18.

The interventionist can feel the tension that will result. Also, the turns of the helix 90 will compress against each other so there will be a visual clue that the desired position under the leaflets 16, 18 of the valve 14 has been reached. As explained previously, the use of radiopaque markers may be useful on the helical guide or locator structure 90.

After the helical guide 90 has been pulled into position, the prosthetic valve 80 is pushed forward. The guide 90 and the prosthesis 80 can be constructed to ensure that the final position of the implanted valve 80 (after the stent valve 80 has been expanded and the stent valve 80 has shortened), is above the conduction tissue 30 but still securely inside the native leaflets 16, 18.

The relation between the position of the prosthesis 80 and the guiding device 90 can be fixed by placing stoppers on the guiding device 90. The operator can also move the prosthesis 80 so that there is the correct spacing between the guiding device 90 and the prosthesis 80. A pre-determined gap could be defined in millimeters from the upper turn or coil of the helix 90 and the position of the valve delivery system or catheter 62.

Figure 5C:
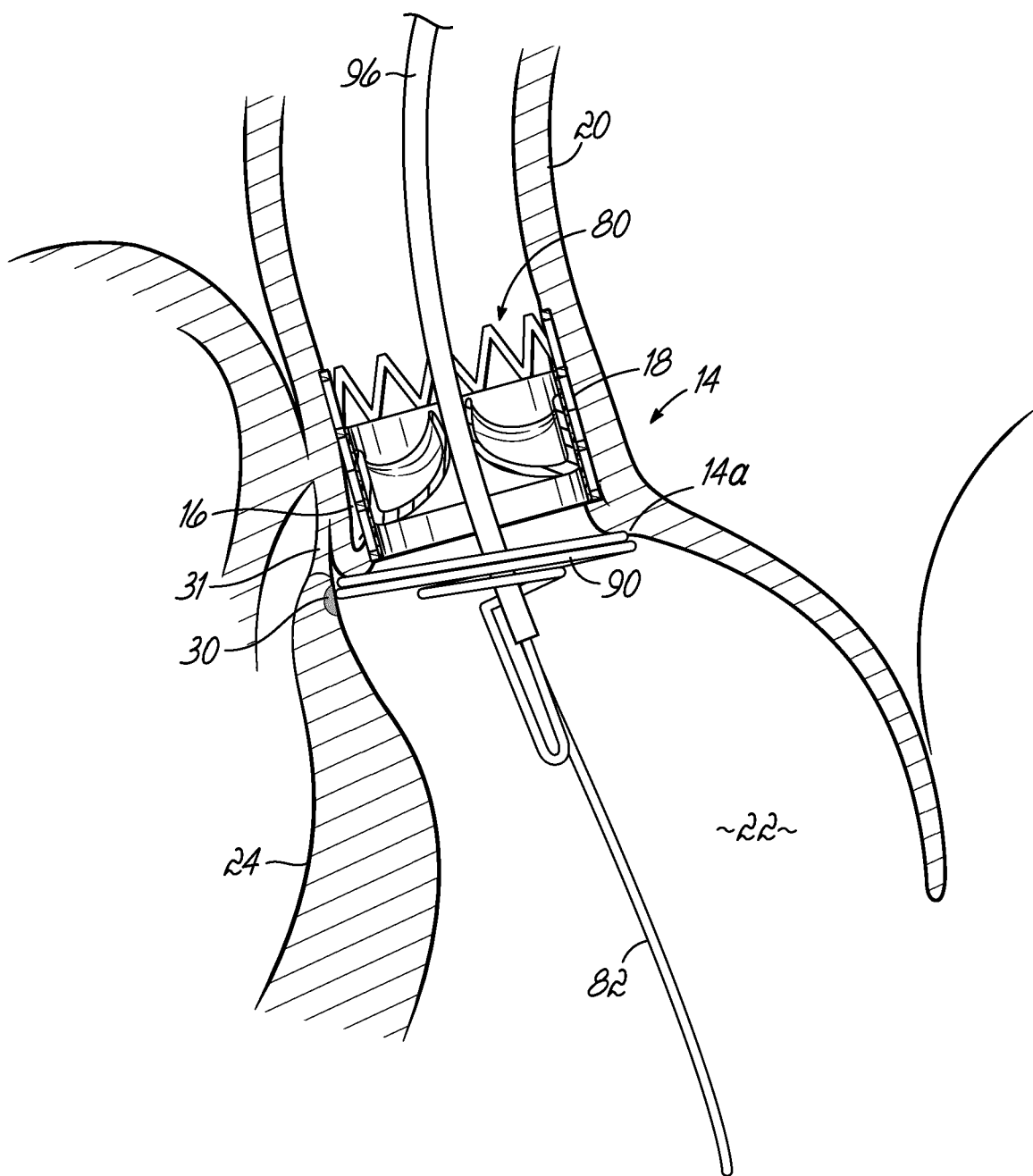
FIG. 5C is an illustration similar to FIG. 5B, but illustrating the prosthetic stent valve expanded, and with the guide device still in place.

In FIG. 5C, a balloon 100 (FIGS. 5A, 5B) has been inflated and removed. The valve prosthesis 80 is expanded inside the diseased native aortic valve leaflets 16, 18.

The valve 80 sits safely above the conduction tissue 30 that is at the top of the muscular septum 24. There is no risk of injury to the conduction tissue 30 by any structure of the stent valve 80.

The helical guiding or sounding device 90 is still in position.

As described above, it may be useful to add radiopaque markers (not shown) to the sounding or guiding devices, such as device 90. The markers could also be added to the balloon inflatable guiding structures, previously shown.

Clinicians may also find it useful to add EKG electrodes to the guiding or sounding devices. The membranous septum 32 above the conduction tissue 30 is not muscular. So an electrode contacting the membranous septum 31 will not show EKG activity. The addition of EKG detection to any of the sounding devices may precisely identify the location of the septal muscle 24 and membranous septum 32 for further improved guidance of the procedure.

It should also be noted that pre-procedure imaging is performed very commonly using CT, MR and Echo. Information derived from these studies could be used to determine the location of the membranous septum 32, the location of the lowest part of the aortic valve leaflets 16, 18, the diameter of the left ventricular outflow and the gap between the top of the muscular septum 24 (where the conduction tissue 30 reliably sits) and the native leaflets 16, 18. These measurements could help select a guide device that will impact in the left ventricular outflow at a point below the leaflets 16, 18. Or it could help to determine where to deliver a valve prosthesis relative to a marker on the guiding or sounding device.

These figures have shown a variety of guiding or sounding devices to identify the undersurface of the aortic leaflets 16, 18 or the left ventricular outflow. Inflatable and non-inflatable guide devices have been shown. These examples of position locating guides or sounding devices is not exhaustive but intended to show examples of the concept of using a locating device to guide an aortic prosthesis implant into a position that avoids negative contact with conductive tissue 30.

Figure 5D:
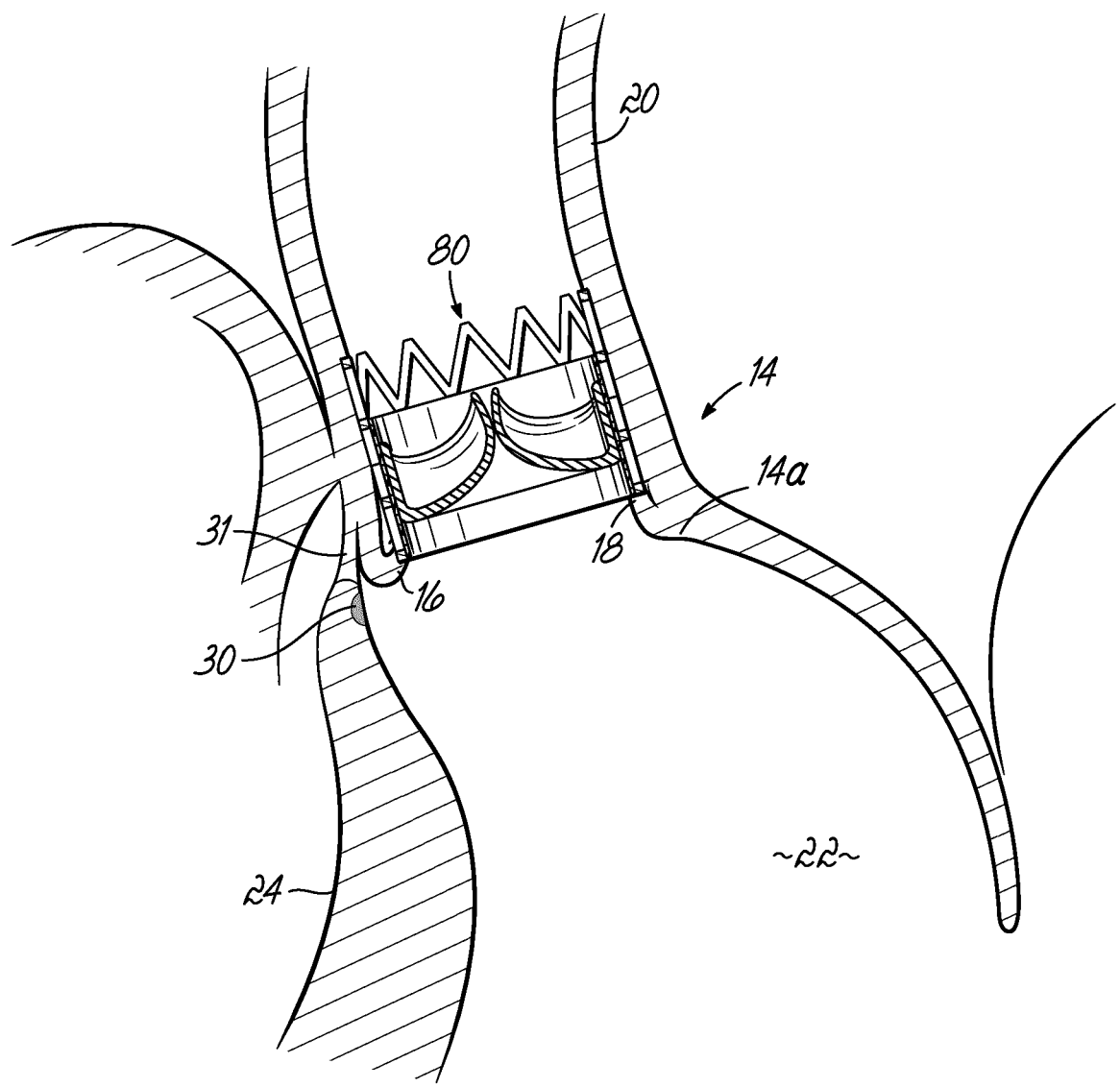
FIG. 5D is an illustration similar to FIG. 5C, but illustrating the guide device removed.

In FIG. 5D, the delivery system and guiding device has been removed. Only the prosthetic valve 80 remains. The valve stent 80 sits well above the conduction tissue 30. Heart block should not occur in this situation.

These figures have shown frames that are made from stents (self-expanding and balloon expanding) and inflatable frames. Other prosthetic valves are being used such as the Boston Scientific Sadra valve that has an adjustable frame. Any aortic valve implant or prosthesis could be combined with the position guiding or sounding concepts, methods and devices described in this disclosure.

The previous figures have all used the reference of the under surface of the aortic valve leaflets 16, 18 or the narrowing of the left ventricular outflow to position a sounding or locator device. It is also possible to use the upper surface of the aortic leaflets 16, 18 to obtain an internal reference point to guide implantation of a prosthetic valve.

Figure 6:
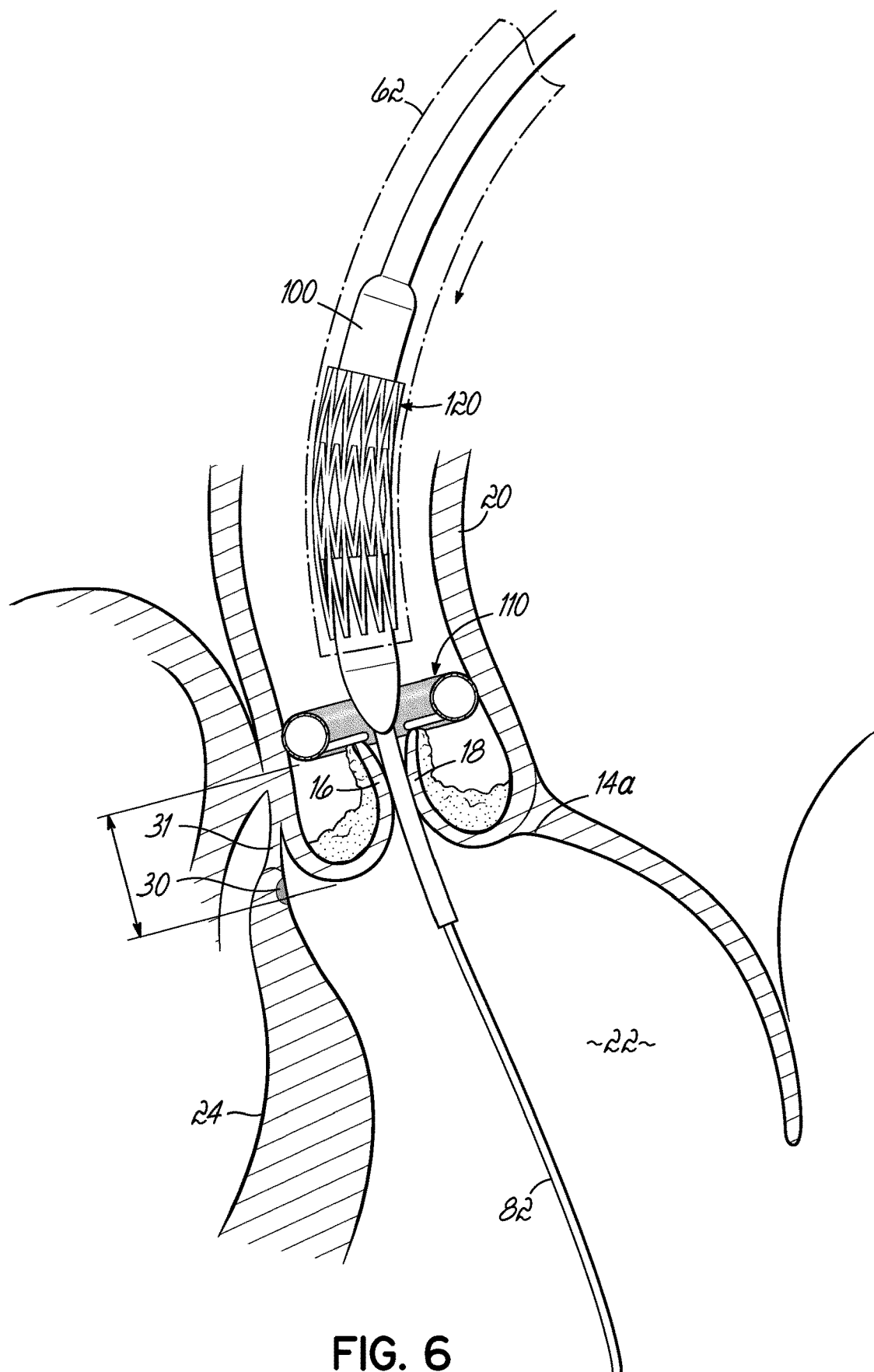
FIG. 6 is an illustration showing the anatomy cross sectioned, and the insertion of an expandable stent valve, using a guide device above the native aortic valve.

FIG. 6 shows an inflatable sounding or locating device 110 that is shaped like a doughnut. It is pushed forward until it stops inside the aorta 20 on the tops of the cusps of the aortic valve leaflets 16, 18. A valve prosthesis 120 is advanced relative to the position of the sounding (guide or locator) device 110. The ideal relative positions of the guide 110 and the correct location for deployment of the prosthesis 120 could be determined using pre-operative measurements from imaging that could reliably generate measurements from the tops of the cusps to the conduction tissue 30. The guide device 110 does not need to be inflatable. Guide devices such as those shown previously (like a helix or multi-armed anchor) could be used.

It appears to make most sense to use the underside of the valve 14 or the outflow of the left ventricle 22 for the guide (such as previously described) because this is so close to the location of the conduction tissue 30 and there should be less error in using this as a reference. However, clinical practice and in product development, the use of the upper plane of reference may show advantage.

Also, it may be useful to use guidance or sounding devices both below the native valve 14 and above the native valve 14. The operator could then visually or by the use of stoppers determine where to locate the position to deploy the prosthetic valve 120.

The disclosure above describes how a sounding or locating device can be used to help position a percutaneous valve for aortic valve replacement. Specifically, it has been found that the risk of heart block is increased when the valve prosthesis sits lower than 4 to 5 mm from the bottom of the native aortic valve 14. This is not surprising since the conduction tissue 30 that transmits the signal to the ventricles passes in this region and it is likely that the valve frame causes damage to the conduction tissue. The devices, method and systems described previously show how heart block can be avoided.

Disclosure below focuses on how the sounding or locating device can be placed to aid in ideal placement of the valve, and then moved during the procedure so that the locating device does not become trapped by the frame of the prosthetic valve. This allows the locating device to be easily removed at the end of the procedure.

The disclosure below also focuses on how the sounding or locating/guide device can be used to center the valve prosthesis during implantation. The prosthetic valve is generally inserted on catheters that travel around the curve of the aorta 20. Because of the curved insertion path, the valve prosthesis naturally has a tendency to locate itself to the outside of the curve—and not in the center of the native valve 14. It may be beneficial to have the valve prosthesis positioned in the center of the aortic outflow when it is deployed.

Figure 7A:
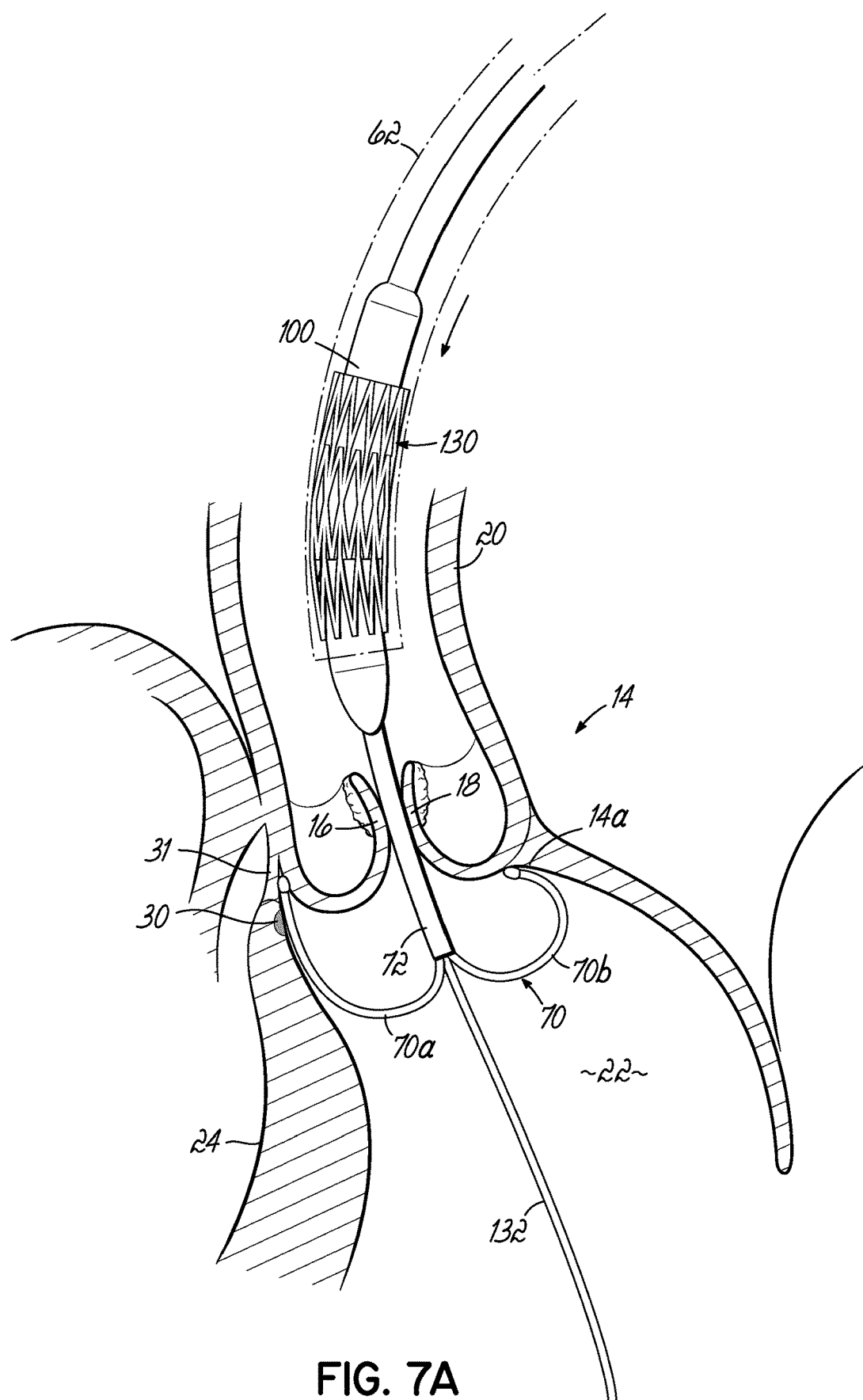
FIG. 7A is an illustration with the anatomy cross sectioned and showing the insertion of an expandable stent valve through the native aortic valve and a guide device within the left ventricle.

FIG. 7A shows a prosthetic aortic valve 130 being inserted inside a patient's diseased native aortic valve 14. A guide wire 132 has been directed into the left ventricle 22 through the valve delivery system 62. A balloon expandable stent valve 130 is being moved into position inside the diseased valve 14.

The sounding or locating device 70 is shown sitting under the aortic valve leaflets 16, 18. The sounding device 70 has been described previously. The arms 70a, 70b sit under the native aortic valve leaflets 16, 18. They can be positioned by "feel"—the interventional cardiologist can feel the tension as they are pulled back against the valve leaflets 16, 18 or this may be done visually by fluoroscopy.

The number and length and the configuration of the arms 70a, 70b can vary. There could be two or three or a much larger number of arms 70a, 70b. These arms are quite long and the tips of the arms 70a, 70b sit around the undersurface of the perimeter of the valve 14. The arms 70a, 70b could have a tighter turn and sit under the body of the leaflets 16, 18.

Figure 7B:
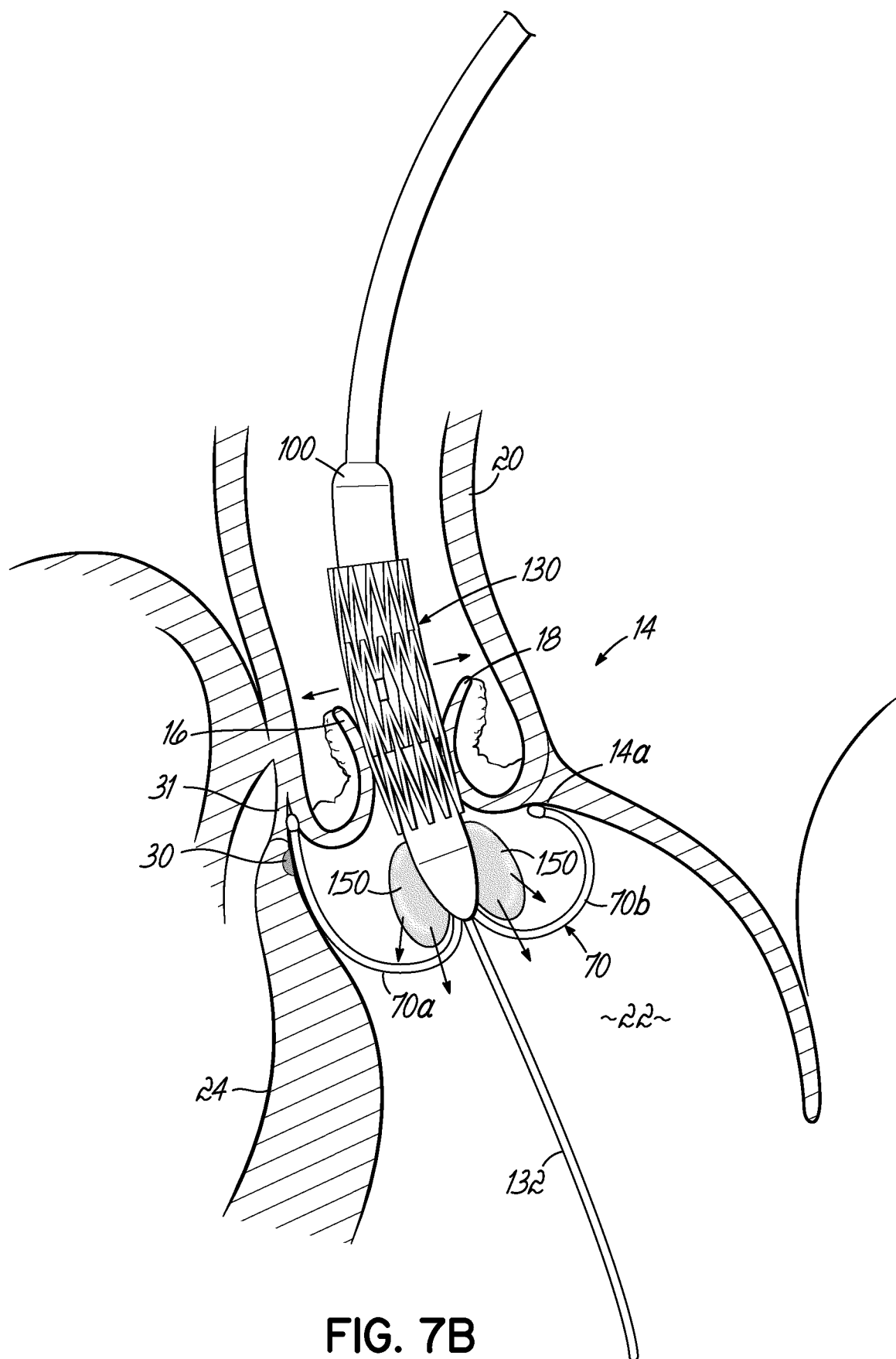
FIG. 7B is an illustration similar to FIG. 7A, but further illustrating an inflatable device being used to move the guide device out of position as the prosthetic stent valve is expanded.

In FIG. 7B, the aortic valve prosthesis 130 has been pushed into position and engaged relative to the sounding or locating device 70.

The system is constructed so that when the sounding device 70 is positioned under the native mitral valve 14, the prosthetic valve 130 will be delivered in the correct position. At this time the correct position for the final resting position of the lowest point of the valve stent 130 is thought to be no more than 4 mm from the bottom of the valve leaflets 16, 18. The system should be constructed so that the valve delivery system is correctly adjusted with the sounding or locating device 70 to deliver the desired final depth of for the prosthetic valve 130 that the system is using.

It should be noted that the balloon expanded stent valve 130 is collapsed for delivery in the catheter system. The collapsed stent 130 is longer than the final length of the expanded stent 130. So the system has to take into account the fact that a longer balloon 100 is necessary for delivery and that the stent valve 130 shortens as it is expanded by the balloon 100.

FIG. 7B shows a plurality of balloons 150 (two in this example) being inflated against the arms 70a, 70b of the locating device 70. Once the locating device 70 has been used to correctly position the valve 130, the valve 130 is ready for deployment. If the valve 130 is expanded immediately, there is a risk that the arms will become trapped under the expanded stent of the valve prosthesis 130. The two balloons 150 are shown being inflated prior to the inflation of the balloon 100 that inflates the valve 130. These serve to move the locating arms 70a, 70b away from the path of the expanding aortic valve prosthesis 130 to guarantee they will not be trapped in position and prevent the removal of the locating device 70.

The balloons 150 can be any in number. They can be located anywhere in the delivery system. They can be, for example, on the tip of the distal delivery system. They can be attached to the main stent expanding balloon 100 itself. They can be out-pouches of the main balloon 100 that inflates the valve 130.

Figure 7C:
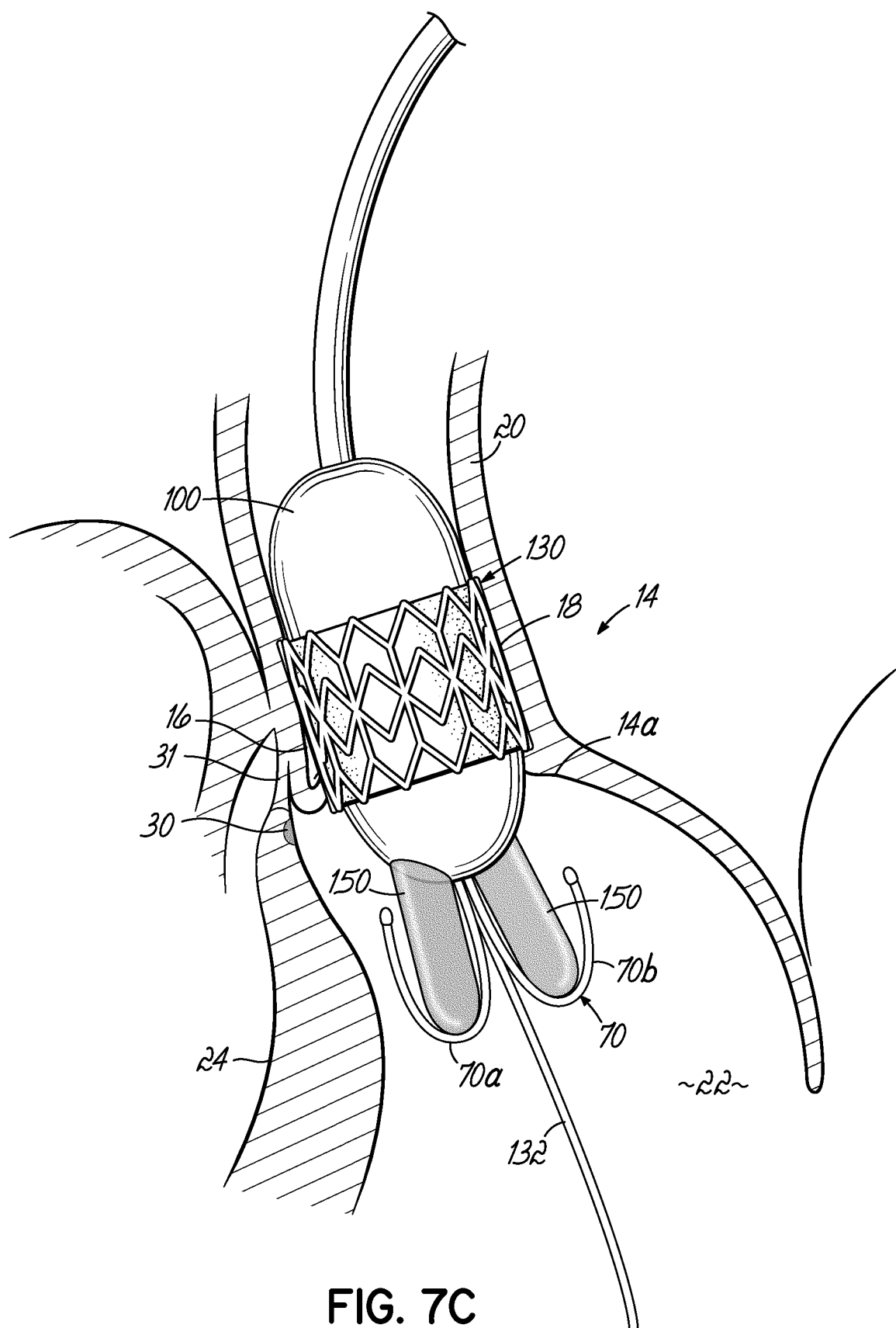
FIG. 7C is an illustration similar to FIG. 7B, but illustrating a further point in the process during which the stent valve is fully expanded by the balloon device, and other portions of the balloon device are moving the guide device out of the way.

FIG. 7C shows the locating arms 70a, 70b being pushed downward and away from the annulus 14a of the aortic valve 14. The arms are well clear of the inflating aortic valve prosthesis 130.

There are alternative approaches to using a balloon to move the locating or guide device out of the way during implantation of the valve prosthesis. Rods or pusher wires could be used to push the arms. Also, the operator could use the positioning device to achieve the desired location for the prosthesis. The positioning device could then be move away by the operator. The valve prosthesis could then be deployed. These locating devices could also be moved away manually before the valve prosthesis is deployed to avoid the need for balloons or other interventions to avoid trapping the locating device behind the valve.

Figure 7D:
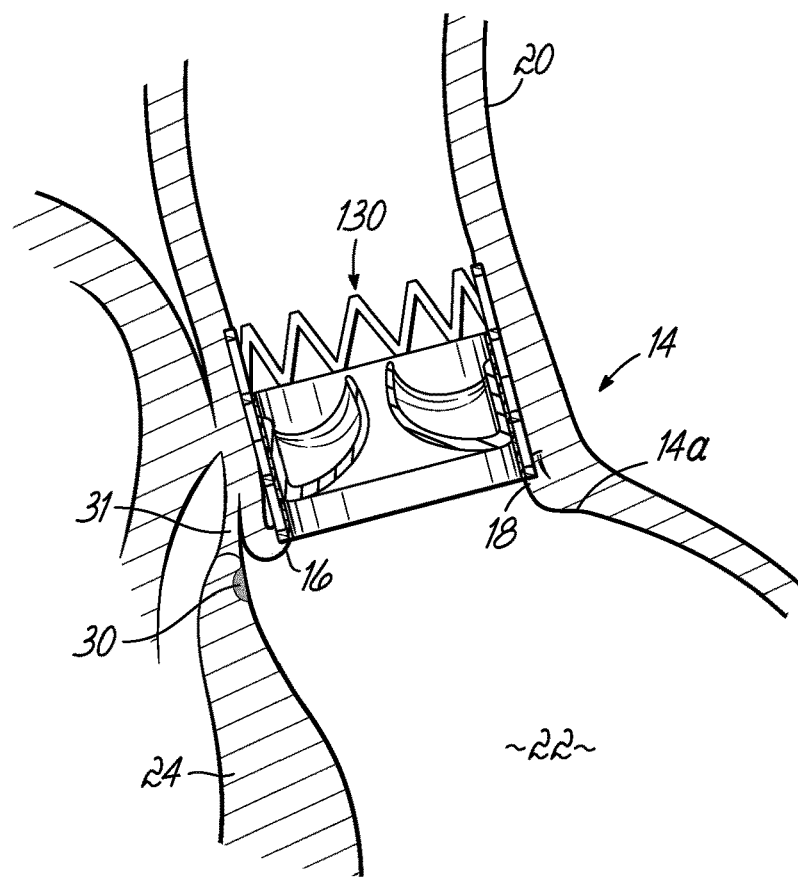
FIG. 7D is an illustration similar to FIG. 7, but illustrating the fully implanted expandable stent valve.

As shown in FIG. 7D, at the end of the procedure the locating device 70, and any other components of the delivery system are removed. The prosthetic valve 130 is in position. Note that the conduction tissue 30 is not contacted by the prosthetic valve 130. There should be no risk of heart block in this procedure.

Figure 7E:
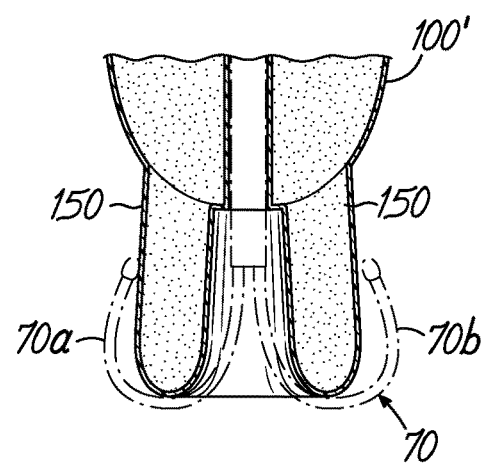
FIG. 7E is an enlarged cross sectional view illustrating the balloon device and guide device of FIG. 7C.

FIG. 7E shows a variation of a balloon 100' that forces the arms 70a, 70b of the locating device 70 away from the valve implantation site during implantation. The balloon 100' that pushes the arms 70a, 70b away could be separate from and have a separate inflation channel than the balloon 100 that inflates to expand the stent valve 130.

A common inflation channel makes most sense from the point of view of simplicity of construction. The valve 130 is tightly crimped on the inflating balloon 100. When the balloon 100 is first inflated, the parts 150 of a balloon 100 that pushes against the fingers or arms 70a, 70b will deploy since there is much less resistance to expansion. Once the fingers or arms 70a, 70b are pushed away, balloon 100 or 100' will begin to inflate the stent valve 130.

FIGS. 8A-8D show the implantation of a balloon expandable prosthetic aortic valve 130 with a helical shaped locating or sounding device 160.

Figure 8A:
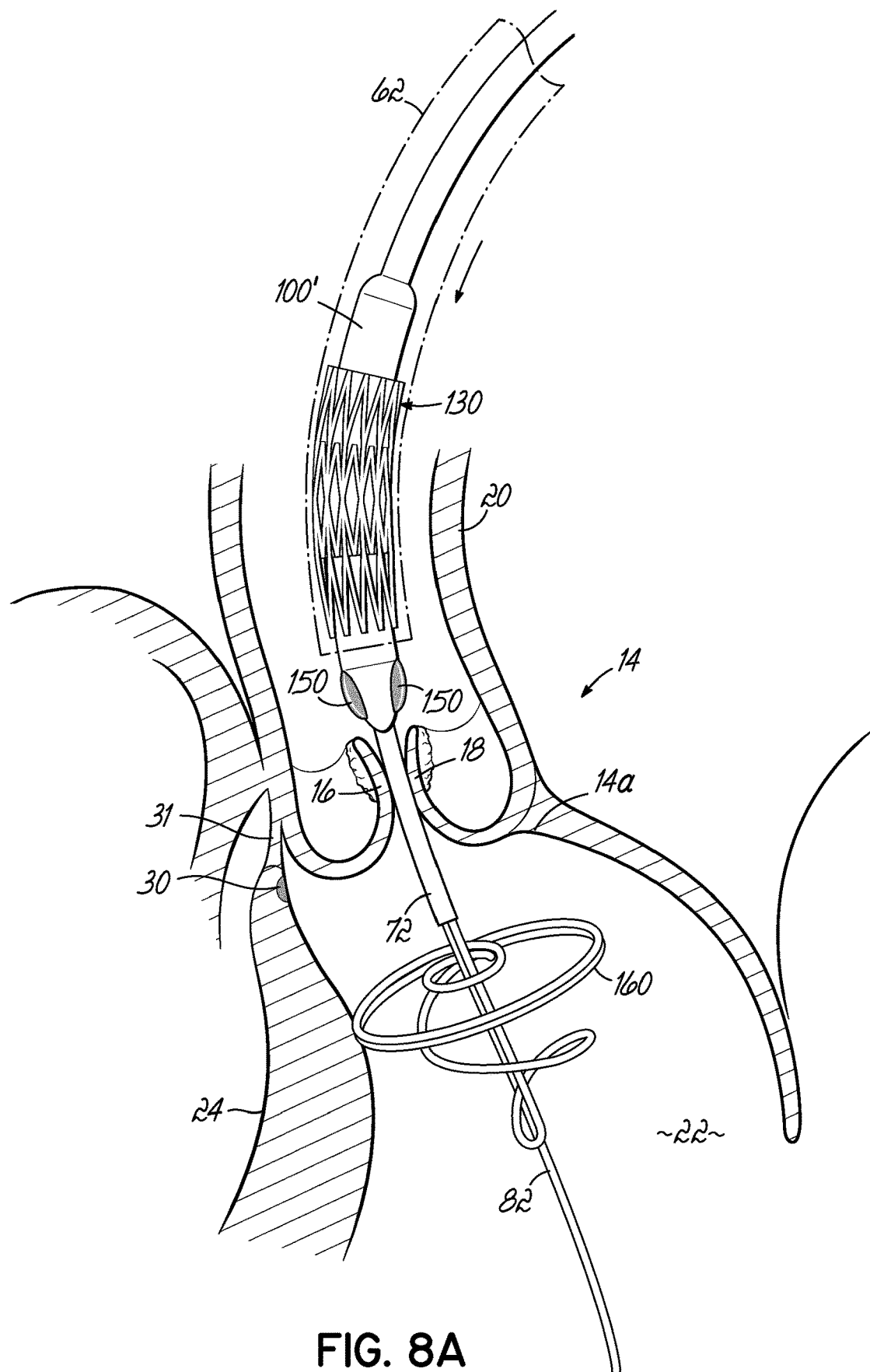
FIG. 8A is an illustration of the cross sectioned heart anatomy and the introduction of an expandable prosthetic stent valve into the aortic implant location, with a helical positioning guide device located in the left ventricle.

As in the previous figures and as shown in FIG. 8A, a guide wire 82 and the sounding or locating device 160 are positioned inside the left ventricle 22.

The valve prosthesis 130 is being advanced inside the patient's diseased native aortic valve leaflets 16, 18. On the tip of the delivery system is an inflatable component or balloon 100' that will be used to move the locating device 160 away from the implantation site.

Figure 8B:
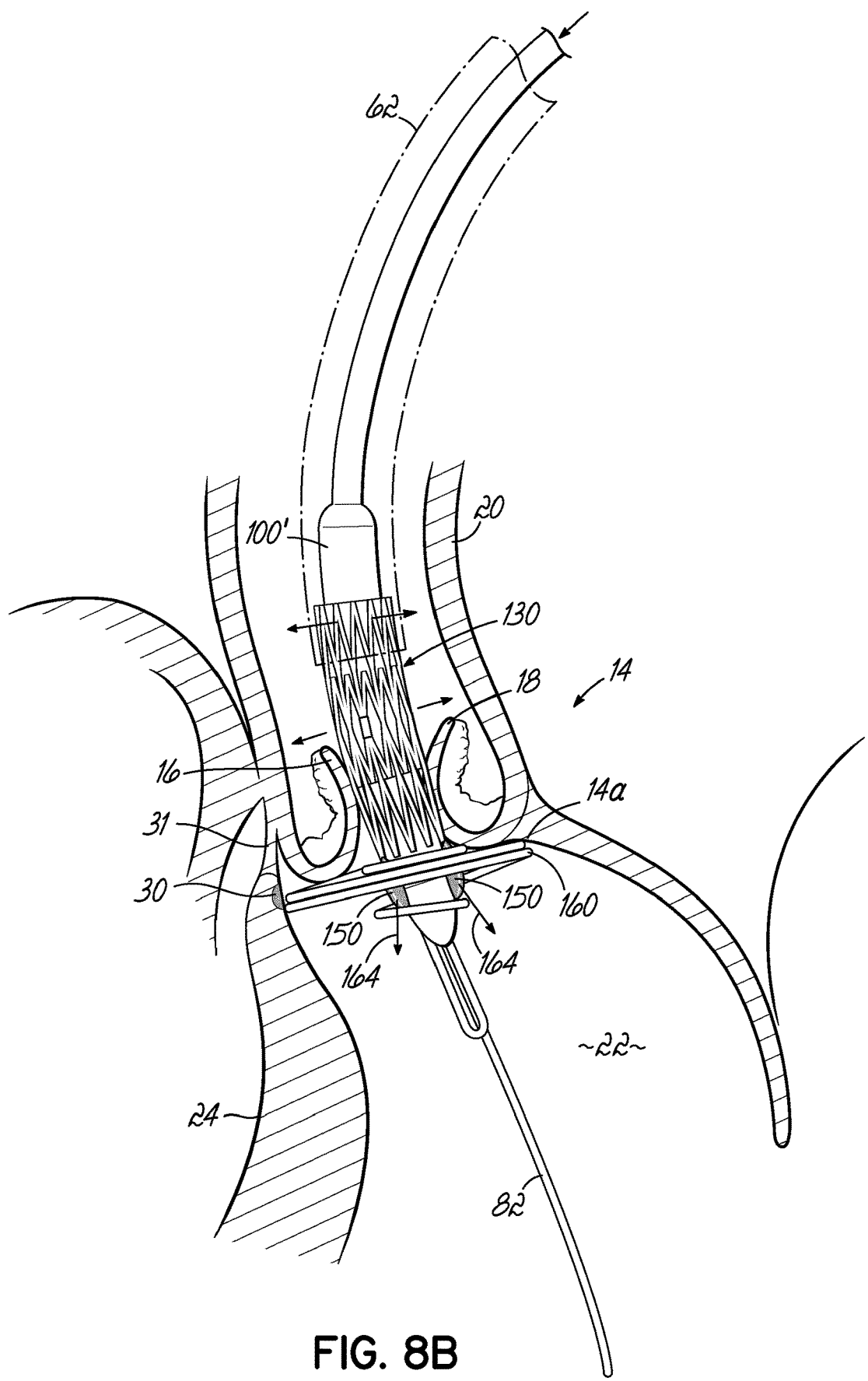
FIG. 8B is an illustration similar to FIG. 8A, but showing a further point in the method during which the expandable stent valve is located within the native aortic valve and the positioning guide device is drawn up against the underside of the native aortic valve.

In FIG. 8B, the locating device 160 has been pulled up against the underside of the aortic leaflets 16, 18.

The valve 130 has been positioned inside the patient's diseased aortic valve 14. The depth of the insertion of the valve 14 is guided by the sounder or locator device 160. This will ensure the correct depth of the implantation. Conduction tissue 30 can be avoided without implanting the valve 130 too high. Each prosthetic valve design will have to be carefully studied to ensure the positioning device results in the correct level of deployment.

If the balloon 100' was now inflated to expand the aortic valve prosthesis 130, there is a risk that the helix guide device 160 would be trapped under the prosthetic valve 130.

Two arrows 164 show the path of the expansion of the inflatable pusher 100'. Such inflatable balloons or elements 150 will engage against the locating device 160 and push the device 160 away from the frame of the valve 130 once it has served its function of correctly positioning the valve 130.

The helical sounding or locator device 160 has a number of turns or coils located in approximately the same plane. The helical sounding or locator device 160 may also have turns in different planes. For example, the helix 160 could form a conical shape that is open toward the aortic valve annulus 14a with turns or coils that are wider closer to the native annulus 14a.

One particularly useful shape (not shown) may be a circular locator device that has a sinusoidal shaped portion moving to and away from the annulus 44a. These sinusoidal shaped portions could also be included in a helix.

The locator or sounding device can have many useful alternative shapes.

Figure 8C:
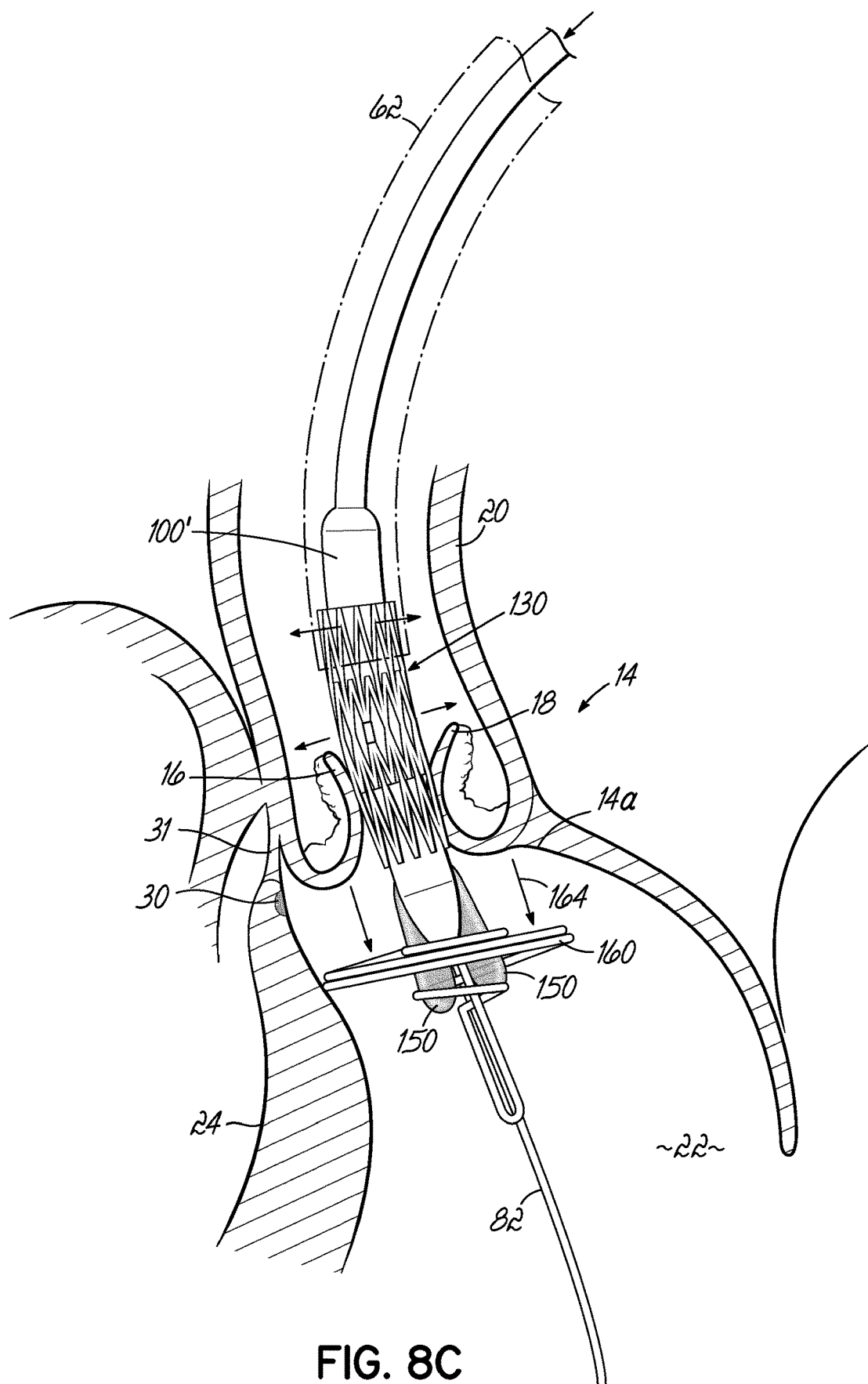
FIG. 8C is an illustration similar to FIG. 8B, but showing a further point in the method during which the guide device is moved out of the way by expandable balloon elements as the stent valve is expanded.

FIG. 8C shows the valve prosthesis 130 is now in the correct position. The inflatable pusher 100' has been expanded. The helical positioning or locator/sounding device 160 is now pushed away from the valve 130 and the valve 130 is now ready to be expanded into position. The path of expansion of the prosthetic valve stent 130 is shown with the horizontal arrows 168.

Figure 8D:
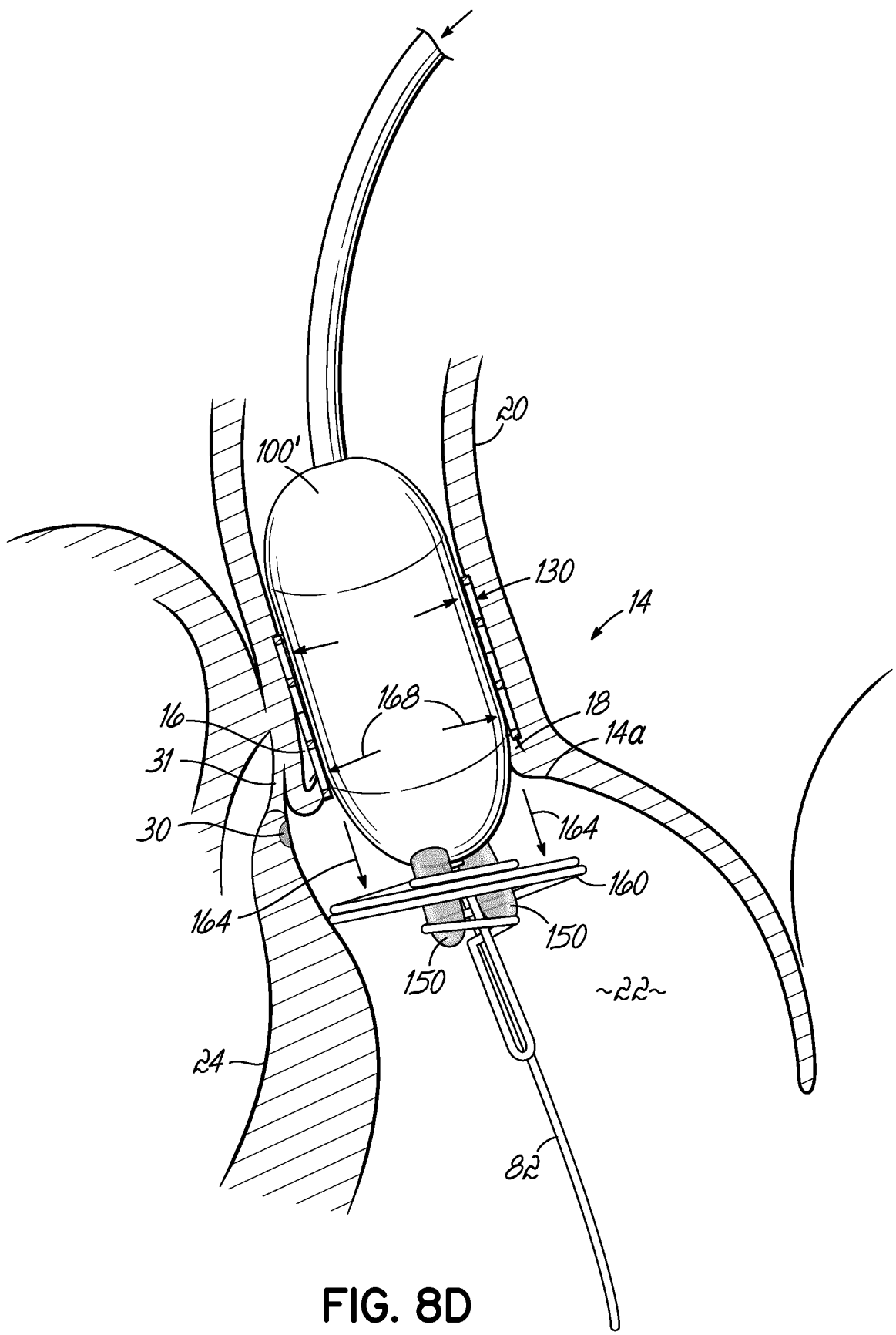
FIG. 8D is an illustration similar to FIG. 8C, but showing a further point in the process during which the guide device has been moved out of the way and the prosthetic stent valve has been more fully expanded against the leaflets of the native aortic valve.

As shown in FIG. 8D, the balloon 100' has now fully expanded the stent of the prosthetic valve 130.

The inflatable pusher 100' moved the sounding device 160 away from the implant site so it is not trapped by the valve 130.

The inflatable pusher elements can be of any number. They can be mounted on the distal tip of the delivery system or be associated with the balloon that expands the prosthetic valve 130 or they could be a separate element. As explained previously, it is not necessary to use balloons to push the locating device 160. A mechanical rod could be used. Or the locating device 160 could simply be moved by the interventionist prior to fully implanting the valve prosthesis 130.

Figure 9A:
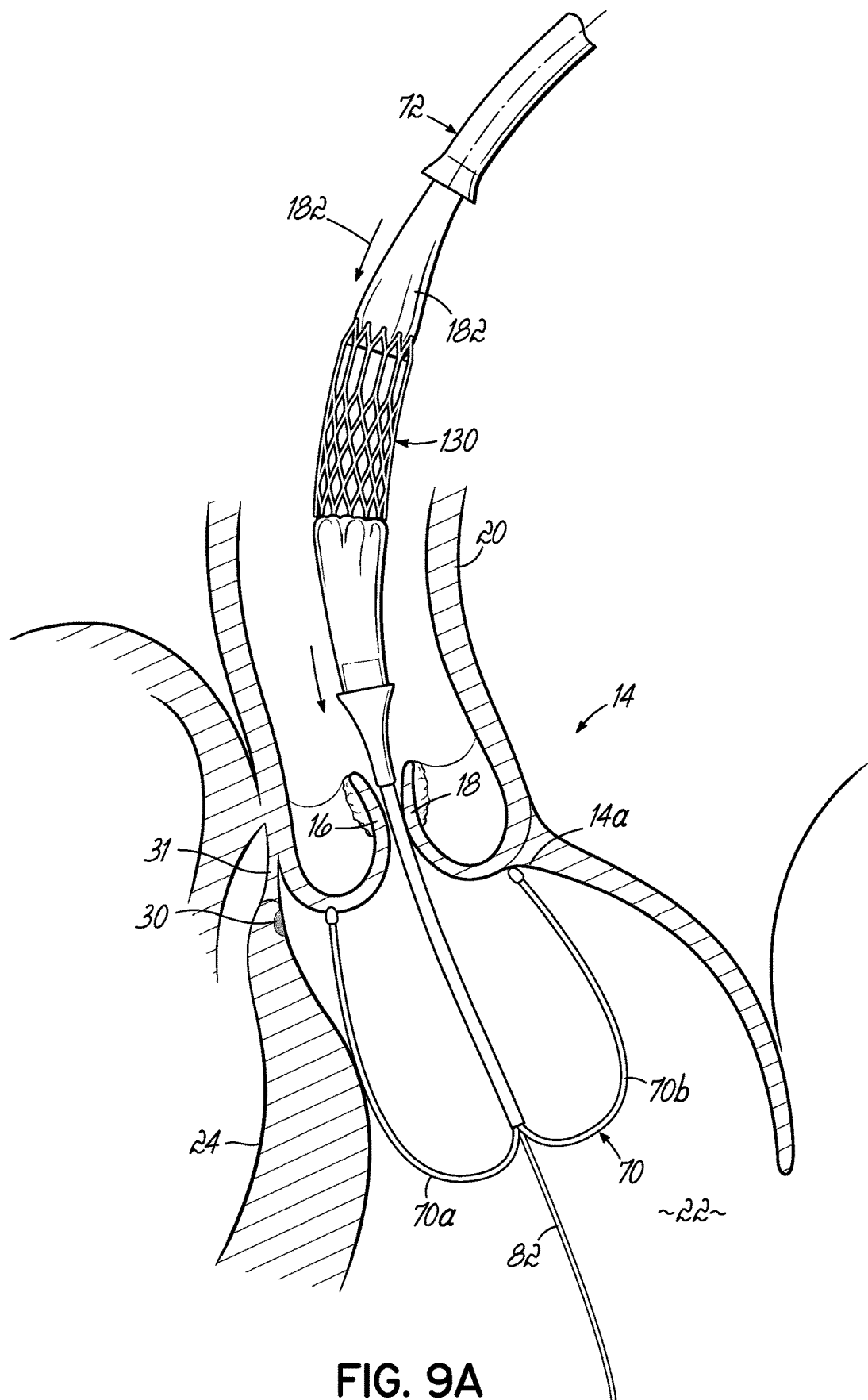
FIG. 9A is an illustration of another embodiment showing the insertion of an expandable stent valve into the implant location of the native aortic valve, and a positioning guide device located in the left ventricle.

FIG. 9A shows the implantation of a balloon expandable prosthetic aortic valve 130 that is similar to the Edwards Sapien 3 system. The stent valve 130 is crimped and mounted on a balloon 180 that is longer than the valve prosthesis 130. A sounder or locator device 70 is positioned below the aortic valve 14. It should be noted that the locating device could be a different shape. For example, the locating device 70 could be instead formed as a helical structure. The stent valve delivery system is being pushed over a guide wire 82 inside the diseased native aortic valve leaflets 16, 18. The arrows 182 indicate the direction of travel.

Figure 9B:
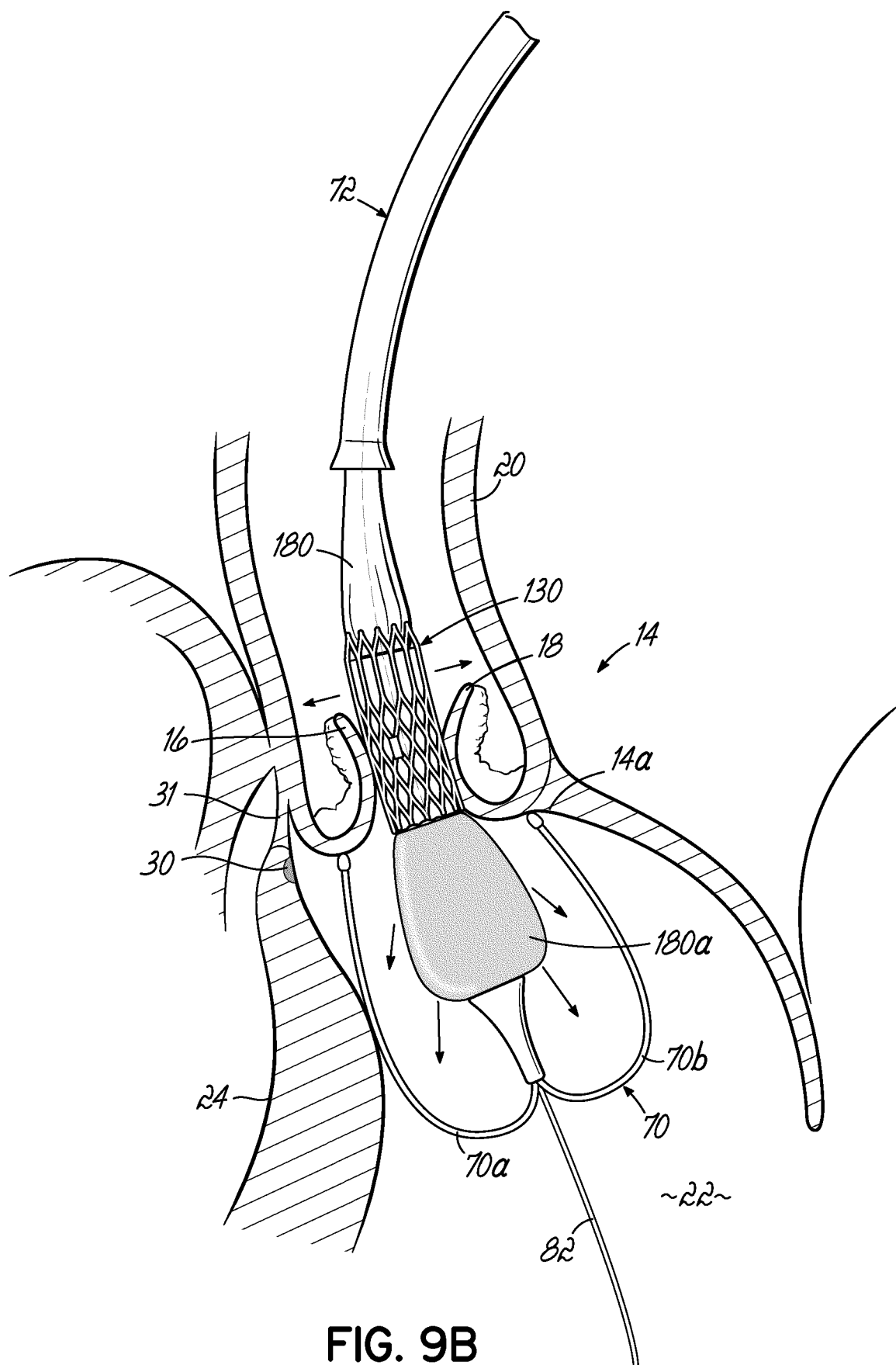
FIG. 9B is an illustration similar to FIG. 9A, but further showing a point in the process during which the stent valve has been inserted into the native aortic valve.

In FIG. 9B, the valve 130 is positioned in the correct position by the locating device 70 so that the expanded valve 130 will not contact the conducting tissue 30. The balloon 180 is expanded. The distal part 180a of the balloon 180 expands first as no stent is crimped on it and there is no resistance to its expansion. The expanding balloon portion 180a moves toward the arms 70a, 70b of the locating device 70.

The system could also be constructed so the distal tip of the delivery system is moved forward to push the locating device 70 away. This could be activated by the balloon 180 or by a mechanical push mechanism (not shown) in the delivery system.

Figure 10A:
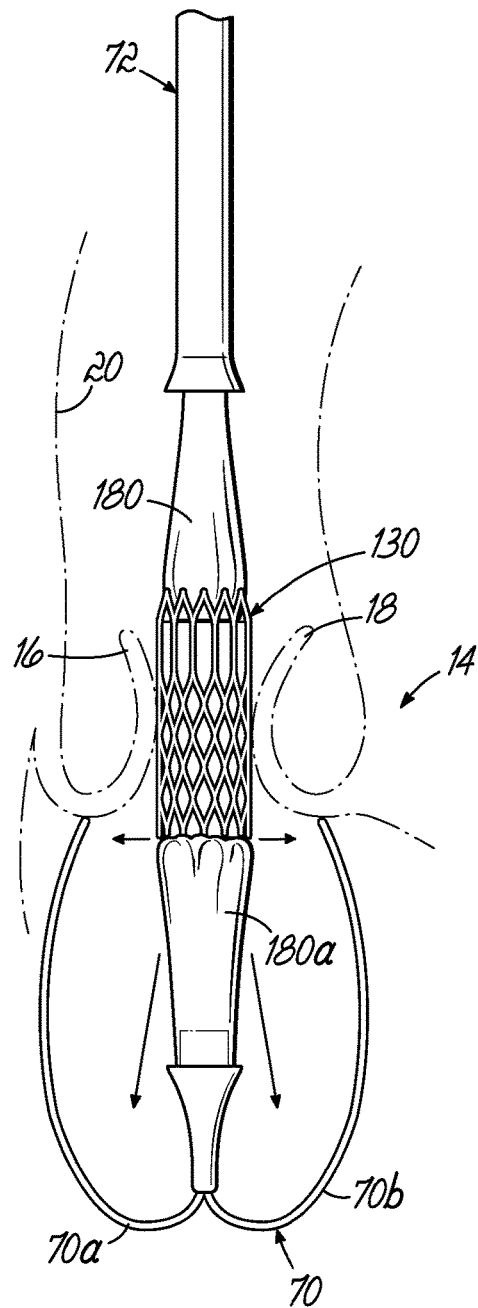
FIGS. 10A through 10C are similar views to the methodology shown in FIGS. 9A and 9B, more specifically showing the progression of valve expansion and movement of the guide device out of the way with additional balloon elements or portions.
Figure 10B:
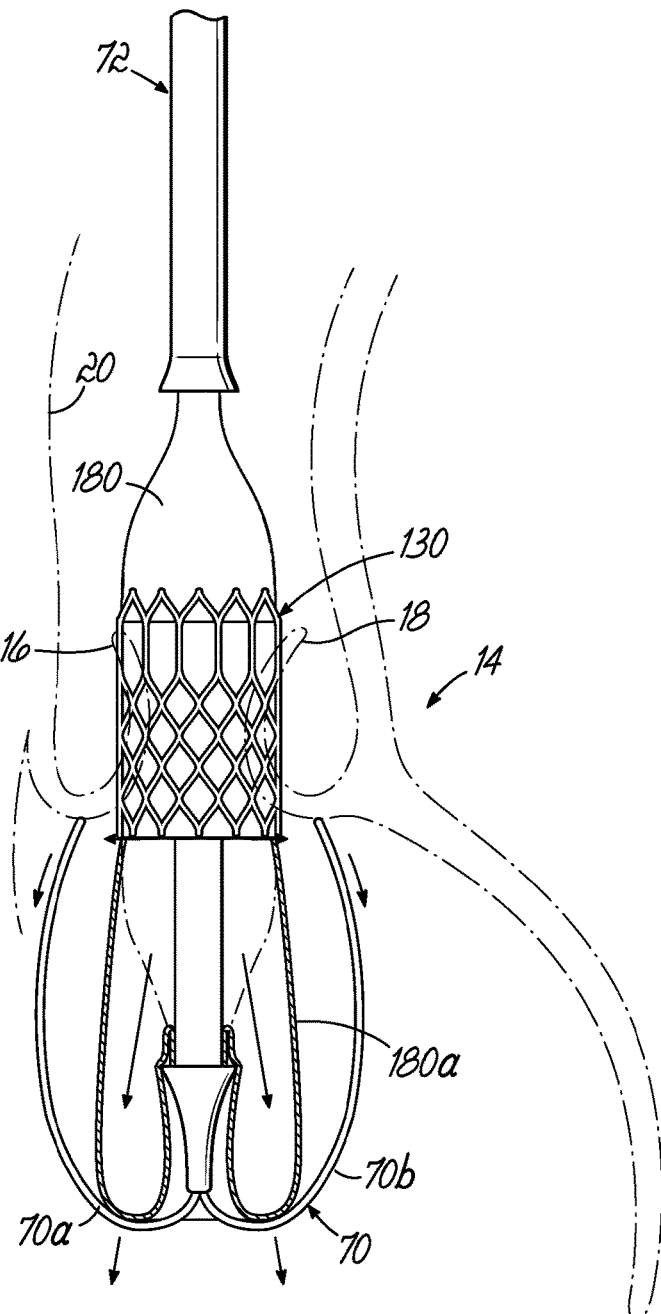

FIGS. 10A and 10B show cross sections of the profile of the balloon 180 respectively before and after inflation. This balloon 180 expands like a tube or cylinder to push the locating device 70 away from the annulus 14a.

Figure 10C:
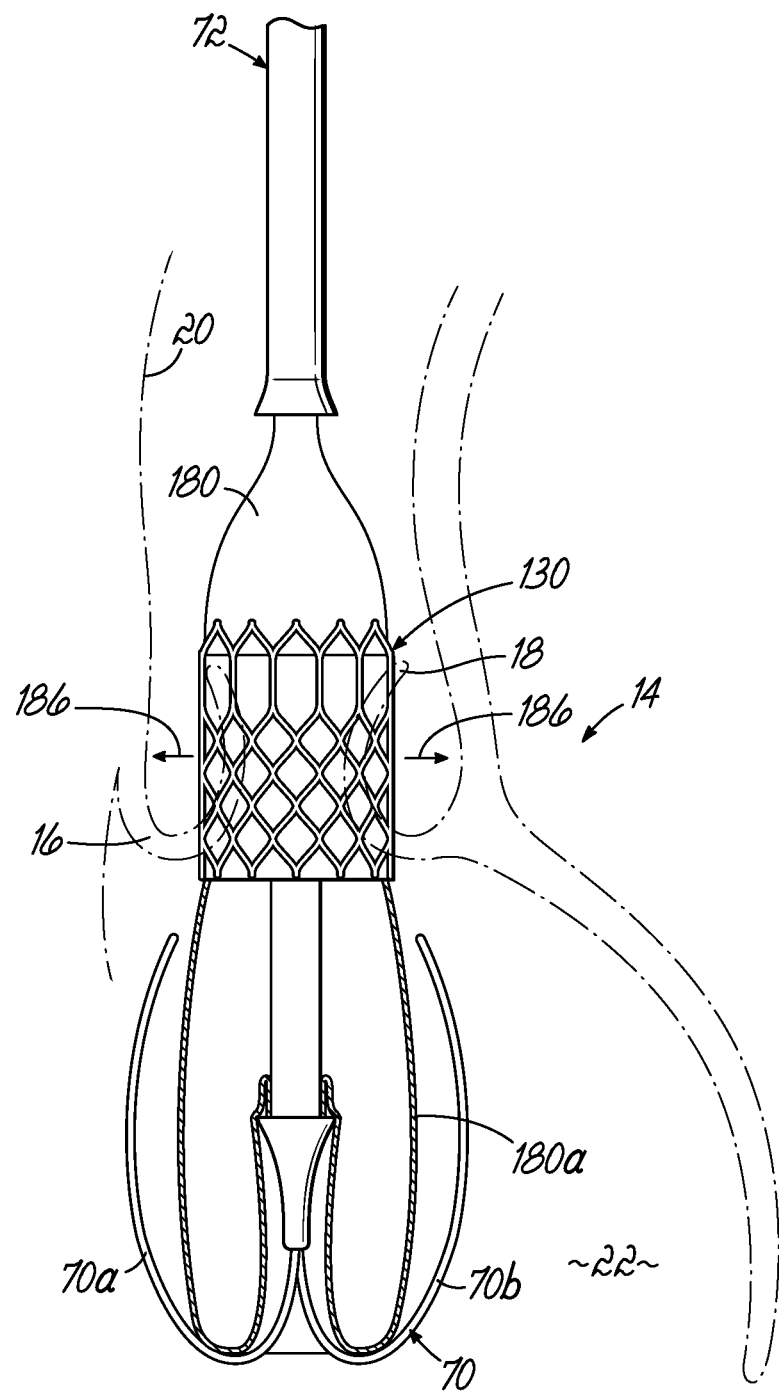

As shown in FIG. 10C, after the locating device 70 has moved away, the balloon 180 now expands the aortic valve prosthesis 130. The arrows show the balloon expanding the stent of the valve. The arrows 186 show the valve stent 130 moving outwards.

It is important to note that the arms 70a, 70b of the locating device 70 are moved free of the path of the expanding aortic valve prosthesis stent 130. For this reason, the arms 70a, 70b will not be trapped.

Figure 10D:
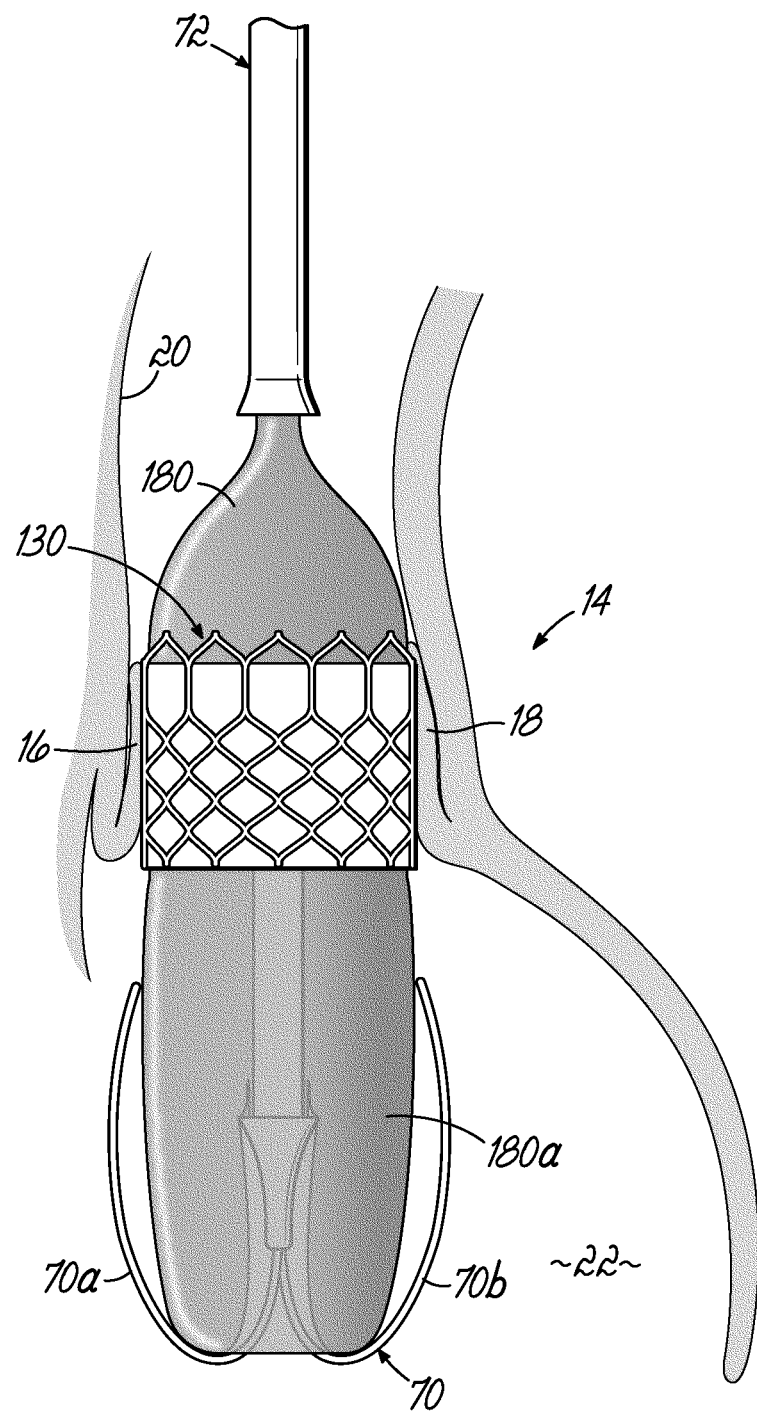
FIG. 10D is a view similar to FIG. 10C, but illustrating full expansion of the prosthetic stent valve and movement of the guide device out of the way such that it not trapped between the stent valve and native tissue.

FIG. 10D shows the valve 130 fully expanded. The locator arms 70a, 70b are free of the implant site. The balloon(s) 180 will be deflated and removed. The stented valve prosthesis 130 will be securely expanded in the correct anatomic location.

FIGS. 11A through 11D show the implant of a self-expanding version of an aortic valve prosthesis 190. This is similar to the valve that are sold by Medtronic and St Jude Medical.

Figure 11A:
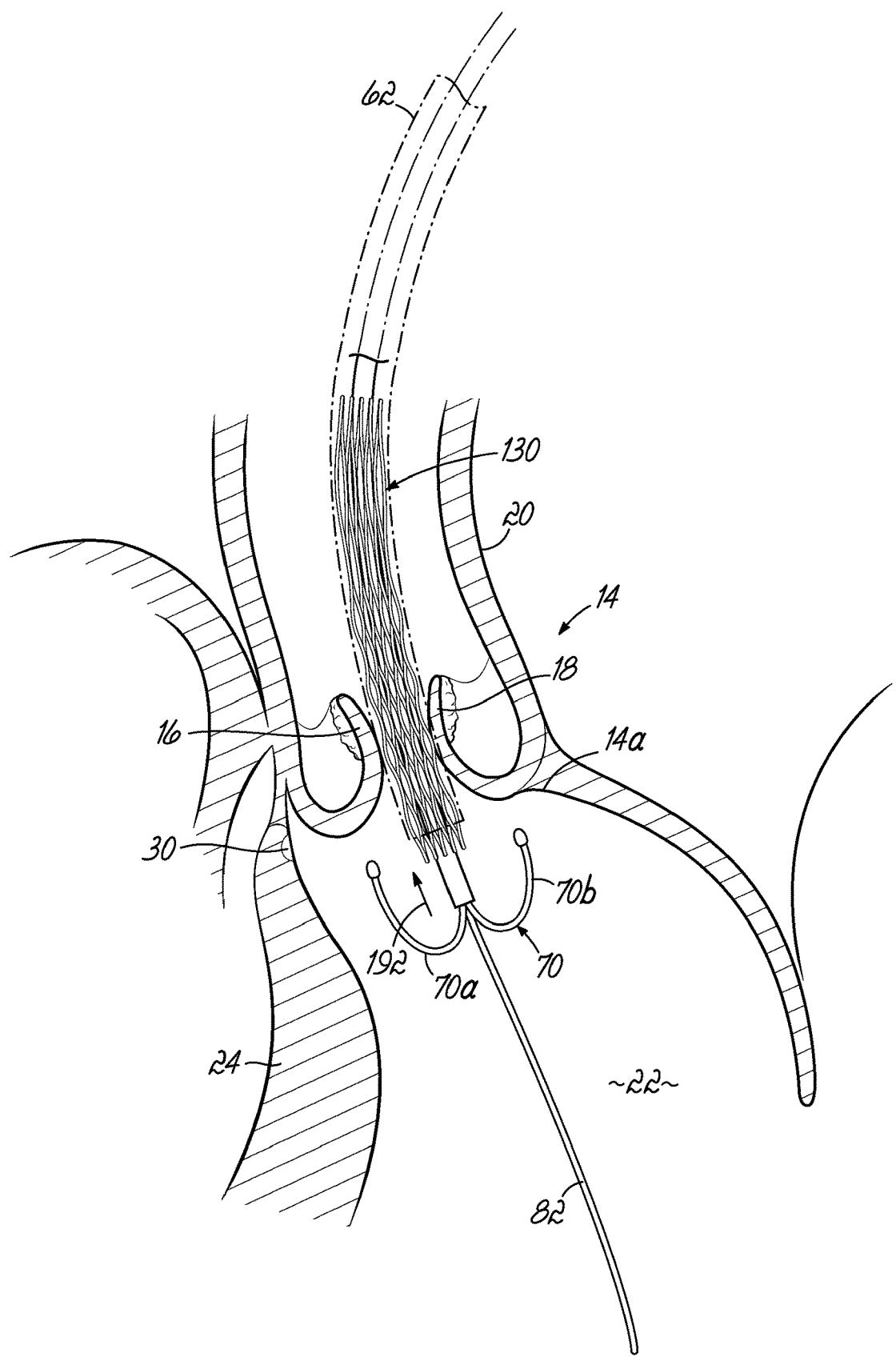
FIGS. 11A through 11D illustrate another embodiment in which both a height or level guide device and a centering device are used to position a stent valve during insertion and expansion of the valve.

As shown in FIG. 11A, the valve 190 is collapsed inside a sheath 62. A valve locating device 70 has been positioned in the left ventricular outflow. A guide wire 82 passes through the center of the delivery system and extends into the left ventricle 22. The arrow 192 shows the locating device 70 being pulled back to the correct guiding location under the aortic valve leaflets 16, 18. The arms 70a, 70b of this sounding or locator device 70 are shorter than previously shown.

Figure 11B:
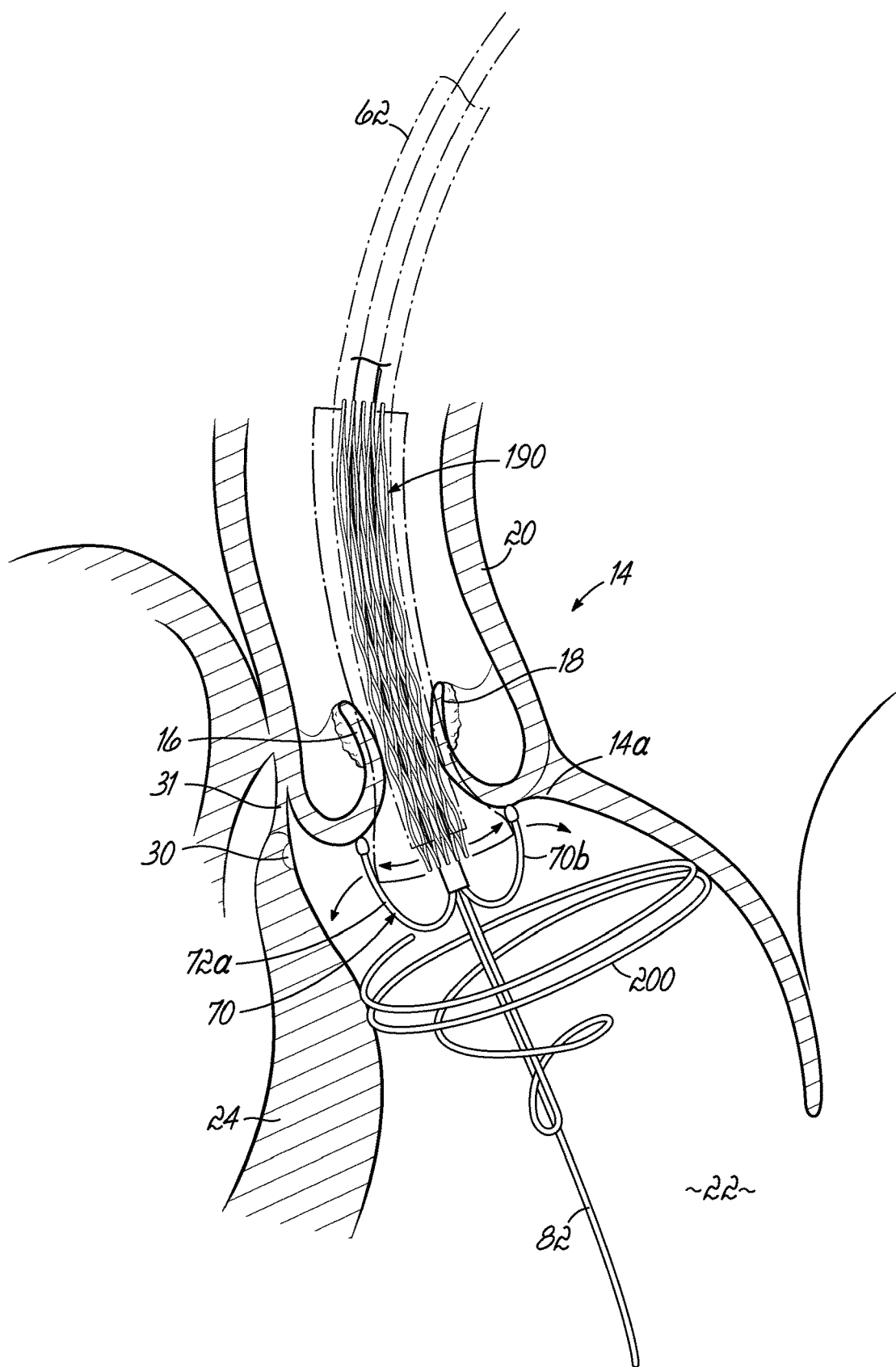

As shown in FIG. 11B, the arms 70a, 70b of the sounder or locator 70 are now in the correct position under the diseased aortic valve 14. The valve delivery system 62, 82 is advanced into the correct position as guided by the sounder or guide device 70. This arrangement will ensure the valve 190 does not sit too low in the annulus 14a.

FIG. 11B shows a supplemental or optional variation of the sounder or guide device 70 that includes a helix 200. The helix 200 may be helpful to keep the valve prosthesis 190 centered in the annulus 14. The helix 200 could be separate or attached to the sounder device 70 shown in the figure. The helix 200 is not the only way to center the arms 200. A second layer of larger arms (not shown) could be used for example at the level of the helix 200.

The aortic valve prosthesis 190 is generally inserted from the groin and around the aortic arch. The valve 190 typically does not pass directly through the center of the annulus 14a but to one side (the opposite side from the natural inner turn of the aortic arch). Note that these sounding devices 70, 200 also serve to center the position of the valve delivery system 62, 82 in the aortic annulus 14a. The centered position may make delivery more reliable.

Figure 11C:
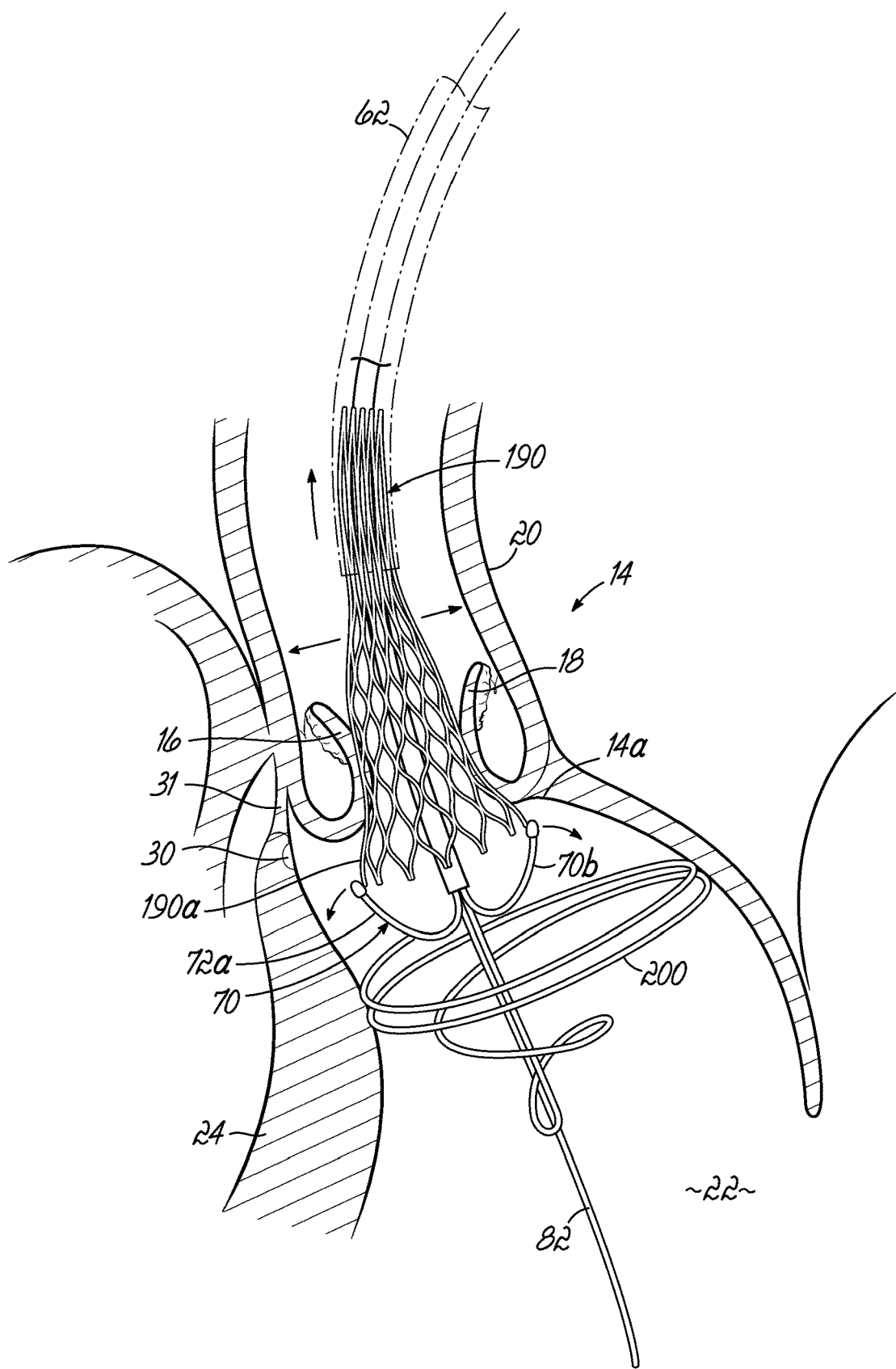

As shown in FIG. 11C, the sheath 62 holding the valve 190 is withdrawn (vertical arrow 206 shows the sheath 62 being moved backward) and the valve 190 begins to spring into position. Arrows 208 show the expansion of the valve 190 laterally. The flared end 190a of the self-expanding valve 190 pushes the sounder arms 70a, 70b away. The sounder or guide/locator 70 will not be trapped by the stent valve 190. The arms 70a, 70b will flip over the expanding end 190a of the valve 190 and avoid being trapped.

Figure 11D:
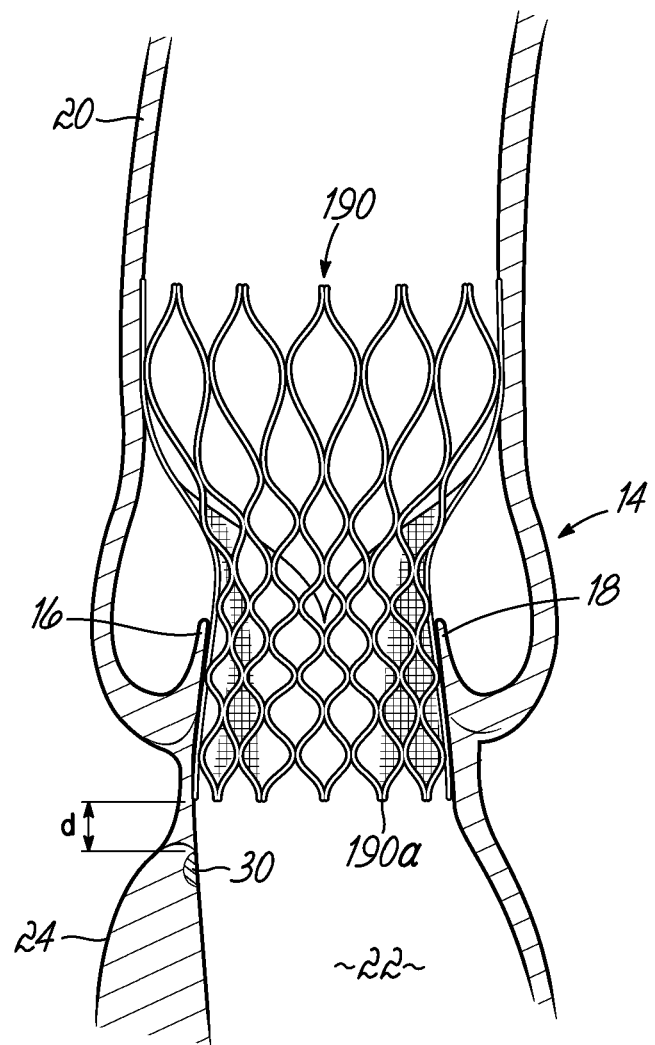

FIG. 11D shows the stent valve 190 in the final position. The distance "d" is marked to show the lowest point of the valve 190 sits considerably above the conduction tissue 30.

Figure 12A:
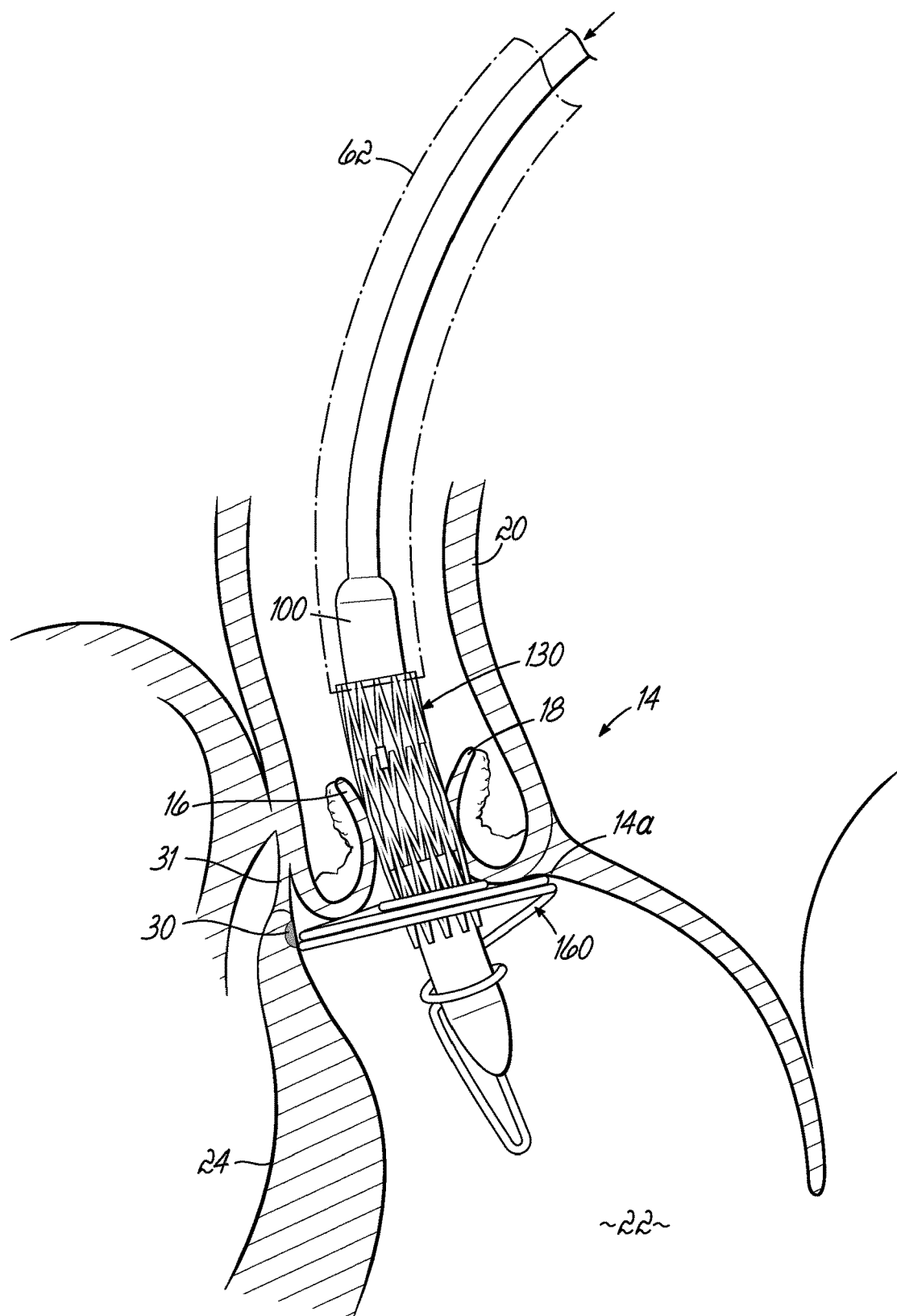
FIGS. 12A through 12C illustrate another embodiment of a guide device and the progressive methodology used for inserting and expanding a prosthetic aortic valve while using the guide device to locate the stent valve away from the conduction tissue.

Referring now to FIG. 12A, during implantation of a prosthetic valve 130 using a catheter system 62, 82, there are some high risk periods. When the prosthetic valve 130 is moved inside the native valve 14 the opening for flow of blood out of the left ventricle 22 is seriously reduced and the patient can become unstable very quickly. At the same time the implanter needs to be sure that the valve 130 is positioned safely. The valve 130 can sit too high and eject into the aorta 20. The valve 130 can sit too low and fall into the ventricle 22. And a valve 130 securely placed can still impact against conduction tissue 30. As shown in FIG. 1 in the series on valve modifications to avoid heart block, the left bundle branch LBB (FIGS. 15 and 16) sits just under the aortic valve 14 in the area of the junction between the right coronary cusp and the non-coronary cusp of the native aortic valve 14. Implanting a valve 130 even slightly too low can result in heart block. This problem is very common with self-expanding valves—where up to 30% of patients may develop heart block after the procedure.

As the prosthetic valve 130 is placed inside the native aortic valve 14 there is a lot of stress in rushing to complete the procedure to avoid cardiovascular instability coupled with the need to implant at the correct level within the valve 14. The implanter has to move very quickly during this period of time. It makes considerable sense to decide on the location and depth of implant before the prosthetic valve 130 is placed inside the native aortic valve 14. This can be accomplished by using guides or templates that are positioned appropriately before the prosthetic valve 130 is introduced. The guides or templates have the thickness of guide wires so they have little effect on flow. The implanter can take time and position these guides correctly and at relative leisure. The valve 130 for implant can be quickly implanted using the positioning template or guide device. This leads to high quality implantation and less stress. The time during which the valve 14 is obstructing the outflow (before it is deployed) is very low.

Clinical experience has shown that implanting a valve 130 so that the lowest part of the valve 130 is no more than 4-5 mm from the bottom of the native aortic valve 14, virtually eliminates heart block. Using a sounding/positioning/guide, the precise location of the underside of the aortic valve 14 can be identified. This narrow guide device can be set in position at leisure and then the prosthetic valve 130 can be fed over the guide device or template. The valve 130 can be deployed immediately—the decision about the location for implantation has already been made and it has been set by the guide device or template.

The guide device or template can be inserted using a delivery system of current prosthetic valves.

From a procedural approach, it makes most sense to begin the procedure by introducing a catheter inside the left ventricle and then introducing a guide or template through this catheter into the left ventricle 22.

The guide device or template can then be positioned appropriately under the native aortic valve 14. This sets the position for the implant procedure. This decision is made with relatively little obstruction to blood flow from the heart (i.e., only a wire obstructs flow).

For the valve implantation, the prosthetic valve 130 can be fed over the track of a wire that serves as a guide device or template and into position inside the native aortic valve 14. The valve 130 can be implanted by inflating a balloon or by unsheathing the valve (self-expanding variety).

The overall effect is to allow a very speedy implant at a pre-determined site. There should be less instability for the patient, less stress on the implanter and a more reliable implantation. Errors due to stress and rushing should be reduced. Inexperienced physicians may be most helped by this system.

FIG. 12A shows a positioning or locating tool or guiding device 160 that has a helical shape. It has been placed inside the left ventricle 22 through a catheter. The helix 160 has been pulled back until the helix 160 contacts the underside of the aortic valve 14. This maneuver will precisely locate the underside of the valve 14. The implanter will feel the helix 160 engage against the valve 14 as the helix 160 is drawn back. Also, on fluoroscopy, the helical guide device or helix 160 will be distorted when the helix 160 is pulled against the native valve 14.

The helical guide device 160 has a proximal wire portion that passes out the groin of the patient. The wire is passed through a central lumen (not shown) of the prosthetic valve delivery system. The prosthetic valve 130 is then introduced into the patient from the groin. The valve 130 shown here is similar to the balloon inflated prosthesis from Edwards Lifesciences. The template or locator/positioning tool 160 will stop the advance of the prosthetic valve 130 at the appropriate site. The valve 130 will now be in the ideal position. The implanter can now immediately begin to expand the valve 130. There is no need to wait and take multiple images, and multiple steps to ensure the valve 130 is in the correct position. The implanter can immediately begin to expand the valve 130.

For a self-expanding valve 190, the implanter can immediately go ahead and unsheathe the delivery system. For a balloon expandable valve 130, the implanter can inflate the balloon 100.

When the valve 130 is in the ideal position inside the native valve 14, the channel for blood flow through the valve 14 is very small. This risky phase is extremely short when the valve position is set by a guide or template 160.

In this figure, the prosthetic valve 130 is stopped or definitively located by a coil of the helix 160. The valve 130 could also be stopped by a protrusion or deviation (not shown) in the template or locator device 160 or any other useful configuration.

Figure 12B:
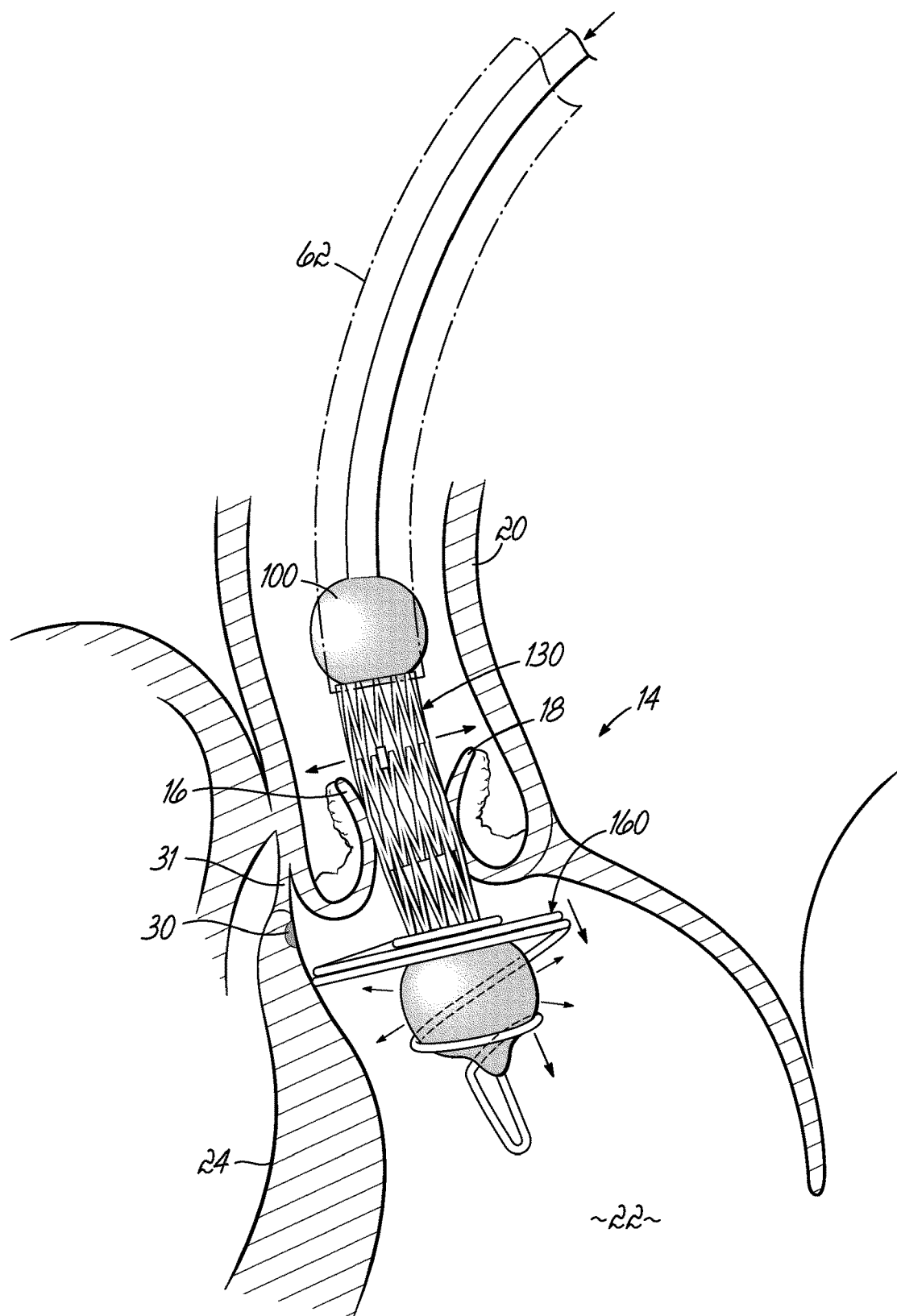

Referring to FIG. 12B, immediately after the valve prosthesis 130 is positioned, the balloon 100 to implant the valve 130 can be inflated. The balloon 100 inflates like a dumb bell. The two ends expand first because the central part of the balloon 100 has the stent frame of the valve 130 crimped over it. The distal end of the balloon 100 engages with the helix 160. The helix 160 moves forward or distally into the left ventricle 22. This keeps the helix 160 from being trapped under the expanding valve 130.

Figure 12C:
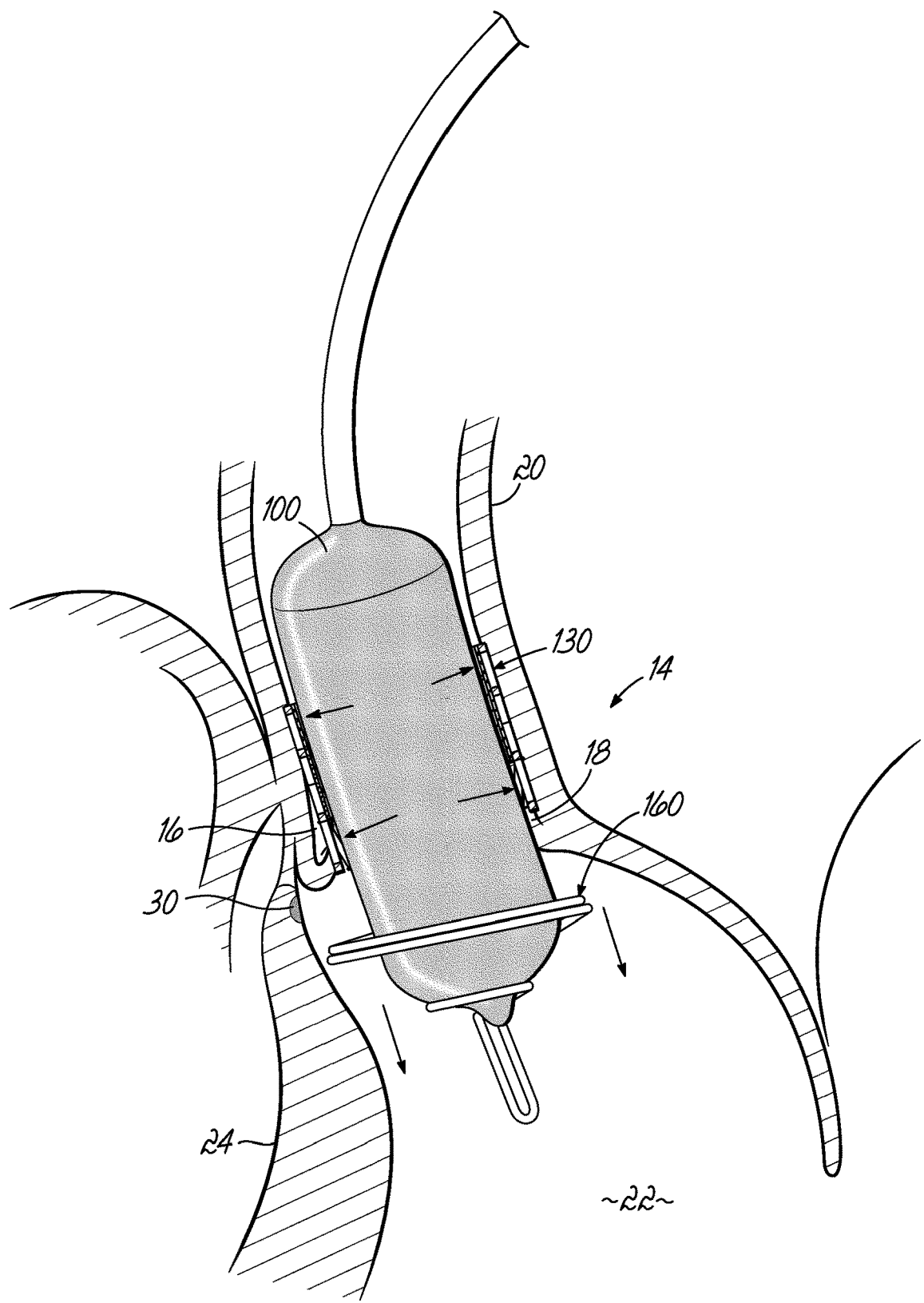

As shown in FIG. 12C, expansion of the valve 130 continues as the balloon 100 is inflated. The valve prosthesis 130 is now fully expanded inside the native valve 14. The conduction tissue 30 is not contacted by the stent frame of the valve 130. The valve position is excellent. The delivery system and the template 160 can be withdrawn from the patient leaving a prosthetic valve 130 away from the conduction tissue 30. The sounding or locating or guide device 160 would likely best be made from a shape memory material like Nitinol. This can be shaped in a factory and then delivered through a catheter. It will be appreciated from a review of the procedure shown in FIGS. 12A through 12C that the helical guide 160 provides both a level or height-positioning function for the valve 130 to ensure that the lower portion or margin avoids engagement with the conduction tissue, but also a centering function for the valve 130 to ensure that the valve 130 is not implanted in a manner skewed relative to the longitudinal (blood flow) axis of the native valve 14. The balloon 100 aids in this centering function, for example, as its distal tip engages with the helical guide 160. The guide device 160 may take other shapes instead.

Figure 13A:
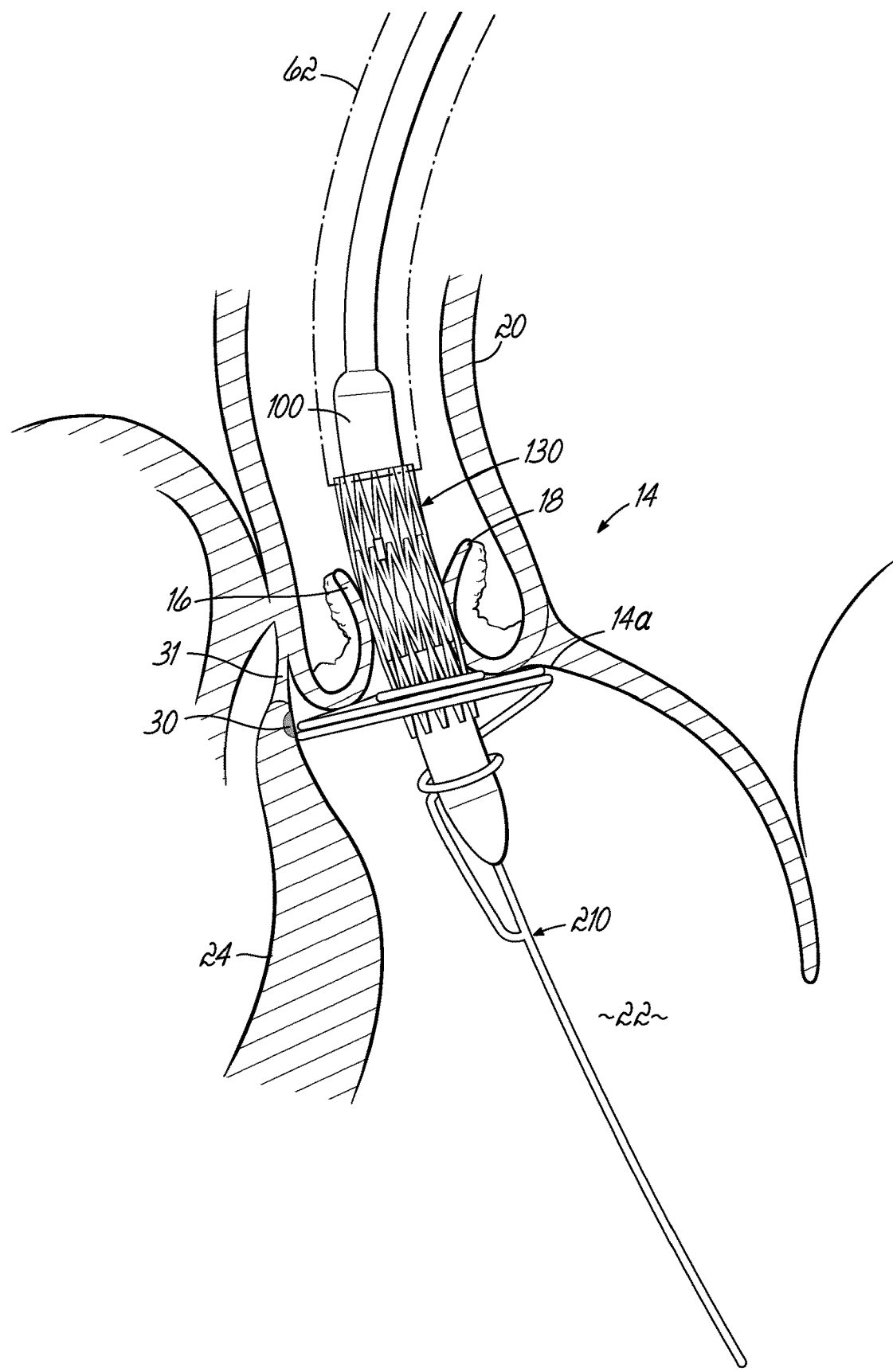
FIGS. 13A through 13C illustrate the progression of a method for using another alternative embodiment of a guide device for positioning a stent valve within the native aortic valve and away from the conduction tissue, while simultaneously moving the guide device out of the way during the implantation process.

Referring to FIG. 13A, there are many ways to make a guide, locator or template that performs the function of aiding in the positioning of a prosthetic valve (as these and other synonymous terms are used herein). Interventional specialists commonly use a simple guide wire for conventional purposes in the left ventricle.

Figure 13B:
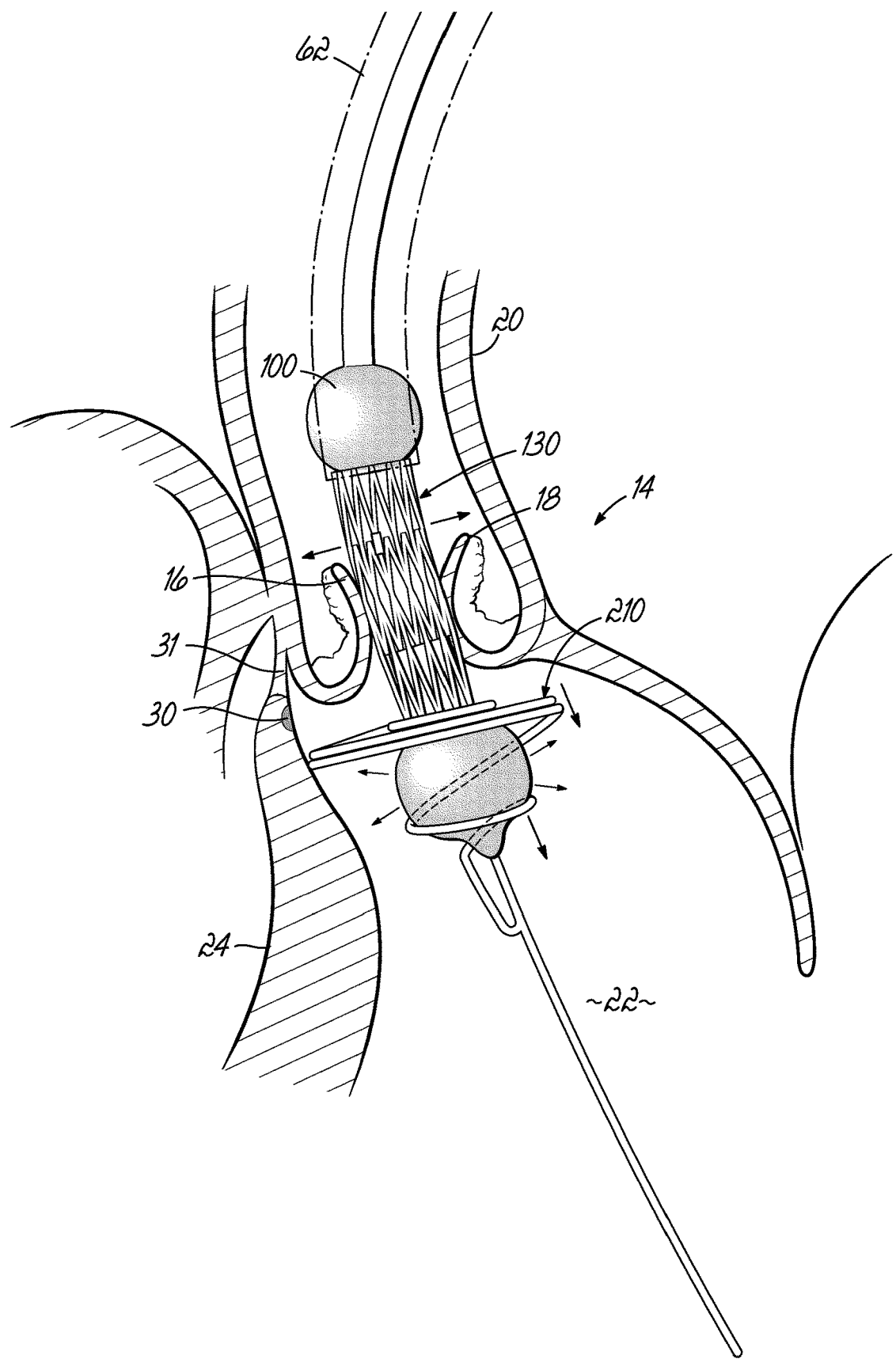
Figure 13C:
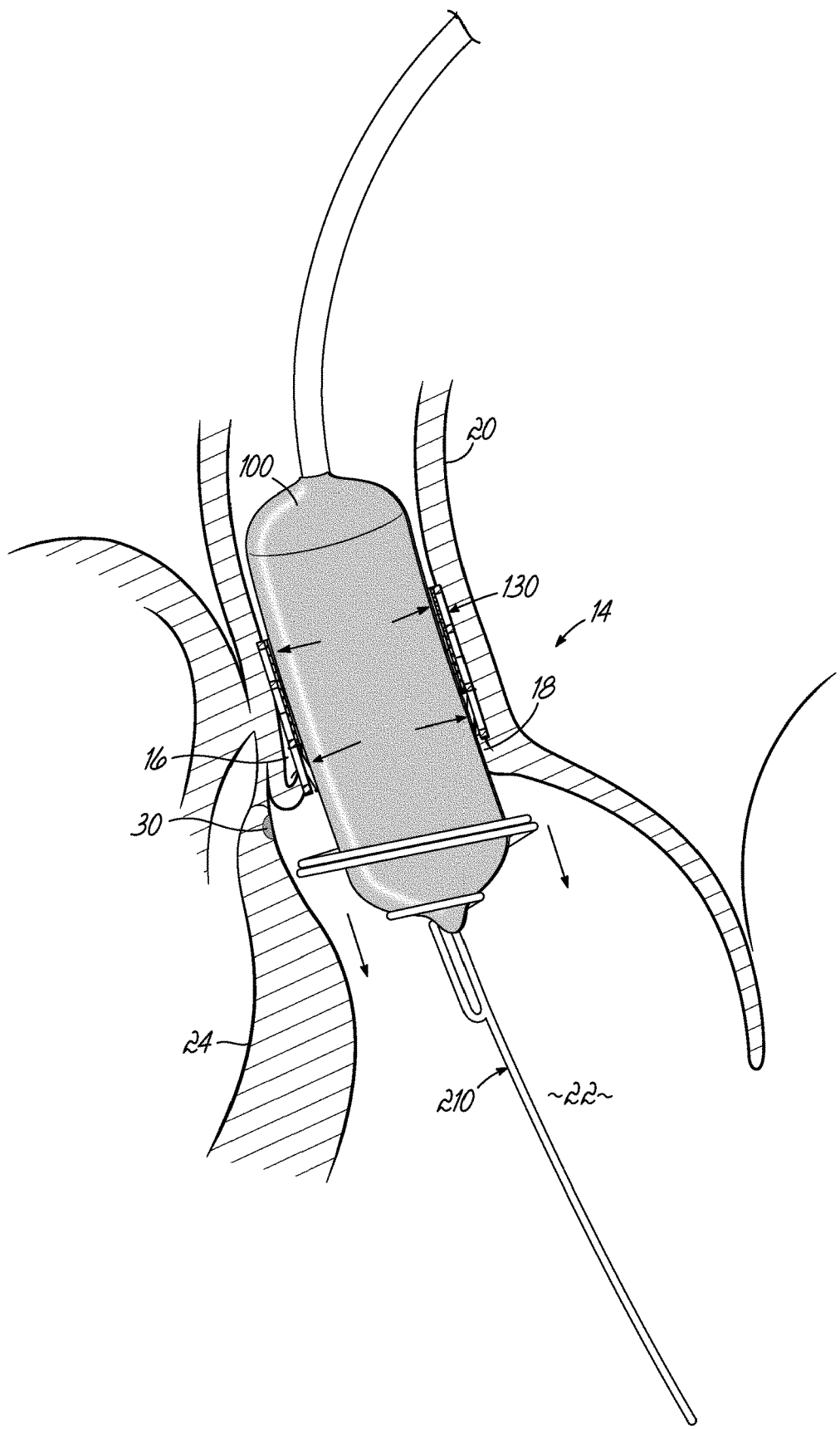

FIGS. 13A through 13C show a template or guide device 210 that integrates a distal guide wire with a valve positioning guide. It can be inserted as described previously by placing a catheter in the left ventricle 22. The delivery system for the valve 130 can then be fed over the template 210 to position the valve 130.

As in the previous FIG. 12 series of drawings, the prosthetic valve 130 is moved into the inside of the native aortic valve 14 in an ideal location. As in FIG. 12B, the balloon 100 is inflated as shown in FIG. 13B. This moves the helix 210 away from the lower end of the valve 130.

The balloon 100 has been fully inflated as shown in FIG. 13C, and the valve 130 is in perfect position. The delivery system and the template 210 then can be removed from the patient.

Figure 14A:
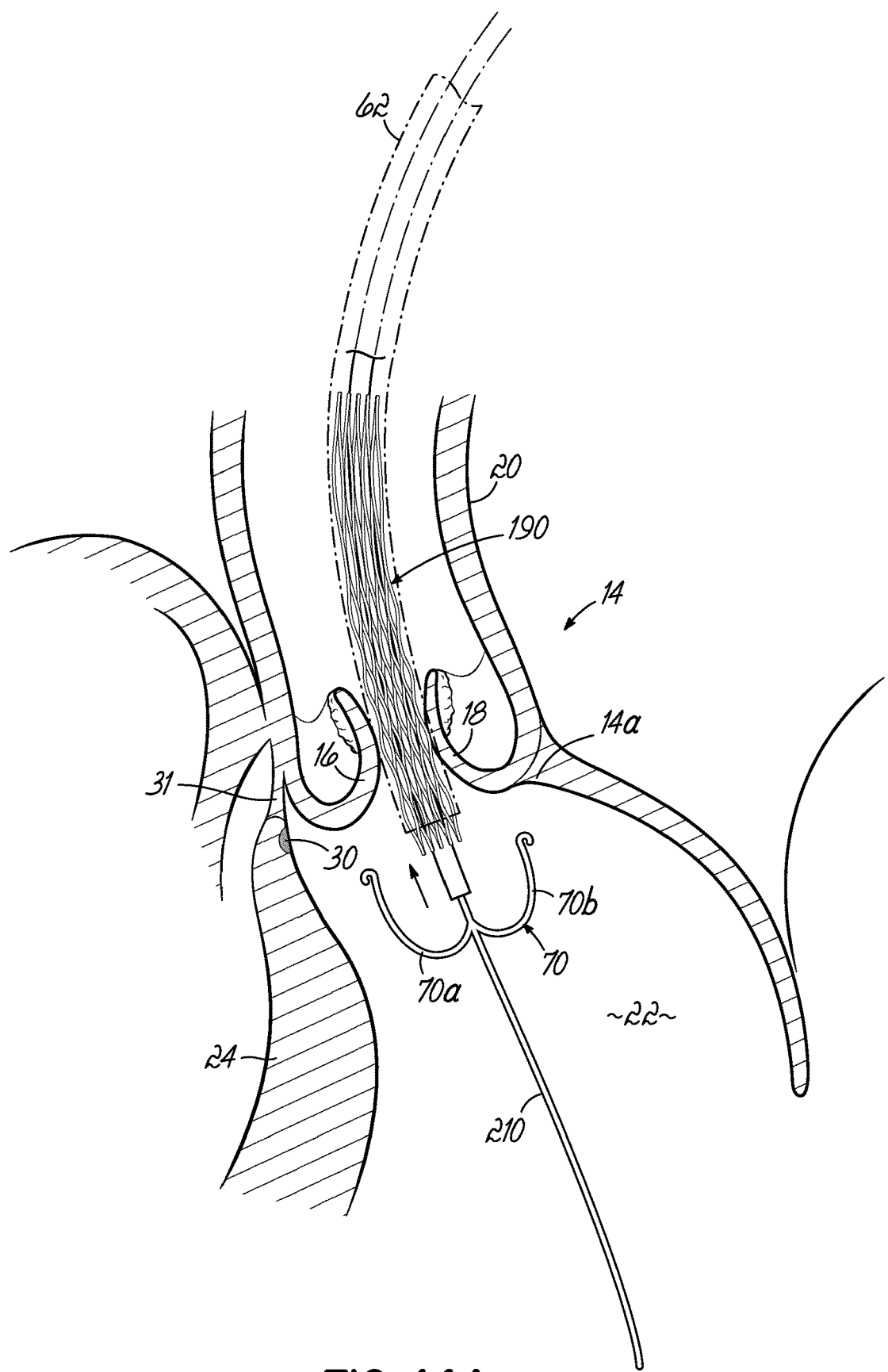
FIGS. 14A through 14C respectively illustrate another embodiment of the invention in the form of an integrated guide device and guide wire used for locating and implanting a prosthetic heart valve.
Figure 14B:
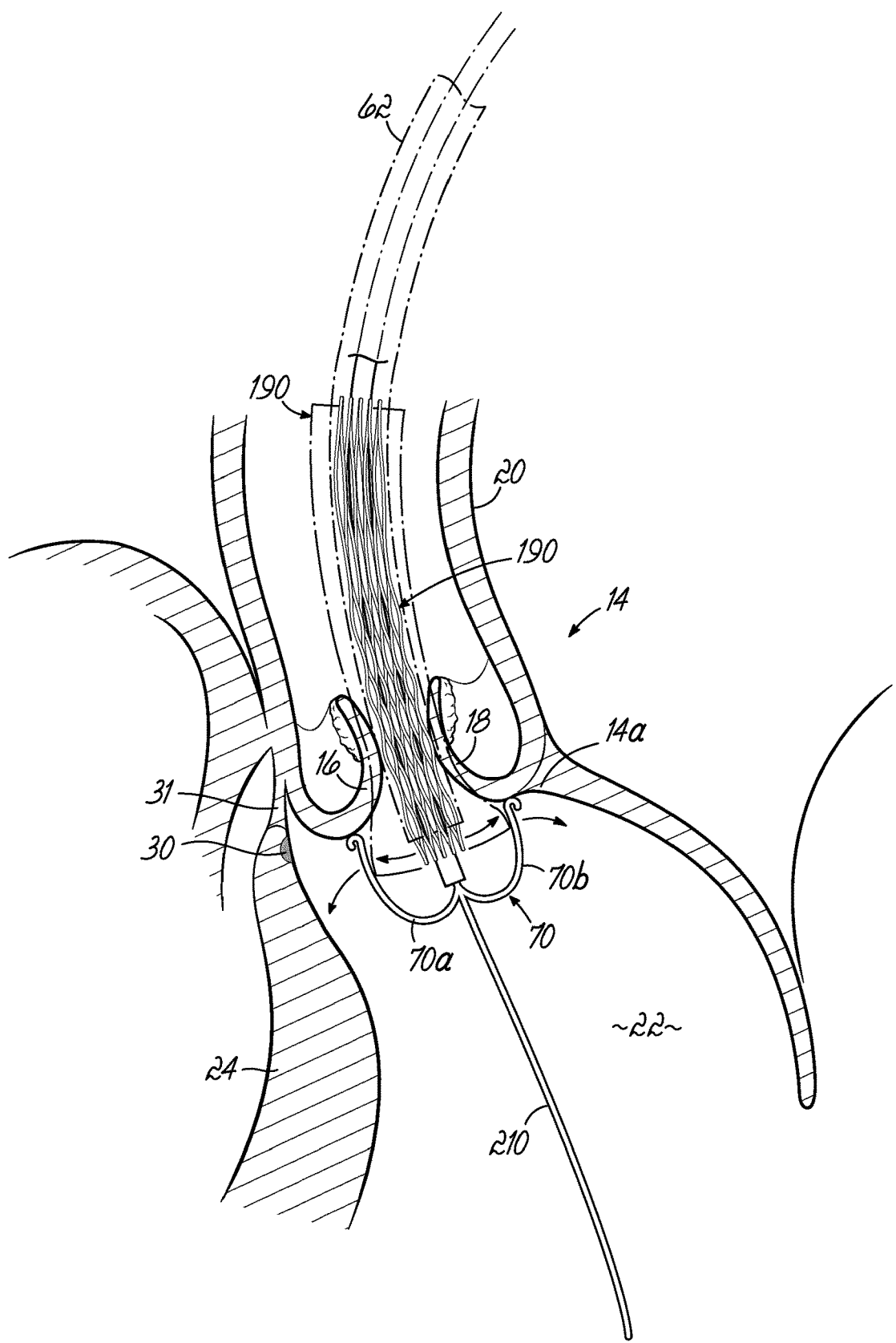
Figure 14C:
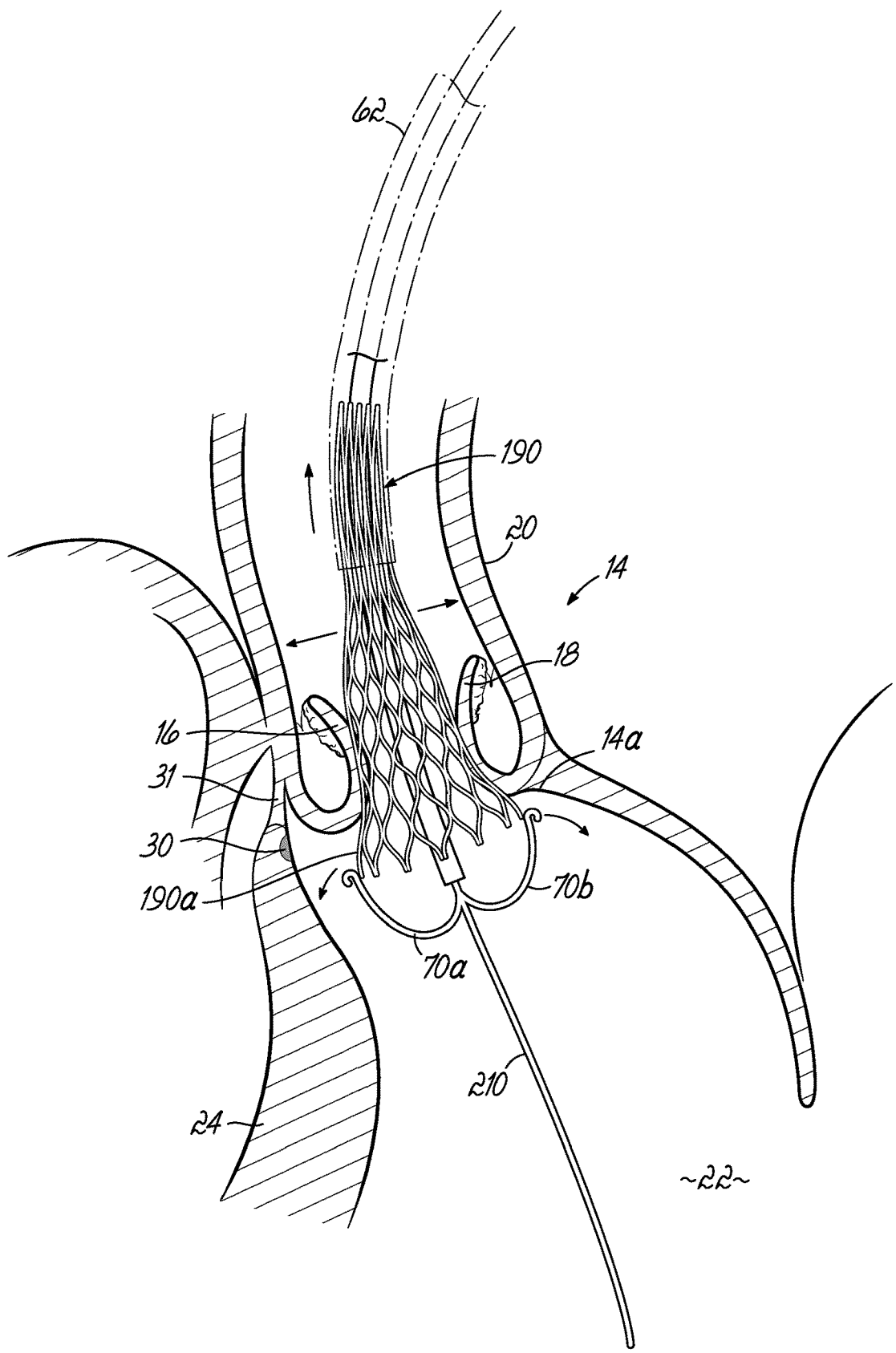

FIGS. 14A to 14C show a template or guide device 210 incorporating a guide wire with the template or positioning wire. As described previously, in clinical practice, there is usually a guide wire placed in the left ventricle 22 initially during a procedure.

In these figures the guide wire and the template positioning device are fused or integrated and have a fixed or otherwise unitary but functional relationship. It is also possible to slide the template guide over the guide wire. The central guide wire and the template could move independently. This would ensure that the guide wire does not cause an injury to the left ventricle 22—including rupture of the ventricle 22. Also, interventionists are highly experienced in manipulating guide wires to help their valve implant procedure. Allowing separate control of the template and the guide wire may be helpful.

To link the template guide to the guide wire, a relatively tight spiral of template could wrap around the guide wire. This would hold the two devices together and they could move independently. In this system there is no helix to center the system. A centering device is optional with the template or guide device that positions the level or height of the valve 190. The implant procedure is the same as described previously.

Figure 15:
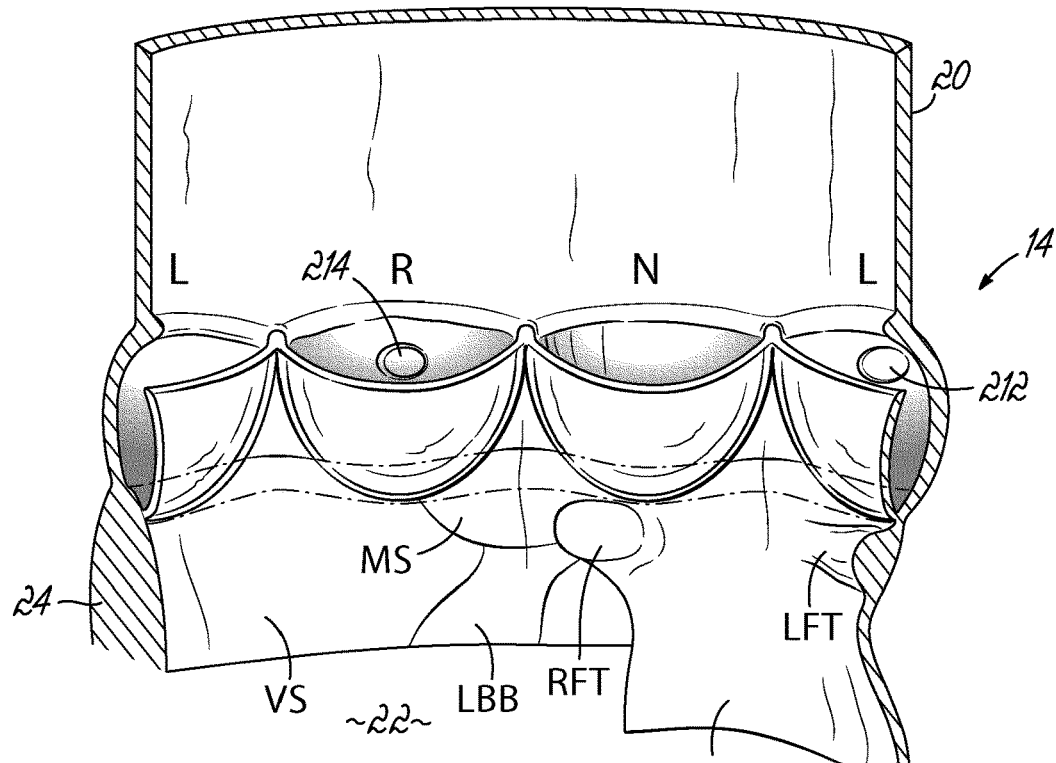
FIGS. 15 and 16 respectively show the anatomy of a native aortic valve and surrounding anatomical structure in a schematic form.
Figure 16:
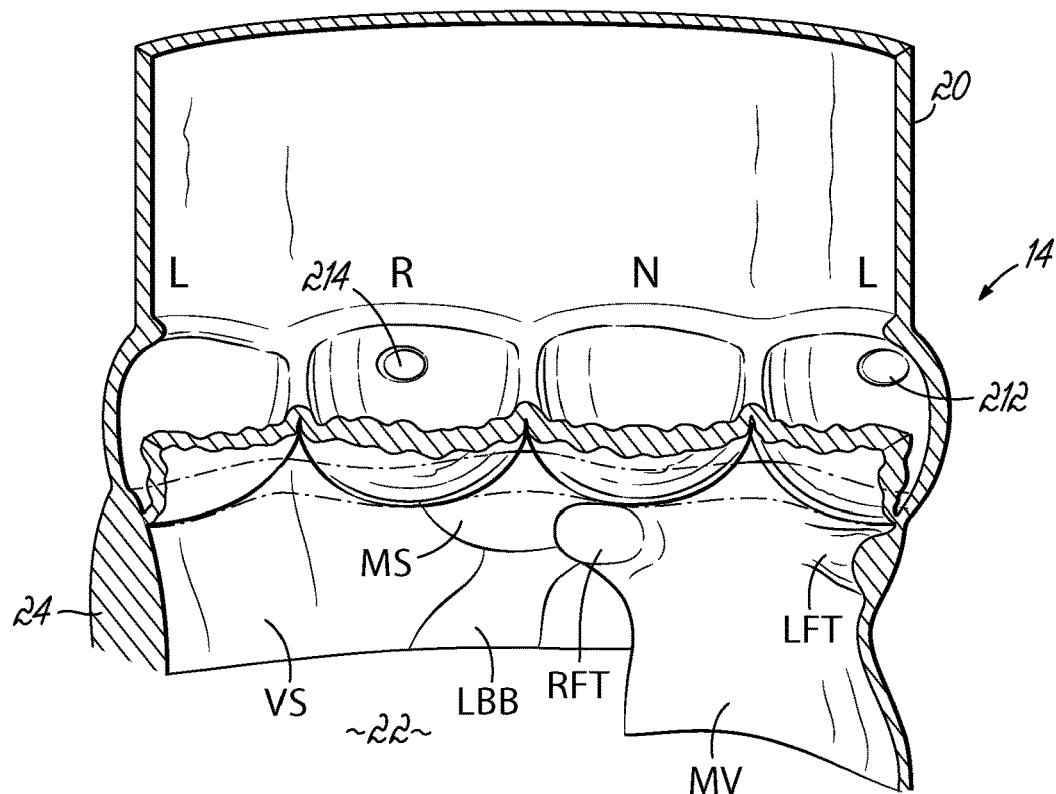

FIGS. 15 and 16 show the anatomy relevant to the development of heart block. The aorta 20 is longitudinally opened in illustrative form. The cusps of the aortic leaflets are shown under the letters L (left), R (right) and N (non-coronary cusp). The orifices of the left and right coronaries are shown as apertures 212, 214 in the aorta 20. Below the level of the aortic valve 14 is the ventricle 22. The ventricular septum (VS) is shown. This is muscular heart tissue. The mitral valve is marked as MV. The left and right fibrous trigones are marked as LFT and RFT.

The membranous septum (MS) is not composed of muscle, but a thin fibrous layer that separates the left and right ventricles. On the lower margin of the membranous septum, the conduction tissue is shown here as the left bundle branch (LBB) or conduction tissue 30. This is the tissue that carries the signal from the atrium to the ventricles to stimulate the ventricles to contract as previously described. This tissue is located just a few millimeters below the native aortic valve 14, so it is easy to see how it can be injured or otherwise disrupted by the frame of an implanted prosthetic valve. The frame of most prosthetic valves is composed of a metal stent such as stainless steel or Nitinol. Some prosthetic valves are mounted on a balloon inflatable stent and others self-expand. In any case it appears any prosthetic valve can injure the conduction tissue and cause heart block.

When a valve frame contacts the conduction tissue 30 the signal for the ventricles to contract can be stopped or disrupted. In this case the ventricle 22 does not receive the signal from the atrium to contract. The damage to conduction tissue 30 can be immediate. But it is often delayed some time. The onset of heart block or conduction damage can be quite unexpected.

Figure 17:
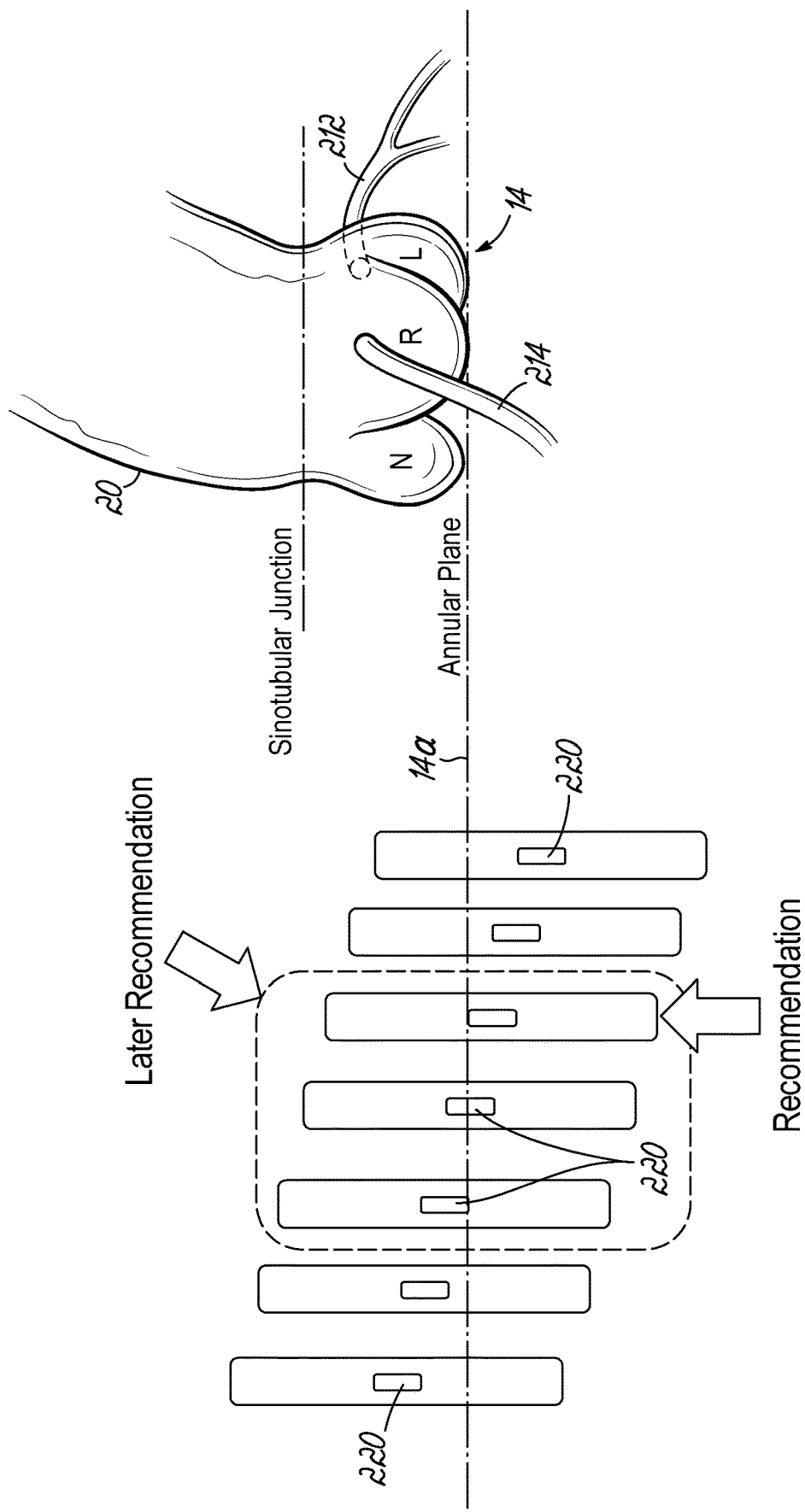
FIG. 17 schematically illustrates the plane of a native aortic valve and imaging process for use during an aortic valve prosthesis implantation.

Referring to FIG. 17, when an interventionist implants an aortic prosthetic valve, the most critical interest is in ensuring the valve is in a solid and secure position. The natural tendency is to place the valve quite low—so that a considerable part is located in the left ventricle. This ensures that when the heart beats, the newly implanted valve is not ejected out of the heart. Unfortunately, if the valve is implanted low, there is a greater risk of damage to the conduction tissue. FIG. 17 shows the current recommendations for valve placement when a balloon inflatable stainless steel valve is placed such as the Edwards Sapien 3 valve. The figure shows the annular plane (i.e., plane of annulus 14a) as a line along the lowest point of the aortic valve cusps. A marker 220 is located in the center of the unexpanded valve. Earlier, valve implantation was performed at a lower plane. It has recently been found that keeping the lowest part of the prosthetic valve less than 4 to 5 mm below the lowest point of the native aortic valve is almost never associated with heart block development. To accurately place the valve and avoid heart block, the central marker 220 is now positioned closer to the annular plane. This has resulted in a much lower incidence of heart block. But heart block has not been eliminated. And this position may not be ideal for the valve. The prosthetic valve may function better when positioned or located at a lower level.

Figure 18A:
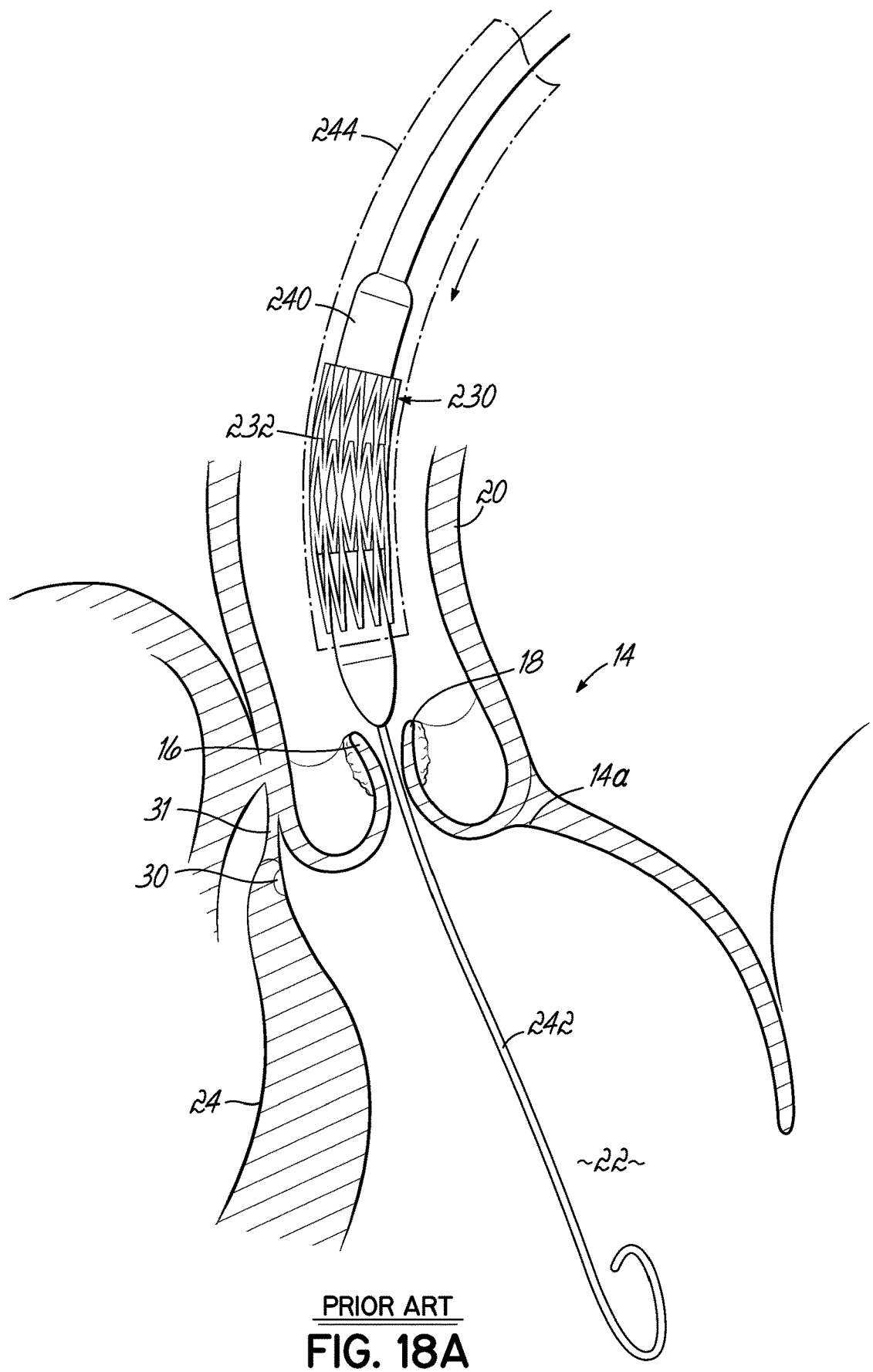
FIGS. 18A through 18C illustrate a method of inserting an expandable prosthetic stent valve into the native aortic valve and implanting the prosthetic valve in accordance with a prior art method.
Figure 18B:
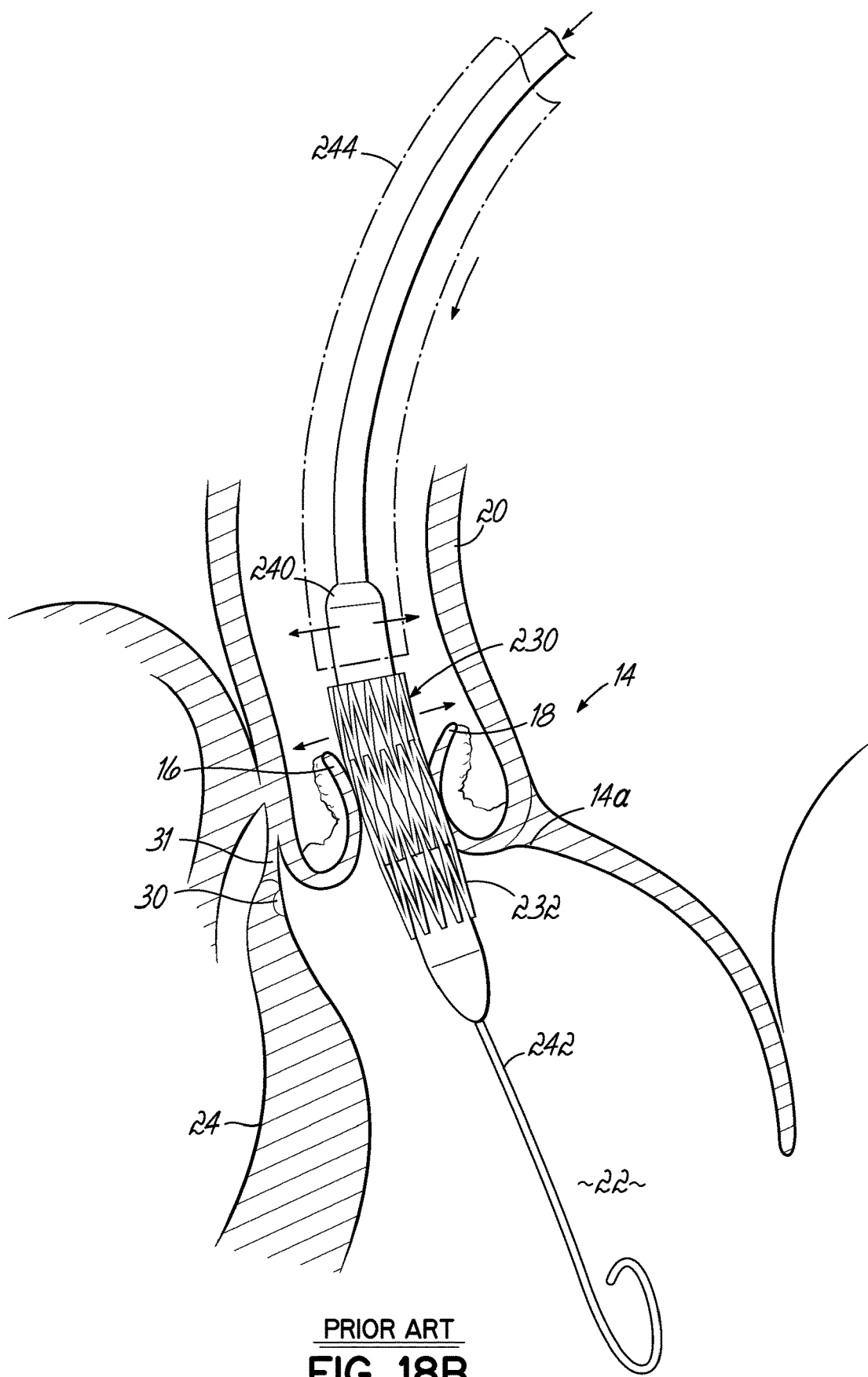
Figure 18C:
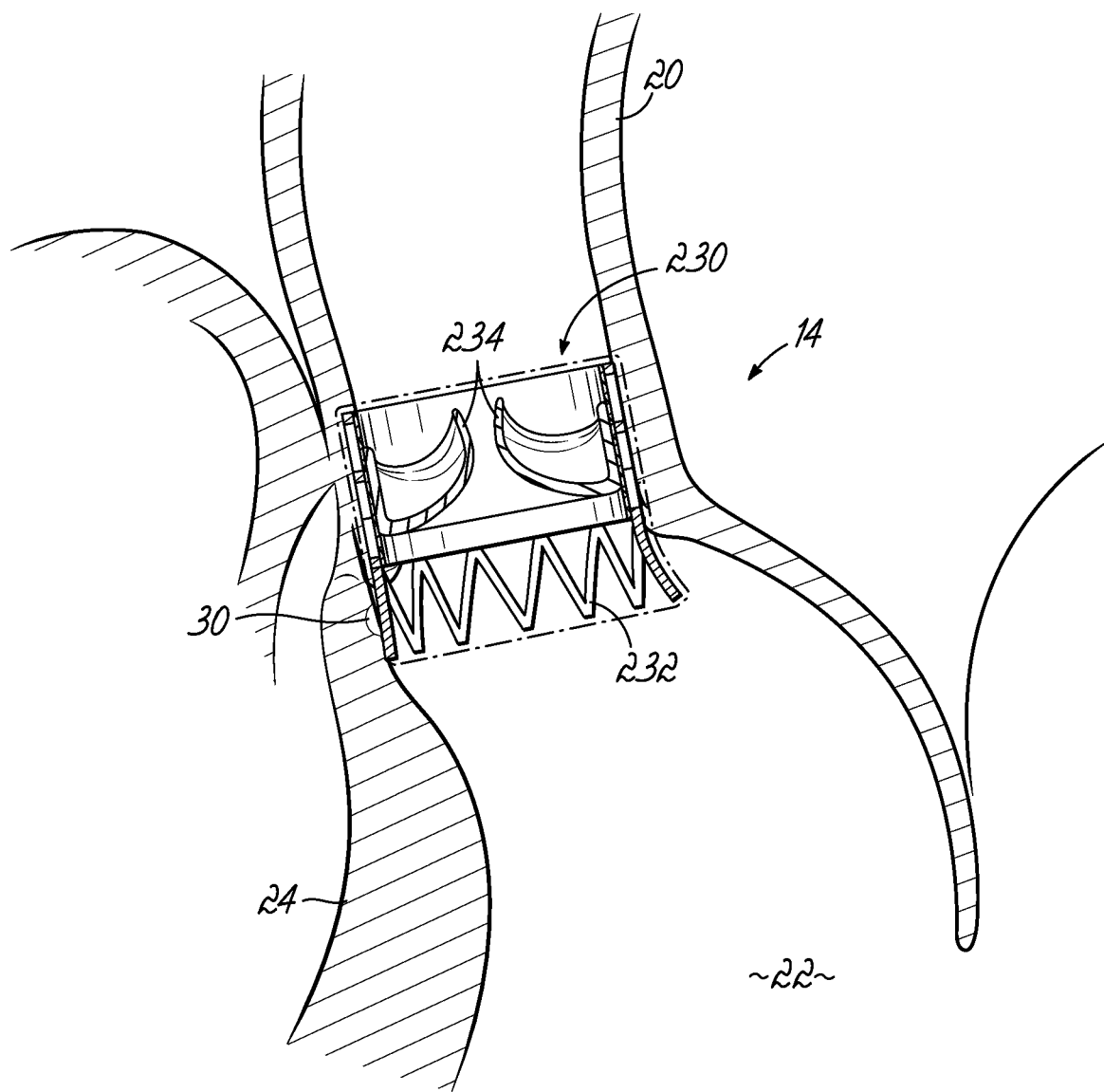

FIGS. 18A through 18C are labelled as "prior art." FIG. 18A shows a balloon expandable aortic valve prosthesis 230 similar to the Edwards Sapien 3 system. A stent portions 232 contains valve leaflets 234 and this has been crimped on a balloon 240 for delivery. A guide wire 242 is shown passing from the aorta 20 into the left ventricle 22. There is a central channel in the catheter 244 that mounts the prosthetic valve 230. The valve 230 is being guided over the guide wire 242 from the entry site in the groin toward the native aortic valve 14. The conduction tissue 30 is located below the native valve 14.

In FIG. 18B, the prosthetic valve 230 has been moved inside the native aortic valve 14. The balloon 240 will be inflated to expand the prosthetic valve 230 to secure it inside the native valve 14.

In FIG. 18C, the prosthetic valve 230 has been expanded. The stent mounting the valve 230 is now expanded and the valve 230 is secured against dislodgement but the valve 230 is expanded against the conduction tissue 30. This patient is at risk for development of a conduction problem or disruption, or heart block.

While these figures show a balloon expandable stent valve 230, there are many prosthetic valves that are mounted on self-expanding stents, typically made from Nitinol (NiTi). The self-expanding valve can also impinge against the conduction tissue and cause heart conduction problems.

Figure 19A:
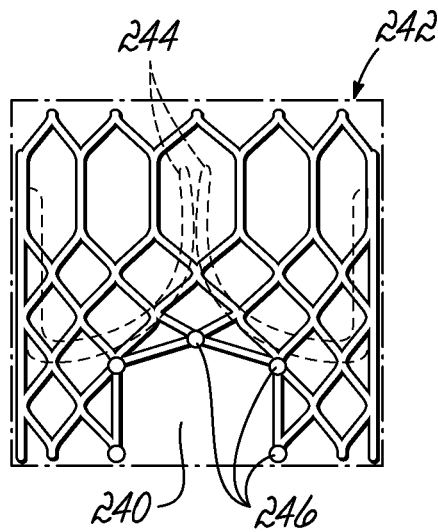
FIGS. 19A and 19B illustrate respective embodiments of an expandable stent valve having a cut-out, opening or recess for alignment with an avoidance of the conduction tissue within the heart.
Figure 19B:
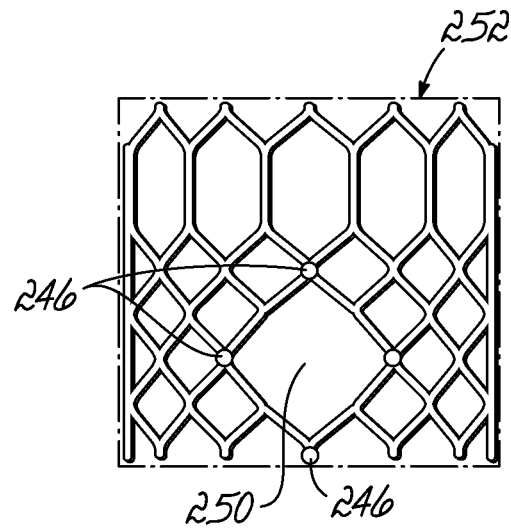
Figure 19C:
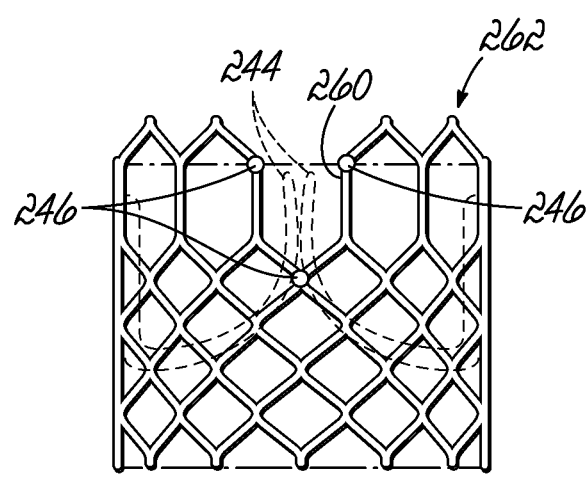
FIG. 19C is an elevational view similar to FIGS. 19A and 19B, but illustrating an expandable stent valve with a cut-out recess or opening for avoiding the coronary arteries.

Referring now to FIGS. 19A through 19C, it would be very useful to avoid the development of heart block also or alternatively by structural changes to a prosthetic valve. Despite a tremendous amount of work to develop markers and indicators to help physicians properly locate or position prosthetic valves delivered to an implant site via catheter, heart block unfortunately still occurs commonly—probably in at least 10% of treated patients.

As discussed, it appears that heart block occurs when a portion of the stent engages and compresses against the conduction tissue 30. The expanded stent valve or other expandable valve applies a very powerful force. It is not surprising this sensitive tissue is injured.

One alternative to avoid the development of heart block is to change the structure of the stent or the frame of the valve (even if composed of something other than a stent). For example, as discussed, some prosthetic valves are mounted on inflatable structures which can also be physically design altered to prevent contact with the conduction tissue.

FIGS. 19A, 19B, and 19C show stents associated with valves and having variations that will allow the conduction tissue to avoid injury. FIG. 19A shows a single "cut-out," recess or opening 240 along the lower border of a stent valve 242 so that the valve 242 can be placed with the "cut-out" opening 240 aligning with the region of the conduction tissue. Specifically, this cut-out, opening or recess 240 is located along the lower edge/margin or circumference of the prosthetic valve 242 and in various embodiments and may create a discontinuity such that the lower edge is asymmetrical about a plane that bisects the prosthetic valve 242 at a location other than at the cut-out, opening or recess 240. The cut-out, opening or recess 240 must also be located below the area of the prosthetic valve leaflets 244 or other valve component that seals with the adjoining native tissue. As such, the doctor can implant the prosthetic valve 242 at an optimal location within the native aortic valve 14 and along the longitudinal axes of the native and prosthetic valves 14, 242 and then rotate the prosthetic valve 242 so that the cut-out, opening or recess 240 aligns with the conductive tissue 30. In this way, no portion of the prosthetic valve 242 should apply undesirable forces against the conduction tissue 30.

FIG. 19B shows another variation. A single enclosed opening 250 is shown in the stent frame 252. As per the description above, this opening 250 is located on the stent frame 252 and the prosthetic valve will be implanted so that the opening 250 is adjacent to and in alignment with the conduction tissue 30. In this manner, no portion of the prosthetic valve frame 252 or any other prosthetic valve portion engages and disrupts or damages the conductive tissue 30.

The opening or recess 250 in the stent structure 252 of the prosthetic valve can be of any shape or configuration that helps to avoid contact and injury to the conduction tissue 30.

It should be noted that the change in the design of the stent frame 252 may impact the strength of the frame 252 or its ability to correctly mount the leaflets 244. The stent design can be modified to accommodate for the loss of the complete circumferential shape of the stent 252 at the level of the "cut-out," opening 250 or other configuration of recess meant to avoid contact with the conductive tissue.

FIG. 19C shows a "cut-out," recess or opening 260 at the upper margin of a stent frame 262. Sometimes the upper part of the stent valve 262 pushes against native leaflet tissue and impairs flow to the coronary arteries. A variety of such cut-outs, recesses or openings 260 could be used on the upper margin of the stent 262 to avoid impairment of flow to the coronary arteries. When the flow to the left main coronary artery is decreased by a stent pushing the left coronary cusp into the sinus of Valsalva behind the leaflet, the result can be lethal. A cut-out, recess or opening 260 of any shape in the upper part of the leaflet could prevent this problem. The concepts shown in FIGS. 19A and 19B could also be used in the upper part of the stent 262. These figures could be considered as candidates to solve this problem in an upside down position. Specifically, the locations of the upper cut-outs, recesses, or openings 260 are coordinated with the cut-out, opening or recess 250 used for avoiding contact with the conduction tissue 30. In this manner, when the cut-outs, openings or recesses 260 along the upper edge are aligned with the coronary openings, the cut-out, opening or recess 250 along the lower edge will automatically align with the conductive tissue 30. In this manner, contact between the stent valve 252, 262 and both the coronary arteries and the conductive tissue 30 will be avoided.

Figure 19D:
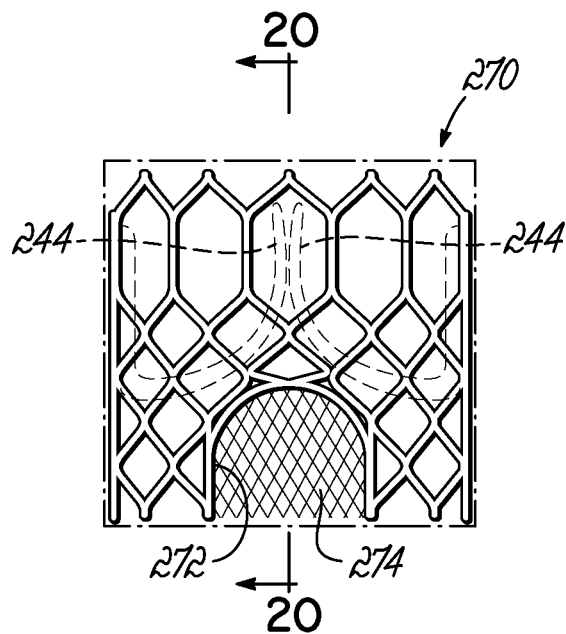
FIG. 19D is an illustration similar to FIG. 19A, but illustrating the opening covered with a mesh material for creating a mesh covered recess.

FIG. 19D shows a stent valve 270 with an opening or cut-out 272 on its lower margin or edge. It may be useful to cover the opening or cut-out 272 in the stent frame 270 with a mesh 274 that is indented to avoid contact with the conduction tissue 30. The mesh or other material 274 may bow or otherwise extend inwardly toward the central longitudinal axis of the stent valve 270 in order to avoid contact with the conduction tissue 30. The mesh 274 could be made from metal or from fabric or any other material.

It may be useful to develop a stent valve 270 that is fabricated with a pre-formed indentation 272. The indentation 272 would be oriented to extend toward the inside of the stent valve 270 as described above and shown in the drawing so that the stent 270 could be placed with a portion designed to avoid the conduction tissue 30. In this instance, a structurally complete valve frame may be formed in these instances and the shape chosen to be structurally more sound.

The leaflets 244 are mounted inside the valve stent 270. Their shape and attachment may need modification to adapt them to a modified frame from the currently used fashion. Although not shown or described in the embodiments of the FIG. 19 drawing series, any desired covering material may be used, such as in the manners described in connection with FIGS. 23B and 24B, below or other manners.

Figure 20:
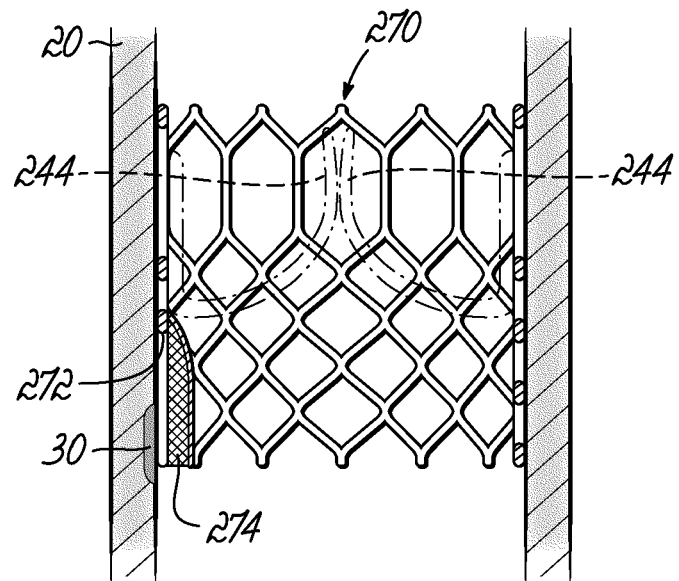
FIG. 20 is a cross sectional view taken along line 20-20 of FIG. 19, and illustrating the prosthetic stent valve schematically placed at the location of the native aortic valve with the mesh covered recess in alignment with the conduction tissue.

FIG. 20 shows a valve 270 shown in FIG. 19D from a side cross sectional view. A Nitinol stent could be set with a pre-formed indentation 272 so that there would be a complete stent with an indentation (no structural defect but instead a "dimple") without the need for a separate mesh cover.

Stent valves in these figures are generally shown stripped of their fabric covers, for clarity. Many stents have fabric or plastic covers on their surface. These covers could be used in conjunction with these stent designs. A stent valve could have a cut-out, opening or recess in the frame and have a fabric covering the cut-out, opening or recess overlying the conduction tissue. So the valve would be complete and would not be expected to cause a conduction abnormality.

Figure 21:
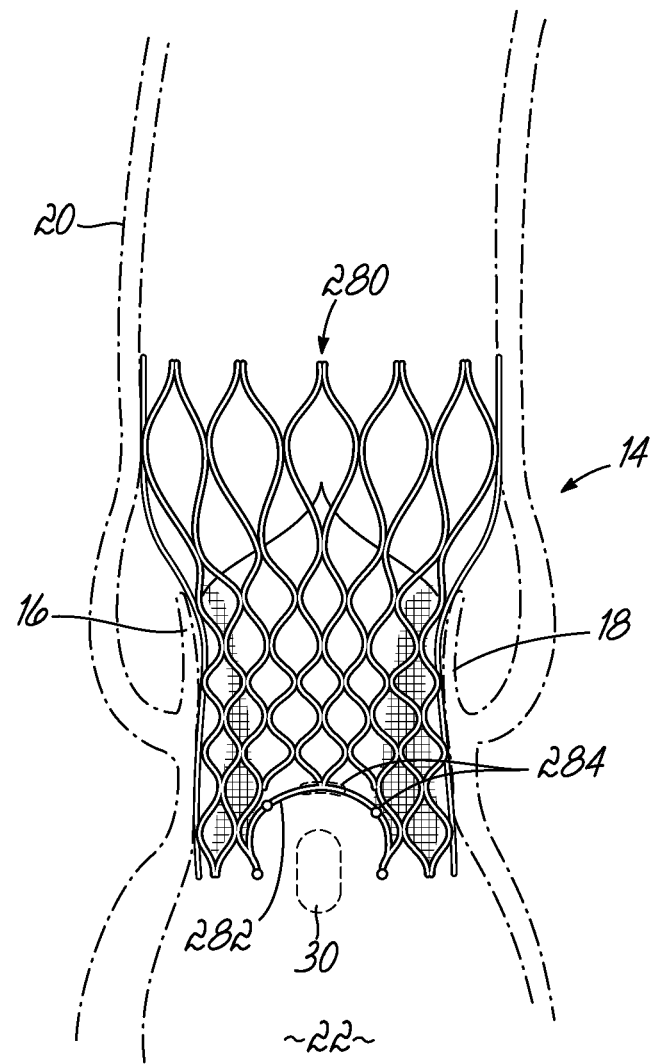
FIG. 21 is a schematic view illustrating another embodiment of a stent valve having an opening, recess or cut-out in alignment with the conduction tissue.

FIG. 21 shows a self-expanding Nitinol stent valve 280 similar to a valve sold by Medtronic. At the lowest margin or edge of the stent valve 280, there is an upside down U-shaped cut-out, opening or recess 282. This cut-out, opening or recess is shown avoiding the conduction tissue.

As described previously, the cut-out, opening or recess 282 in the stent frame could be covered by a layer of plastic or fabric (not shown). The plastic or fabric would not be expected to damage the conduction tissue 30.

The doctor implanting these valves with cut-outs, openings or recesses in the frame will need to rotate the implanted valve to ensure that the expanded valve is correctly oriented so that the cut-out, opening or recess 282 is directed toward (i.e., in alignment) the conduction tissue 30. Fluoroscopy, echocardiography and other techniques may help this identification. Additional markers and guide wires could be placed on the valve delivery system or stent of the valve 280 to help with orientation.

FIG. 21 shows a prosthetic heart valve stent 280 with a U-shaped cut-out, opening or recess 282 in the inflow portion of the valve 280. The cut-out, opening or recess 282 is designed to avoid contact between the valve frame and the conduction tissue 30.

To facilitate implantation, markers (such as radiopaque markers) could be placed on a delivery catheter 284 or on the prosthetic valve 280 to help locate the cut-out, opening or recess 282 in the valve frame and orient it correctly with the heart tissue, that is, in alignment with the conduction tissue 30.

For example, the upside down U-shaped opening at the valve inflow (that is, on the lower circumferential edge or border) could have markers placed around the perimeter of the cut-out, opening or recess 282. Or markers could be placed just at the ends of the upside down U-shaped cut-out, opening or recess 282 to allow easy identification of the margins of the cut-out, opening or recess 282. These markers 284 could then be aligned so that the cut-out, opening or recess 282 at the inflow end of the prosthetic valve 280 could be oriented to overlie the conduction tissue 30. Additional markers could be placed on the prosthetic valve 280 or on the delivery catheter to help with placement. The conduction tissue 30 sits underneath the junction of the right and the non-coronary aortic valve cusp. The valve prosthesis 280 could be rotated and positioned so that the cut-out, opening or recess 282 sits at the junction of the non-coronary and right coronary cusps of the native aortic valve 14. During the procedure, the interventionist could partially deploy a prosthetic valve 280 such as a self-expanding valve by extruding it from its sheath. The marker or markers could then be visualized against the native aortic valve 14. The prosthetic valve delivery system could be rotated and manipulated so that the cut-out, opening or recess 282 in the valve 280 is located in the region of the conduction tissue 30. Ultrasonic guidance may help with identifying the valve leaflets.

The markers 284 could also be placed on the delivery sheath. For example, the valve 280 could be loaded so that the cut-out, opening or recess 282 was oriented beneath a marker on the delivery sheath or delivery catheter. The delivery catheter could be rotated so the valve inside the sheath was oriented such that the cut-out, opening or recess 282 in the valve 280 is oriented to the conduction tissue 30.

It would also be possible to use markers (not shown) on the prosthetic valve 280 and on the delivery system. This combination may provide the greatest certainty for appropriate delivery.

To orient the markers on the prosthetic valve 280 or the delivery system there are many options. One option would be to identify the right coronary artery. The conduction tissue 30 is located under the junction of the right and non-coronary cusps of the native aortic valve 14. By locating the right coronary the valve markers can be rotated with respect to this location to correctly position the prosthetic valve 280. Also, many patients undergo a CT scan prior to a valve procedure. The CT can be used to precisely identify the anatomy in the region of the native valve 14. For example, CT images can be generated that identify the location of the conduction tissue 30. The plane associated with these images can then be replicated during the procedure (positioning of the patient and the fluoroscopy camera) allowing the interventionist precise knowledge of the position of the conduction tissue 30.

It should be noted that the shape of the cut-out, opening or recess 282 is shown as a U. The shape could vary. It could be V-shaped for example. Also, it could have a more square shape. The depth (or "length" when measured in the direction of blood flow) of the cut-out, opening or recess 282 could be shallower or deeper (shorter or longer). The important point is to reduce the risk of tissue injury by a prosthetic valve frame. Any design that keeps the prosthetic valve 280 from engaging against the tissue 30 will be useful.

The prosthetic valve leaflets 244 can be arranged in any way that produces a seal inside the valve frame so that blood does not regurgitate inside the heart.

Also, prosthetic valves have covers (not shown) to promote sealing. The seals could have any relationship to underlying structure of the prosthetic valve 280 and the valve cut-out, opening or recess 282. The seal could cover the cut-out, opening or recess 282 or the cut-out, opening or recess 282 in the frame could be uncovered or partially covered.

Figure 22:
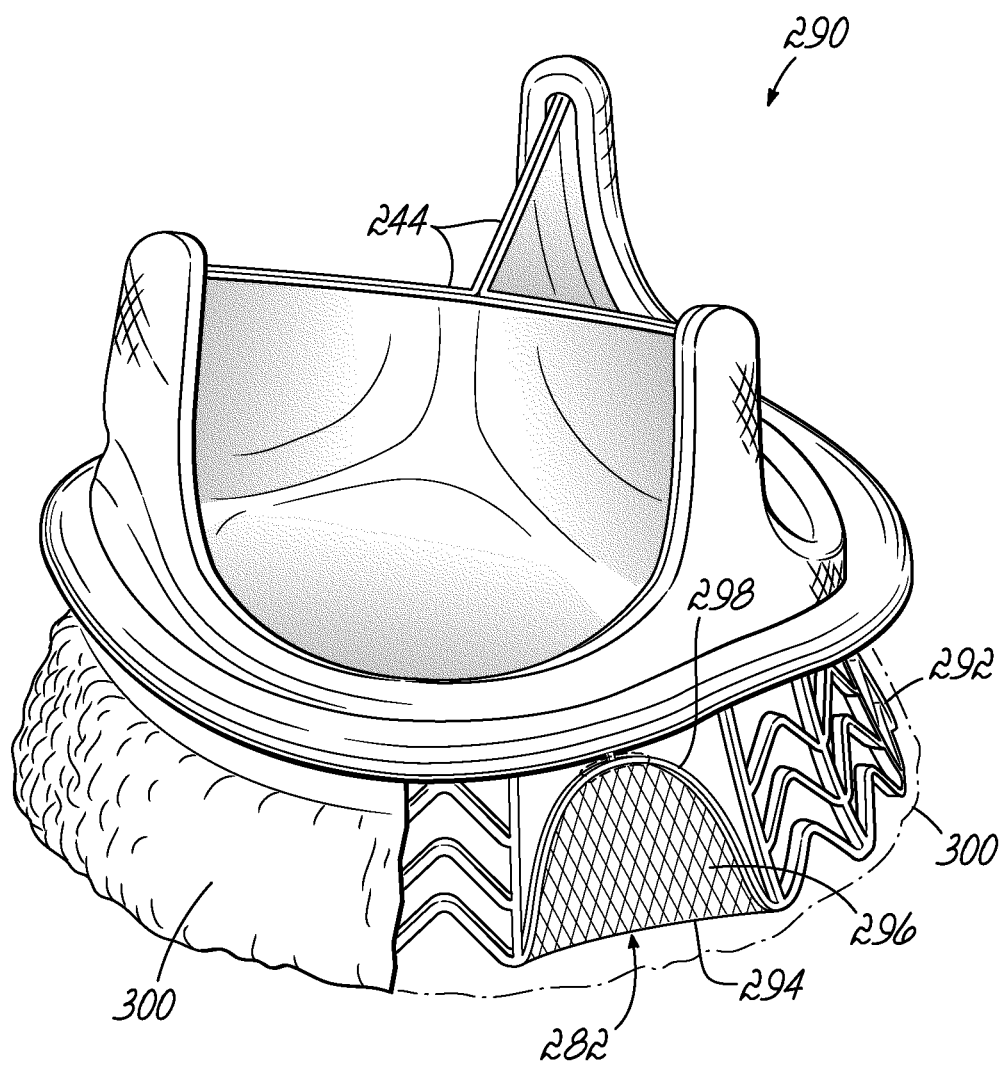
FIG. 22 is a perspective view illustrating another embodiment of a valve prosthesis including a mesh covered recess or opening for avoidance of any engagement with the conduction tissue.

Referring now to FIG. 22, Edwards also produces a surgical valve 290 that can be implanted without sutures known as Intuity. This valve has a mounting stent 292 to hold it in place rather than sutures. This is depicted in this figure. The mounting stent 292 could have a complete cut-out, opening or recess 282 such as the upside down U shape shown previously, that could be oriented to avoid contact with conduction tissue (such as in FIG. 21). In FIG. 22 an indentation 294 shown as a mesh element 296 attached to a U-shaped border area 298 is shown. This could be a separate and different material or this indented part can be formed as part of the stent 292 that sits underneath the valve leaflets 244. In addition, the arched or U-shaped border 298 may be coated or otherwise formed such that it acts as a radiopaque marker for allowing the doctor to visualize the cut-out, opening or recess 282 on fluoroscopy during the implant procedure.

The cut-out, opening or recess 294 in the frame could be covered by the fabric cover 300 shown over the rest of the valve. The perimeter of the valve 290 would provide a complete circumferential seal without the high pressure contact against the conduction tissue 30.

The indented part 294 would be oriented by the surgeon to be placed over the conduction tissue 30. Similarly, there could be a complete cut-out, opening or recess in the stent with no mesh that could be oriented over the conduction tissue 30 beneath the native leaflets. There could be a fabric cover or there could be no fabric cover over this region including the recess or indentation 294.

The surgeon can see the membranous septum during valve surgery so this valve 290 can be oriented to ensure the cut-out, opening or recess 294 is rotated into alignment with the conduction tissue 30. This area of the valve could be marked on the prosthetic valve 290 or its delivery system to clearly identify the correct implant orientation of the prosthetic valve 290. The surgeon could rotate and manipulate the valve by visual inspection to ensure the correct orientation of the cut-out, opening or recess 294 in the frame with the conduction tissue 30.

A common goal of these structures is to avoid undue force created by the mounting stent 292 against the native conduction tissue 30.

Where a patient has aortic stenosis, the native aortic valve leaflets are stiff and often calcified. Interestingly, there is often a large amount of calcified material that extends below the diseased valve that overlies and continues even below the membranous septum. Sometimes this creates a large ball like structure. A cut-out, opening or recess in a stent may prevent crushing this material into the conduction tissue. To ensure this material does not break off and embolize, it would be useful to have a fabric covering over the cut-out, opening or recess in the stent. This cover would contain this material and prevent it from breaking off.

Figure 23A:
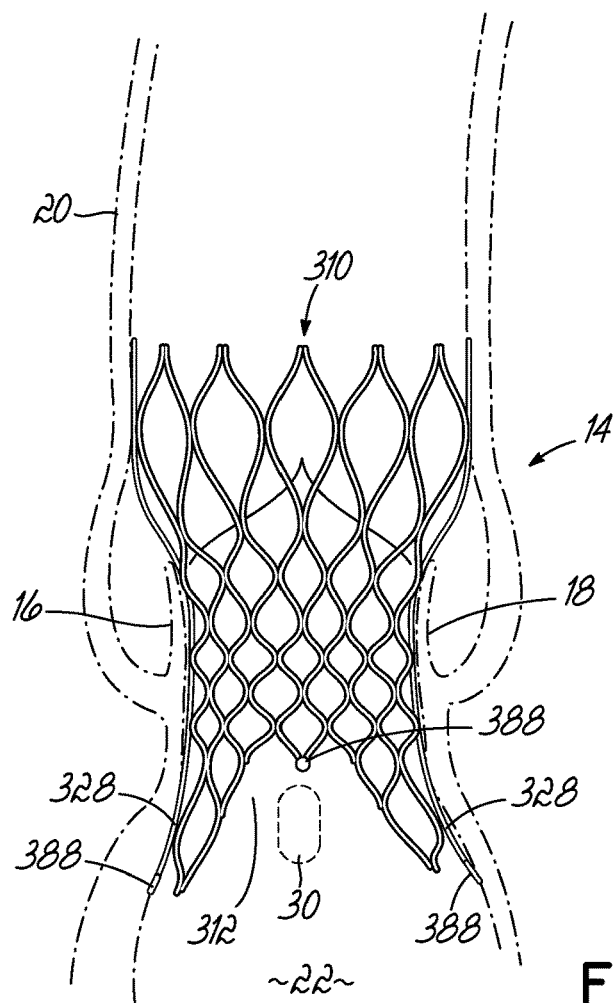
FIG. 23A is a schematic illustration of another embodiment of an expandable valve prosthesis at the location of the native aortic valve having a cut-out or opening in alignment with the conduction tissue.

FIG. 23A shows a self-expanding type of prosthetic aortic valve 310 with a cut-out, opening or recess 312. It should be noted that the inflow of the valve 310 sits inside the left ventricle 22 and it flares outward. This outward flare 314 serves to seal the prosthetic valve 310 against the heart tissue and to ensure that the prosthetic valve 310 is not forced out of position when the heart ejects blood. Current prosthetic valves have a continuous seal against the left ventricular outflow. A discontinuous inflow portion on the prosthetic heart valve 310 may flare more widely and provide a better seal. The cut-out, opening or recess 312 allows the expansion of the inflow of the valve 310 because it does not form a complete circle.

The cell construction of the prosthetic stent valve 310 can vary. Any useful pattern can be used in conjunction with a cut-out, opening or recess 312 in the valve inflow.

Figure 23B:
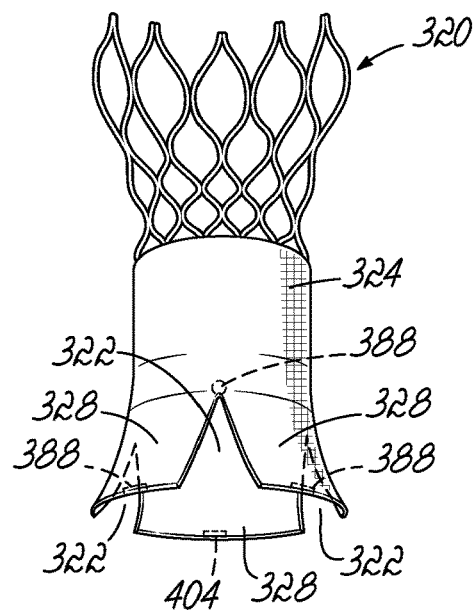
FIG. 23B is a view of the stent valve shown in FIG. 23A, but illustrating a fabric covering and three respective openings or cut-outs along the lower margin or edge of the stent valve.

FIG. 23B shows a prosthetic aortic valve 320 of the self-expanding variety with three V-shaped cut-outs, openings or recesses 322. As described previously, the cut-outs, openings or recesses 322 can take any shape. The edges of the inflow portion of the prosthetic valve, as shown in this figure, may be sharp. In clinical use it may be useful to have more rounded edges to prevent injury to the heart and to easy delivery. The valve 320 shown here has a fabric cover 324. The cover 324 can be arranged in any useful way over the valve frame. The cover 324 could also be incomplete. In other words, the cover 324 may not be on the entire underlying stent frame. Although covers are not shown on many of the embodiments shown and described herein, it will be appreciated that such covering material will be used on prosthetic heart valves such as these, as necessary or desired. The covering material may be in any conventional or desired construction, such as knit or woven fabrics that promote tissue in growth. Respective cut-outs in the covering 324 preferably coincide or align with the cut-outs 322. In this manner, when one of the cut-outs 322 is aligned with the conduction tissue 20, there is less chance of interference by any valve material with the signals travelling through the conduction tissue 30. Although three cut-outs 322 shown, a different number may be designed into the valve 320, and in this regard forming the valve 320 with only a single cut-out 322 has distinct advantages in that more of the valve surface area or covering material 324 is available for sealing blood flow after implantation. As an alternative, the covering material 324 may cover the cut-out 322 in the stent frame, on the outside of the frame, assuming it is found that this would not interfere with the conduction tissue. As mentioned, these concepts may be applied to any of the embodiments shown and described herein. The three cut-outs, openings or recesses 322 in the valve 320 are all shown with a similar shape. The cut-outs, openings or recesses 322 could be different. Some could be V-shaped and others U-shaped. Also the cut-outs, openings or recesses 322 could be at different depths. For example, there could be a more shallow outflaring of the prosthetic valve 320 near the conduction tissue 30. These edges of the inflow of the prosthetic valve 320 can be thought of as tabs 328. There could be more than three. There could be areas where there are no tabs 328—for example near the conduction tissue 30. There could be no prosthetic valve structure in the region of the conduction tissue 30 and tabs (a long single tab or multiple tabs) located around the rest of the perimeter of the inflow portion.

Figure 24A:
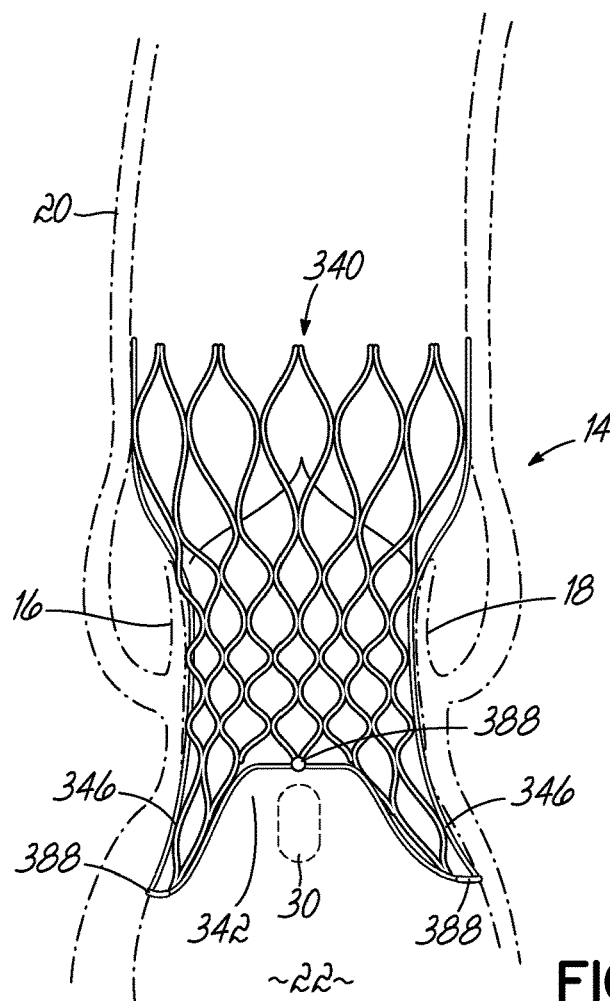
FIGS. 24A and 24B are views similar to FIGS. 23A and 23B, but respectively illustrating an alternative embodiment of an expandable stent valve having cut-outs or openings at the lower margin or edge.
Figure 24B:
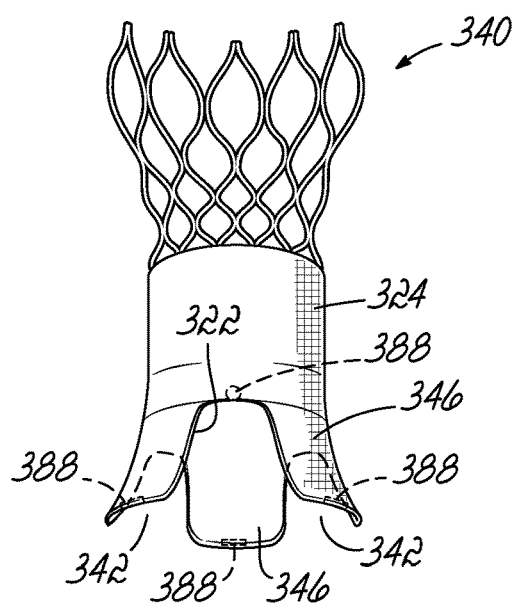

FIGS. 24A and 24B show an embodiment of a prosthetic aortic valve 340 with a discontinuous inflow portion or edge when viewed in the inflow plane.

There are three separate cut-outs, openings or recesses 342. This will allow the valve 340 to be easily rotated to avoid the conduction tissue 30. With only one cut-out, opening or recess 342 the amount of rotation necessary to align the cut-out, opening or recess 342 with the conduction tissue 30 could be considerable. However, this may be mitigated by implantation techniques that pre-orient the valve, for example, as described herein. The description of the embodiment in connection with FIG. 23B generally applies here with the difference being the shape or configuration of the valve 340.

Also, since the conduction tissue 30 is located beneath the junction of the right and non-coronary cusps of the native valve, this symmetric arrangement may be easier to align with the native aortic valve 14 to ensure good placement. The prosthetic valve 340 can be "matched" with the native valve 14.

"Tabs" or fingers/arms 346 are formed but could be much narrower than shown. These tabs 346 will provide good contact and flare against the outflow of the left ventricle 22 to keep the prosthetic valve 340 securely in place. The narrow "tabs" 346 will have a lower likelihood of contacting the conduction tissue 30. The tabs 346 could also be configured to "flare"—that is to extent out radially from the central axis of the valve 340 and contact the heart tissue in the outflow region of the left ventricle 22.

Many implanters prefer to use a self-expanding valve. This valve has the advantage that it can be extruded (at least partly) from its delivery sheath or delivery system, and if the position is not ideal, the valve can be re-sheathed and repositioned until it is in the correct position. Unfortunately, the risk of heart block is higher with a self-expanding valve. So an ideal situation for clinical practice would be a valve that is re-sheathable and repositionable while also carrying a low risk of heart block. A valve with tabs 346 could solve this problem.

Figure 25A:
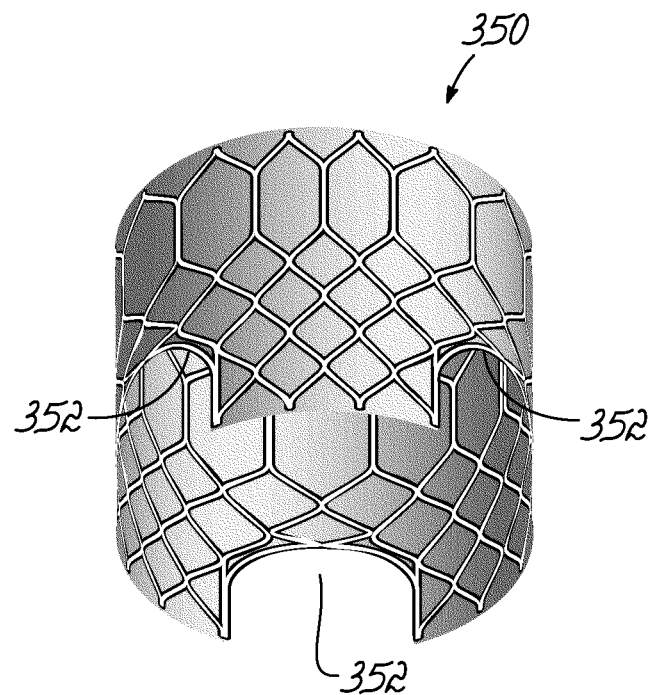
FIGS. 25A and 25B are respective views of a prosthetic stent valve including openings or cut-outs for avoiding the conduction tissue.
Figure 25B:
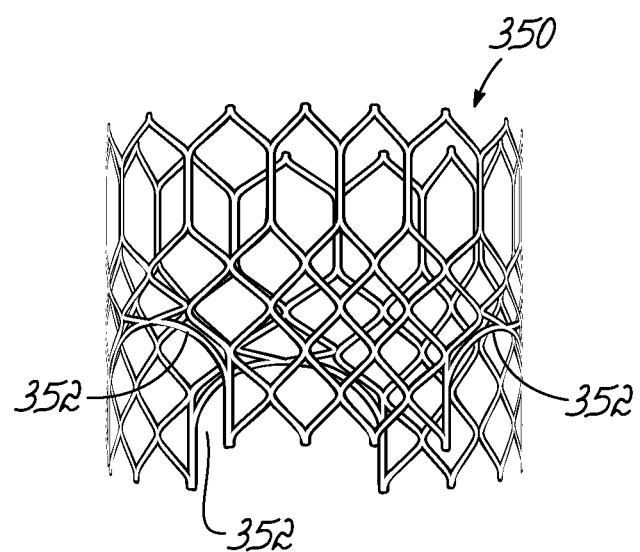

FIGS. 25A and 25B show a prosthetic valve 350 more typically made from stainless steel and expanded with a balloon. This valve 350 can also have the addition of multiple cut-outs or recesses 352. The valve 350 shown here has three cut-outs or recesses 352.

As described previously, there can be many arrangements with different shaped cut-outs, openings or recesses (U-shaped, V-shaped etc.) and different depths of tabs. The depths or lengths of the tabs on the same prosthetic valve could also vary. For example, tabs placed near the conduction tissue could be shallow (short). Other tabs could be longer for greater retention.

Figure 26A:
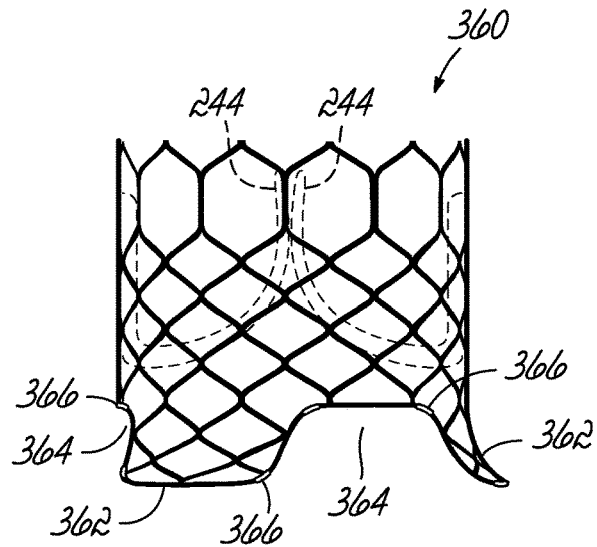
FIG. 26A is a schematic view of another embodiment showing an expandable stent valve with cut-outs and flared tabs or flanges between the cut-outs.

Referring to FIG. 26A, when a physician implants a prosthetic aortic valve, the first concern is that placement is too low—where the valve falls into the left ventricle 22 or too high—where the valve releases from the aortic position and can travel farther into the aorta 20. The risk of dislodgement into the aorta 20 is the biggest fear, so naturally, the strong tendency is to place the valve in a lower position. The lower position is, however, more likely to contact the conduction tissue 30.

FIG. 26A shows another prosthetic valve 360. The locations of the leaflets 244 are shown in the dotted lines. The valve 360 has an extension below the leaflets 244 that includes tabs 362 that sit inside the left ventricular outflow. These tabs flare out radially to conform to the left ventricular outflow tract. They can be flared by the expansion of a balloon that inflates the valve 360. Since the inflow of the valve 360 is discontinuous when viewed in the plane of the inflow, the balloon inflation will naturally result in flaring of the tabs 362. This will engage the valve 360 against the inside of the heart and keep it solidly in place. A self-expanding valve can also be formed in this way. The tabs 362 could be constructed to flare out after the valve 360 is delivered. By orienting the tabs 362 away from the conduction tissue 30, the risk of the conduction tissue 30 being injured is low.

Figure 26B:
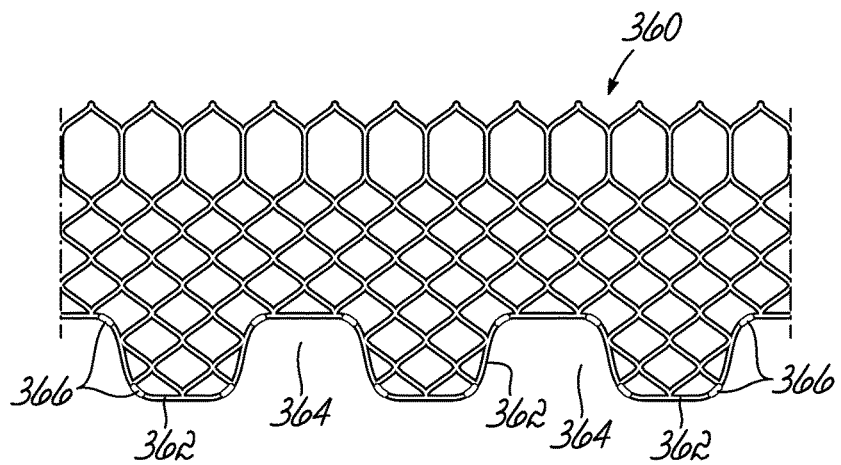
FIGS. 26B and 26C show respective alternative embodiments of an expandable prosthetic stent valve in a flattened or opened condition for clarity, and illustrating additional embodiments of tabs or flanges separated by respective cut-outs or gaps, in which the tabs or flanges may be used to better fix the stent valve in place within the heart, and one of the gaps may be aligned with the conduction tissue.
Figure 26C:
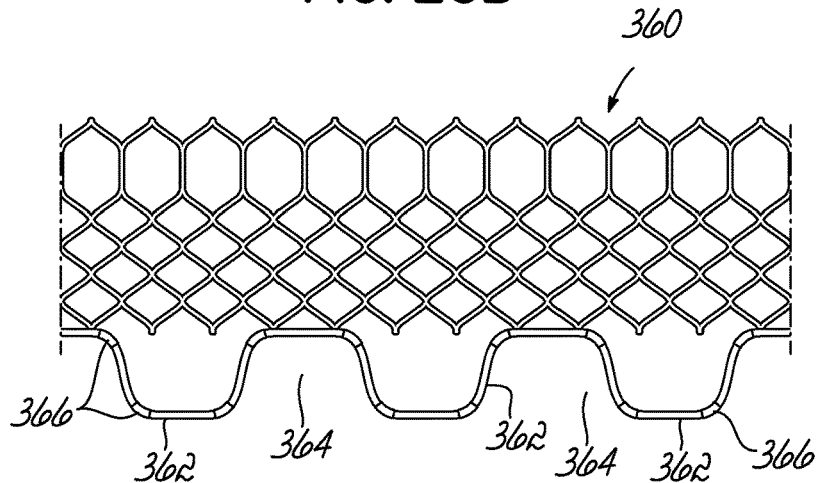

FIGS. 26A-26C show three tabs 362. There could be more or fewer. The tabs 362 could be wider or narrower. The tabs 362 are shown symmetric. They could be asymmetric. There could also be gaps between the tabs 362—especially to accommodate placement in the region of the conduction tissue. When this valve 360 is expanded, the implanter will feel a strong sense of security that the prosthetic valve 360 is in good position, stable and with low risk of ejection from the heart as well as confidence that the conduction tissue 30 will be free from injury. All of these tab concepts can be applied to any type of valve including self-expanding (Nitinol type) and balloon expanding (stainless steel). And, as with all embodiments and features disclosed herein, the various features may be used alone or in any combination depending on the desired results and functions. Another variation on a tab is to have a tab that is almost circumferential with only a gap in one area of the valve. The large tab would extend almost circumferentially around the valve.

FIG. 26A shows the valve leaflets 244 (dotted) and tabs 362 which function as extensions below the inflow of the valve 360. The leaflets 244 of the prosthetic valve 360 sit above the tabs 362. The leaflets 244 sit inside the tubular part of the valve 360. This means that the relationship between the leaflets 244 and the stent support is constant and largely independent of the added tabs 362. This may be a very useful arrangement. The current prosthetic valve design for both a self-expanding and a balloon inflated valve would not be seriously impacted by the addition of tabs 362. The mechanical stability and the way the leaflets 244 are supported by the stent would not be materially changed. It is likely that durability testing would not change and so there would be less expense in re-designing a new valve with these tab extensions. This is a long and costly endeavor requiring extensive engineering modeling and bench testing for stress and strain on the valve and finally animal durability testing and human testing. Adding tabs 362 should not require considerable additional testing. Also, one of the main costs for introducing a new valve concern the regulatory requirements from governments to allow use in patients. The fact the valve 360 in these figures functions like previous valves should reduce the cost of satisfying regulators before initiating sales of a device. Manufacturers can rely largely on their extensive experience with current valves to satisfy regulators.

FIG. 26A shows leaflets 244 that are sitting above the tabs 362. It would also be possible to position the leaflets 244 such that the cusps of the leaflets 244 follow the curved lower surface of the inflow on the prosthetic valve 360—the scalloped shape. The leaflets 244 could be positioned lower than shown in the figures. This would allow the implantation of larger cusps and also allow placement of a valve with a closure point even below the closing point of a natural aortic valve. The prosthetic valve leaflets 244 could sit lower inside the stent frame—along the flared part of the prosthetic valve 360. The valve diameter is larger in the flared part of the valve 360. The prosthetic valve area would be larger, reducing the gradient to flow out of the heart. In patients with very small outflow regions in the heart, positioning of a valve 360 may cause serious obstruction to blood outflow and this causes increased load on the heart. Placing the valve lower—even inside the left ventricle 22 where there is more space, may reduce the amount of obstruction to the outflow of blood from the ventricle. Currently, there is no possibility of subannular placement of prosthetic heart valves in the aortic position. In some patients there is a risk of obstruction of the coronary arteries with prosthetic valve placement. Lower placement of the prosthetic valve may be important in these patients.

FIGS. 26B and 26C show valve 360 with tab extensions 362. The valve 360 has been opened for easy viewing. This is shown only as an example. The stent cell pattern can be in any useful pattern. The key is that there is a single or multiple cut-outs, openings or recesses 364 to avoid contact with the conduction tissue 30. A self-expanding stent valve could also benefit from these features. Radiopaque markers 366 line the gaps 364 so that the doctor can more easily visualize correct positioning under fluoroscopy, especially aligning one of the gaps 364 with the conduction tissue. It will be appreciated that any of the prosthetic valves described herein as including a cut-out, opening or recess (i.e., a gap) may likewise include at least one radiopaque marker adjacent the cut-out, opening or recess for visualization and positioning purposes during the implantation procedure.

Figure 27:
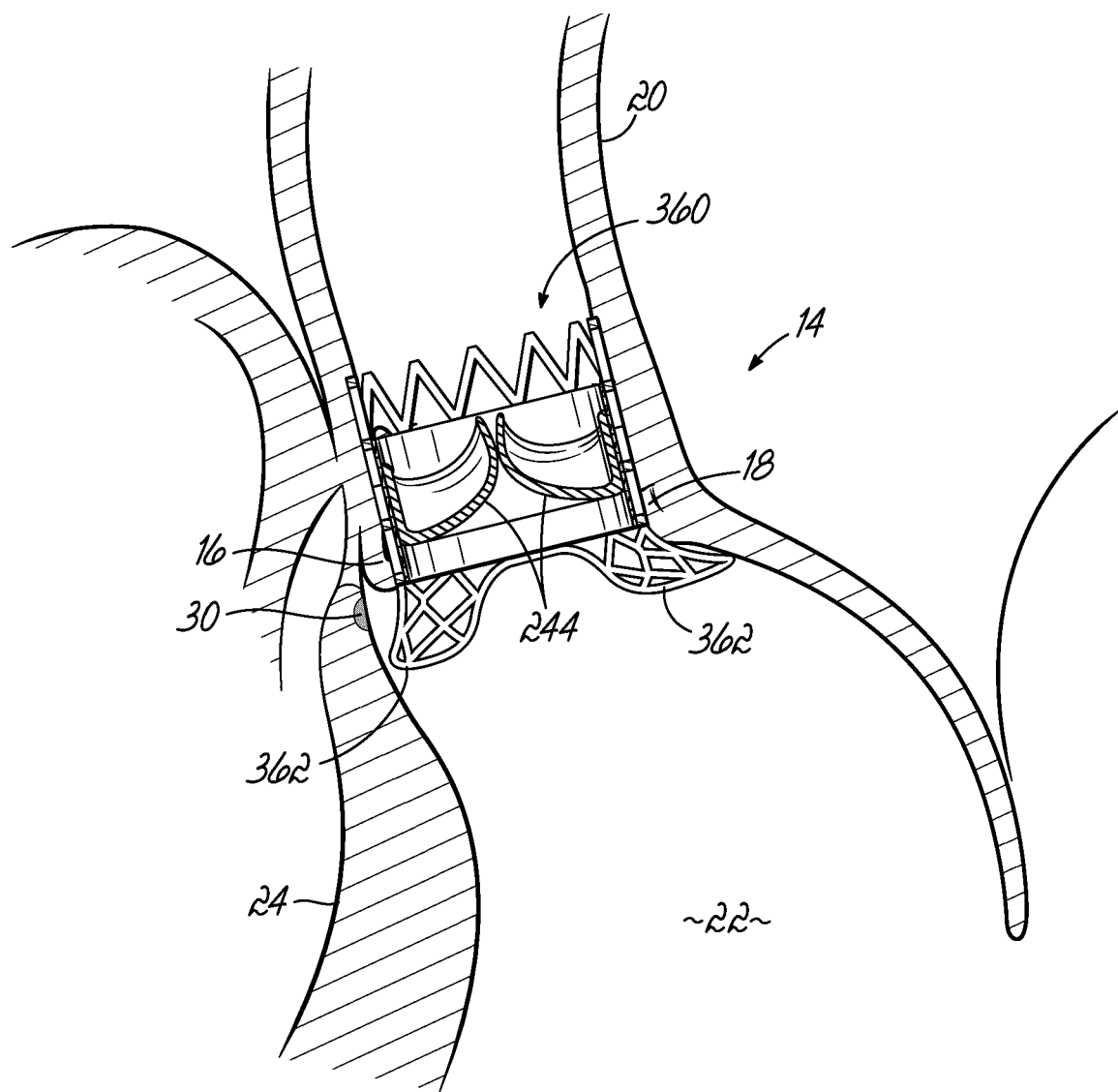
FIG. 27 is a schematic view, showing the heart anatomy in cross section, and with the stent valve of FIGS. 26A and 26B implanted.

FIG. 27 shows the prosthetic valve 360 with tabs 362 in position inside the heart. The valve 360 is very secure. The tabs 362 flare out and provide excellent protection against the valve exiting the heart. When the tabs 362 are oriented out of contact with the conduction tissue 30, there is reduced risk of heart block. The tabs 362 could be more or less turned. The tabs 362 could be longer or shorter. The tabs 362 could vary in length. While difficult to visualize, it should be noted that the tab 362 on the left in this figure is behind the conductive tissue 30 and therefore a gap (i.e., a cut-out, opening or recess) between adjacent tabs 362 aligns with the conductive tissue 30.

Figures 2, 28A:
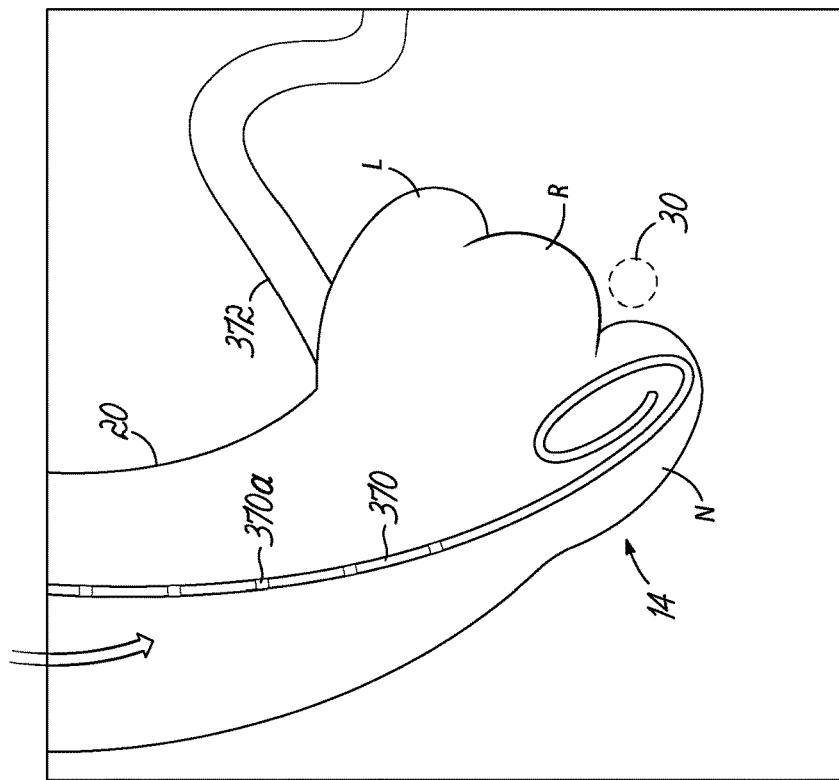
Figures 1, 28A:

FIG. 28A-1 is an image of the aortic root after it has been filled with contrast dye. The contrast has been injected through a pig tail catheter 370 that sits in the non-coronary cusp of the aortic valve 14. The three cusps of the aortic valve 14 are clearly evident. There is an echocardiography probe sitting in the esophagus adjacent to the heart. The large left coronary artery is shown filled with dye passing over the left ventricle.

FIG. 28A-2 is a drawing that illustrates the features evident in the angiographic image of FIG. 28A-1. The pig tail catheter 370 is shown for the injection of dye. It sits in the non-coronary cusp N. There are three coronary cusps all marked by letters. They are the N or non-coronary cusp, R or right coronary cusp and L or left coronary cusp. The left coronary 372 is also shown exiting from the left coronary cusp L.

Most important is the location of the conduction tissue 30. This tissue 30 sits below the junction of the non-coronary (N) and right coronary (R) cusps. This is a very reliable anatomic location. By avoiding contact between a valve prosthesis and the conduction tissue 30, heart block can be avoided.

Figure 28B:
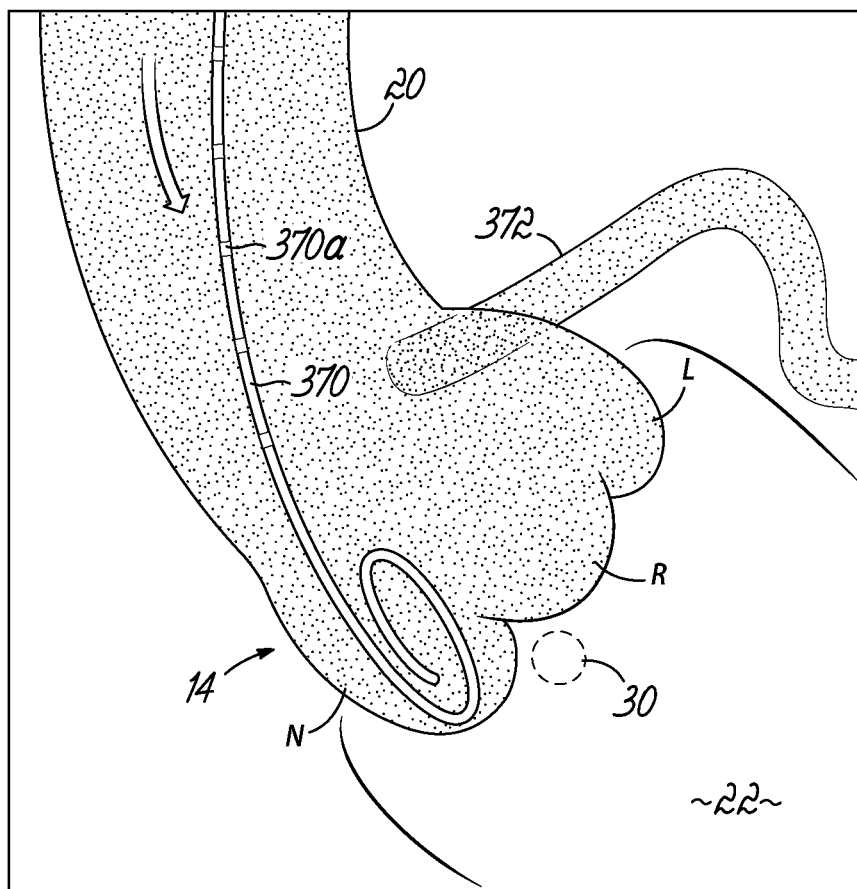
FIG. 28B is an illustration similar to FIG. 28A-2, but illustrating dye injected into the aorta and other anatomy.

FIG. 28B shows the aortic root filled with dye. The labels are identical to FIG. 28A-2.

Figure 28C:
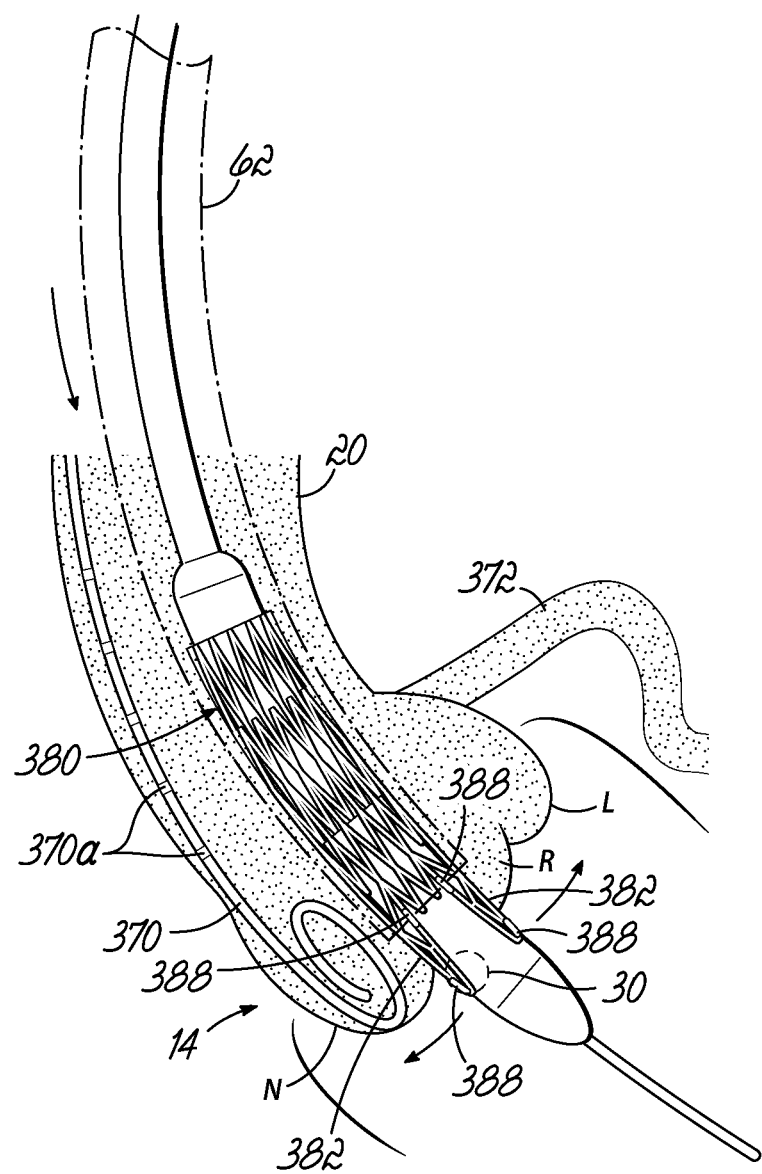
FIG. 28C is a schematic illustration showing the expandable stent valve of FIG. 27 being inserted into the native aortic valve.

FIG. 28C shows an aortic valve prosthesis 380 of the balloon expanding variety. The valve 380 has been collapsed inside a sheath 62 for delivery into the patient, usually from the groin region. The prosthetic valve 380 is shown advanced inside the diseased native aortic valve 14. The prosthetic valve 380 inside the sheath 62 has two flanges or tabs 382. The flanges or tabs 382 on the valve 380 are marked with radiopaque markers 388. This allows the interventionist to rotate the prosthetic valve 380 so that the gap or recess or cut-out 384 between the flanges or tabs 382 will sit between the non-coronary cusp N and the right coronary cusp R. This will ensure that the gap 384 between the flanges or tabs 382 will lie in the region of the conduction tissue 30. It will not contact conduction tissue 30.

The location of the native valve cusps can be determined using an angiogram as shown in FIG. 28A-1. Once a prosthetic valve 380 is advanced inside the diseased native aortic valve annulus, the outflow of blood from the heart can be obstructed and the patient can quickly become hemodynamically unstable. The valve 380 could be rotated into the appropriate position inside the native valve 14, but it is likely safer to perform this rotation before the valve 380 is advanced into position inside the native valve 14. The operator can take the time necessary to properly rotate the valve 380 relative to the position of the patient's native valve leaflets while the prosthetic valve 380 sits in the delivery system and is still located above the native aortic valve 14 inside the ascending aorta 20.

Figure 28D:
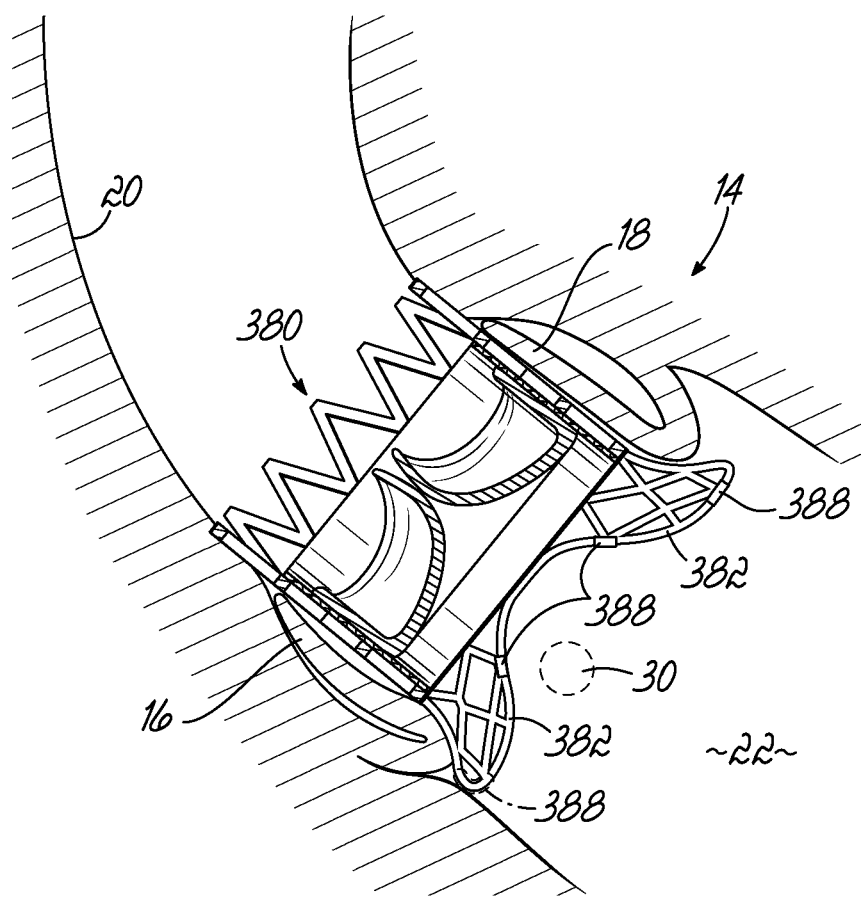
FIG. 28D is an illustration of the prosthetic stent valve shown in FIGS. 27 and 28C fully implanted at the site of the native aortic valve.

In FIG. 28D, the prosthetic valve 380 has now been released and implanted. The gap 384 between the flanges 382 is oriented at the region of the junction between the right and non-coronary cusps R, N. This means the gap 384 will be oriented so that prosthetic valve 380 does not engage the conduction tissue 30.

The valve 380 shown in this series of figures has two gaps 384 and two flanges 382. Previous figures have shown other numbers of gaps and flanges. A single flange construction with only one gap 384 in the prosthetic valve 380 may be preferred by interventional cardiologists because it increases the amount of seal to avoid a leak around the prosthesis. Or three flanges or tabs 382 may be preferred as the valve 380 could be oriented with the patient's native valve 14. The number of flanges 382 and gaps 384 is not critical, just the avoidance of contact between the prosthetic valve 380 and the conduction tissue 30.

Radiopaque markers 388 are shown on the prosthetic valve 380 in FIG. 28D. The markers 388 to show the location of the flanges 382 could also be located on the delivery system or delivery sheath. There could also be markers on both the delivery system and the valve. The markers could be different on different flanges. For example, there could be two marks on one side of a gap 384 and one mark on the other side of the gap 384 in the valve. Or different shapes of radiopaque marker could be used on different sides of the gap 384 between flanges 382.

FIG. 29A shows the general shape of the prosthetic valve 380 that has two flanges 382 in the inflow region. The inflow region does not sit in one plane. This general construction can be adapted for use with balloon expandable (Edwards), self-expanding (Medtronic and St Jude) and Nitinol wire type valves (Lotus type). A valve of any current or future construction could use such features. As explained previously, there could be different numbers of gaps 384 and flanges 382 than two. One might be preferred as this would provide a lower and longer seal to prevent paravalve leaks.

FIG. 29B shows a stent structure 390 for the prosthetic valve frame that may be used for valve 380. In dotted lines inside the frame 390, the valve leaflets 244 are shown. These are typically made from animal or biologic materials but they can be biocompatible artificial materials or bioengineered materials also.

FIG. 29C shows a top view of a prosthetic valve 380. The leaflets 244 are shown.

FIG. 30A shows a view from above of the native aortic valve root. The left (L), right (R), and non (N) coronary cusps of the valve 14 are labelled. The right coronary and left coronary arteries 392, 394 are shown coming off their corresponding sinuses of the aortic valve 14. The conduction tissue 30 sits under the junction of the right and non-coronary cusps R, N.

FIG. 30B shows the prosthetic valve 380 positioned inside the native aortic root. The prosthetic valve flanges 382 have radiopaque markers 388. These are used to orient the valve 380 in position so that the gap 384 in the valve 380 sits at the junction of the right and non-coronary cusps R, N. It is clear that the valve frame does not engage the conduction tissue 30. For orientation, the location of the original position of the native leaflets is shown (before valve implantation) with dotted lines.

Figures 2, 31A:
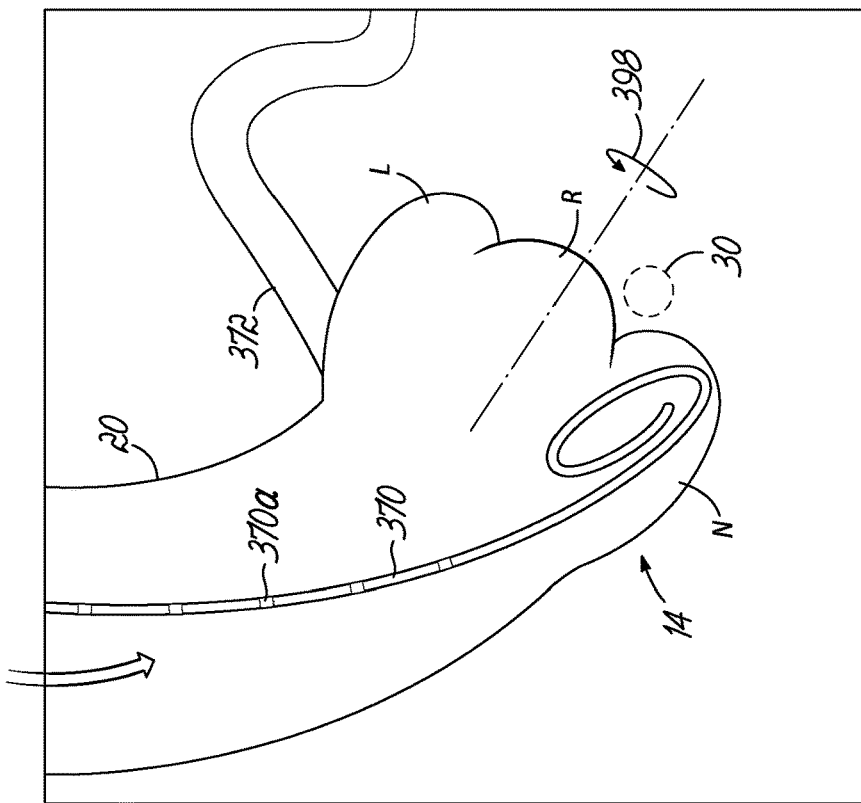
Figures 1, 31A:

FIGS. 31A-1 and 31A-2 are identical to FIGS. 28A-1 and 28A-2. The three cusps R, N, L of the native valve 14 and the location of the conduction tissue 30 are shown. A rotation and repositioning of the imaging camera angle is indicated by the arrow 398. Rotating the camera angle can produce an image that highlights the junction between the non-coronary and right coronary cusps N, R. The camera used in the catheterization lab is rotated right and left over the patient. There is also an adjustment in the camera for the cranial and caudal pitch of the camera.

FIG. 31B-1 shows an angiogram of the aortic root. FIG. 31B-2 is a drawing that corresponds to this angiogram and where the features are labelled. The figures show the non-coronary cusp (N) on the left. The right coronary cusp (R) is on the right. The conduction tissue 30 is shown as a circular region below the plane of the valve 14. This aortic root angiogram can be readily produced on angiography by having the correct camera position over the patient. This position clearly demonstrates a good image for implanting a valve with a gap. This angiography view clearly shows the correct orientation for a prosthetic valve that is to be implanted to avoid contact with the conduction tissue. There are a number of options to produce this view. One option would be to perform a baseline aortic root injection while moving a camera to identify an ideal angle to produce a view similar to this angiogram. This baseline angiogram would then be used to identify camera positions suitable to perform the prosthetic valve implant procedure.

Many interventional cardiologists prefer not to inject any additional dye. Angiographic dye can be toxic to the kidneys. Prior to valve implantation, a baseline image with a CT scan is often taken. These images can be used to plan the procedure. Current software is highly effective in reconstructing images of the aortic root. One commonly used system is 3Mensio. This CT finding tool (as well as others) can be used to predict with a high level of accuracy the exact camera angle that will be necessary to show the non-coronary cusp on the left and the right coronary cusp on the right. This is the camera angle that was used to produce the angiographic image in FIG. 31B-1. For example, the CT analysis tool may find that a typical camera angle to image the aortic valve and demonstrate the junction between the right and non-coronary cusps is about ten degrees RAO (Right Anterior Oblique) and with about 10 degrees of caudal tilt. Patients vary in the position and orientation of their aortic root and in their body habitus. So this tool could be used to prevent the need for a full dye injection. Once the CT has been used to predict the ideal camera angle, the interventionist could place a pig tail catheter 370 in the non-coronary cusp N, position the angiographic camera at the predicted location and inject a small puff of dye to ensure the predicted angle was correct. Slight adjustments may be necessary to obtain the ideal camera angle. Ultimately, if the prediction from CT imaging is proved to be sufficiently accurate, this step of flushing the aortic root could be avoided. It should be noted that the valve designs shown have a considerable gap between the flanges. There may be a small error in the predicted camera angle, but since the flanges miss a considerable amount of the native valve annulus, it may not be necessary to perfectly orientate the prosthetic valve inside the native aortic valve.

Other imaging techniques such as transthoracic ultrasound, trans-esophageal ultrasound and MR scanning could also be used to provide the information to position the camera for valve implantation. Sometimes valve leaflets are heavily calcified. The calcification of the leaflets may define the shape and location of the leaflets without dye injection. So in some patients, imaging with fluoroscopy of the leaflets alone (or in combination with information from other imaging modalities) may provide the correct position for imaging the non-coronary to right coronary cusp junction.

The same procedure of defining the location of the commissure between the right and non-coronary cusps R, N could be used to implant a prosthetic valve with one gap. The gap would be implanted straddling this commissure junction.

The positioning of the prosthetic valve is ideally done before the valve is placed inside the native aortic root. The prosthetic valve can be positioned and rotated above the native aortic valve. The position of the native leaflets and the position of the prosthetic valve can be imaged. The prosthetic valve can then be rotated and using the guidance of markers on the delivery system or the valve itself, the correct orientation of the prosthesis can be determined. After this can be completed, the valve can be advanced through the native aortic annulus and rapidly deployed. As indicated previously, the patient may become hemodynamically unstable once the prosthetic valve is moved inside the native leaflets, so it seems prudent to orient a prosthetic valve before placing it inside the native aortic valve annulus.

Radiopaque markers can vary in their location. The key is that they provide information on how to orient the valve to avoid the prosthetic valve contacting the conduction tissue.

Figure 31C:
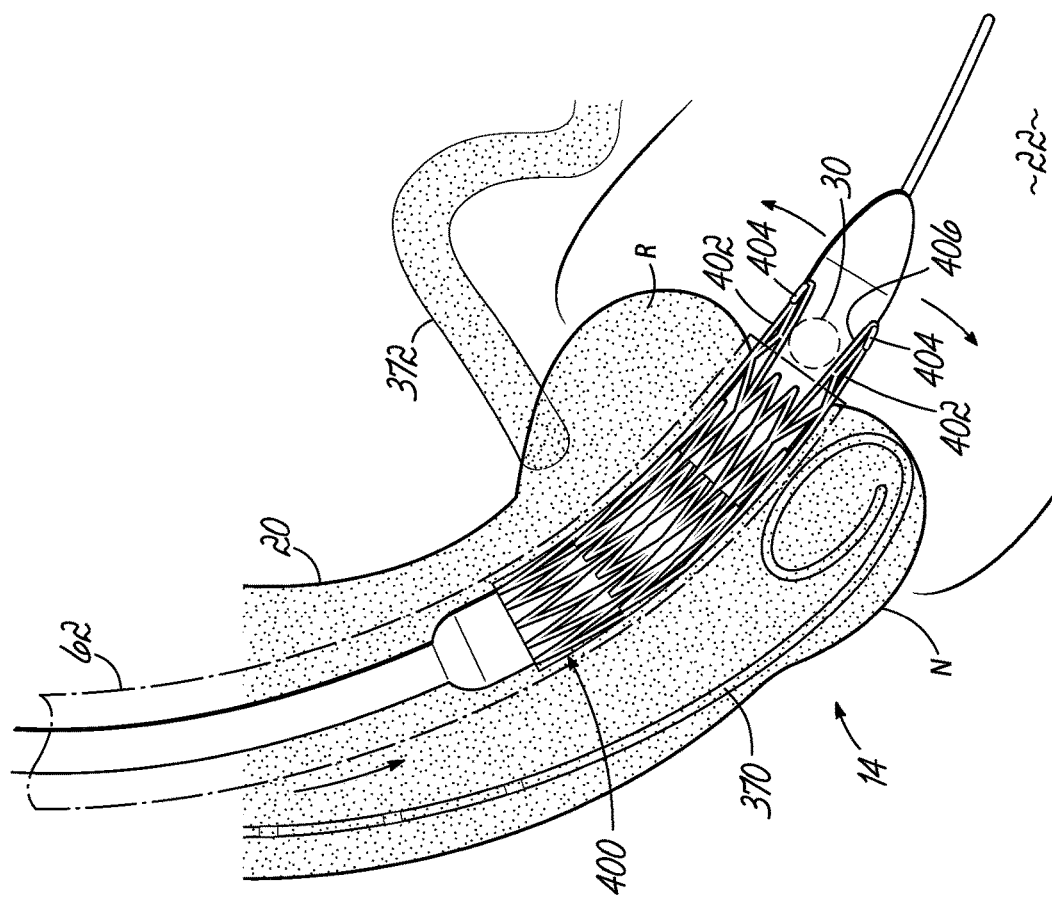
FIG. 31C is a schematic illustration showing the insertion and initial implantation of an expandable stent valve in accordance with an embodiment of the invention being inserted into the native aortic valve.

FIG. 31C shows a prosthetic valve 400 with two flanges or tabs 402. Each flange 402 is marked with a radiopaque marker 404. The valve 400 has been rotated so that the markers 404 have been positioned so that one marker 404 is located toward the non-coronary cusp N and the other toward the right coronary cusp R. This can be done by rotating the prosthetic valve 400 so that the radiopaque markers 404 are maximally spread apart from each other when viewed in an angiographic image such as shown in FIG. 31A-1. As stated previously, there are many ways to use the angiographic markers 404. There could be different shaped or numbers of markers 404. A marker 404 could be placed on the highest point of the inflow of the prosthetic valve 400 and this marker 404 could be oriented to the location of the right and non-coronary cusps R, N.

Once the prosthetic valve 400 has been introduced inside the native leaflets, it can be unsheathed and released in the correct orientation. The gap 406 between the flanges 402 is shown oriented with the conduction tissue 30.

Figure 31D:
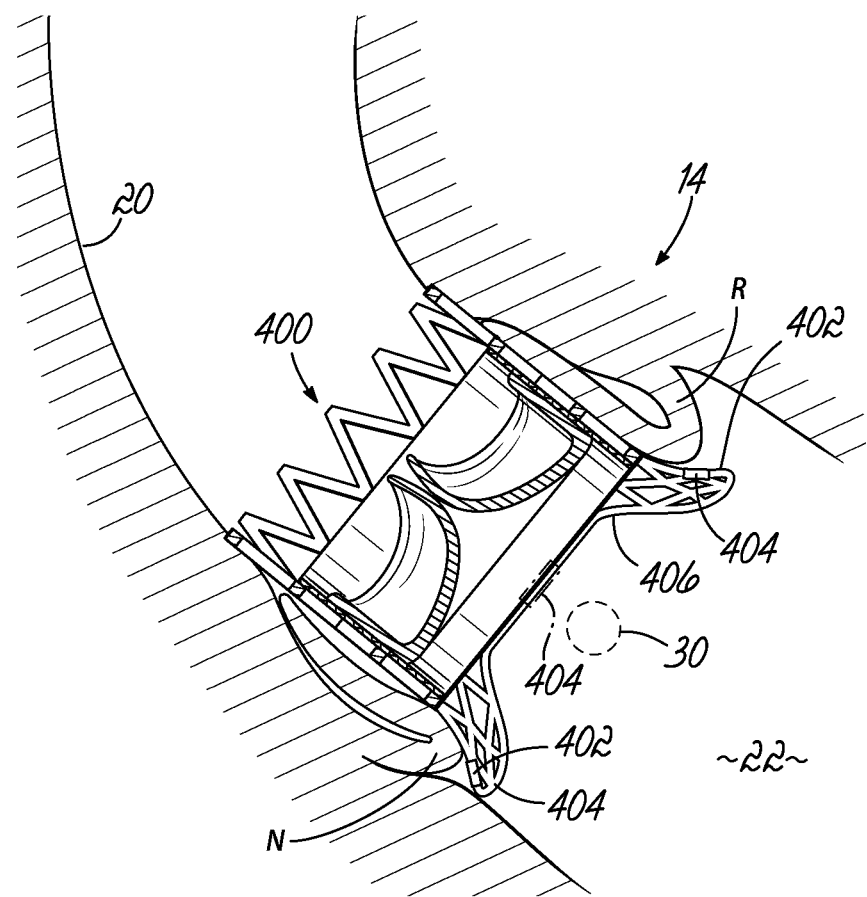
FIG. 31D is an illustration similar to FIG. 31C, but illustrating the fully implanted expandable stent valve within the native aortic valve.

FIG. 31D shows the final position of the implanted valve 400. The valve 400 has two flanges 402 oriented safely away from the conduction tissue 30. As mentioned previously, the number of gaps 406 and flanges 402 could be varied. The shapes and number of the radiographic markers 404 could be adjusted. Additional markers 404 may be useful. For example, it may be useful to add a marker 404 half way between the two flanges 402. Such a marker 404 would identify the highest point of the inflow end of the prosthetic valve 400.

The flanges 402 shown on this valve 400 are equal in size. The flanges 402 could be unequal. Some patients have a very "horizontal" aortic arch. In these patients, the aorta does not demonstrate the typical U turn shown in textbooks. When a prosthetic valve is introduced from the groin through a horizontal arch, it often is released on a slightly eccentric angle. By making one flange longer, wider or larger than the other, it may be possible release the prosthetic valve 400 so that is better aligned with the native aortic root and the left ventricular outflow. In a typical procedure, the interventionist releases a self-expanding valve partially inside the left ventricle and then draws the catheter out of the heart until it engages with the native aortic valve and left ventricular outflow. A longer flange on one side of the prosthesis 400 may engage with the heart on one side of the left ventricular outflow and straighten the prosthetic valve 400 so that is aligned more precisely with the left ventricular outflow.

Helical devices have been described herein to assist in correct placement of the prosthetic aortic valve. These helical devices can help to position the depth of placement of a valve so that the valve does not impact against conduction tissue 30 sitting below the annulus 14a. These devices can also ensure that the valve implantation starts from a central position inside the annulus 14a so that the expanded valve is implanted parallel to the left ventricular outflow. When the aorta 20 is "horizontal" the native valve 14 can be approached at a skewed angle by the catheter that implants the valve prosthesis. The use of a helix ensures that the valve implantation is begun at the center of the native annulus.

Figure 32A:
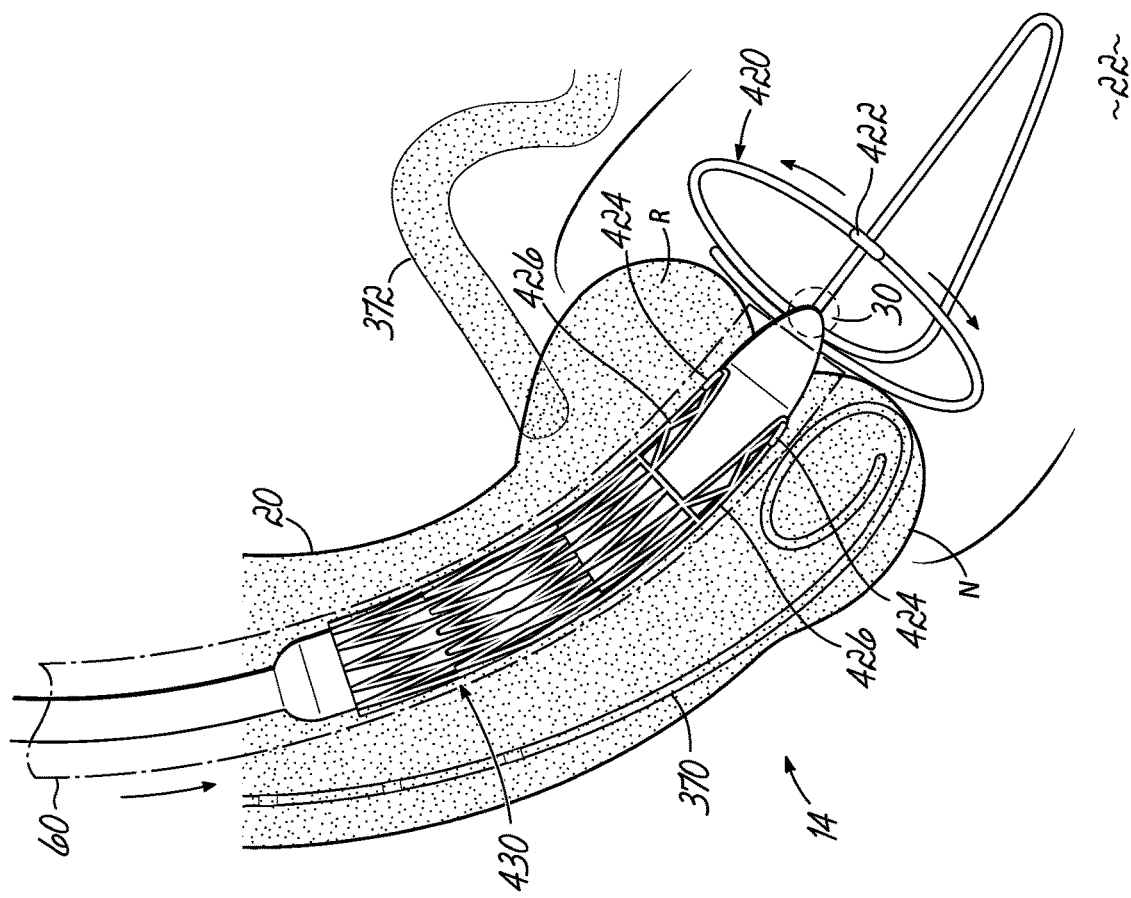
FIG. 32A is an illustration similar to FIG. 31C, but illustrating the use of a positioning or guide device within the left ventricle during the implantation procedure.

FIG. 32A shows an additional feature on a helical guide device 420. This feature is the addition of one or more radiopaque markers 422. The marker 422 in this figure can be rotated and positioned to identify the location of the conduction tissue 30. In this figure, the marker 422 has been positioned just below the junction of the right and non-coronary cusps R, N—where the conduction tissue 30 sits. The marker 422 on the helix 420 can then be aligned relative to the markers 424 on the prosthetic valve flanges 426. This ensures the gap 428 between the flanges 426 will sit over the conduction tissue 30.

Additional radiopaque markers could be placed on the straight segment of the positioning or guide device 420 to indicate the depth of valve implant 430. For example, the helix 420 could be pulled back against the underside of the leaflets of the native aortic valve 14. Another radiopaque marker (not shown) could indicate how far down the positioning or guide device 420 the interventionist should locate the prosthetic valve 430 for implantation.

To perform this procedure, the interventionist would place the helix 420 inside the left ventricle 22 and align the marker 422 with the position of the conduction tissue 30. The valve 430 and its delivery catheter 62 could then be advanced over the helical device 420 and positioned inside the annulus 14a with care to orient the markers 424 on the prosthetic valve 430 appropriately with the helix marker 422. The sheath 62 covering the valve 430 can be removed and the valve positioned. In this arrangement, the helical guide 420 has three functions—1) it helps determine the depth of implant, 2) it orients the valve prosthesis 430 correctly relative to the commissures or cusps N, R, L and conduction tissue 30 and 3) it assures that valve release will begin in the center of the annulus 14a and that the valve 430 will be expanded in a direction parallel to the left ventricular outflow and the aorta 20. It can make the entire procedure safer—reducing the time needed to adjust the prosthesis 430 while it is sitting unreleased inside the annulus 14a before it is released.

Figure 32B:
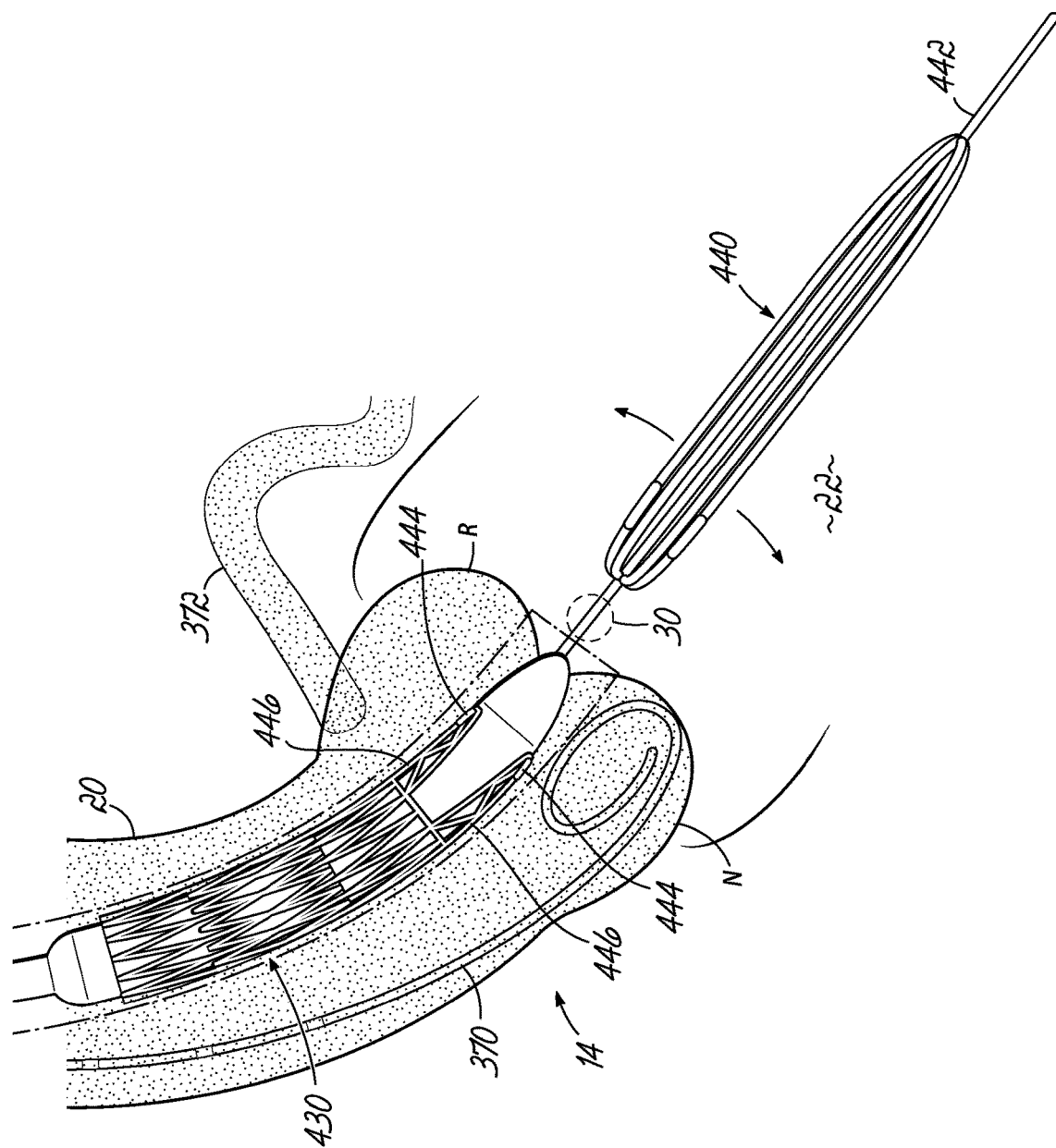
FIGS. 32B and 32C are illustrations similar to FIG. 32A, but showing an alternative guide device being used for positioning the expandable stent valve at a level that avoids contact or negative engagement with the conduction tissue.

Previously, a variety of devices have been shown that assist in positioning a prosthetic aortic valve 430. FIG. 32B shows another variation of a valve positioning or guide device 440. This figure shows an expandable basket device 440. The basket 440 can be inserted inside the left ventricle 22 at the end of a delivery wire 442. The basket 440 is delivered in a closed shape. The valve 430 and its delivery system can be advanced over this device 440.

Figure 32C:
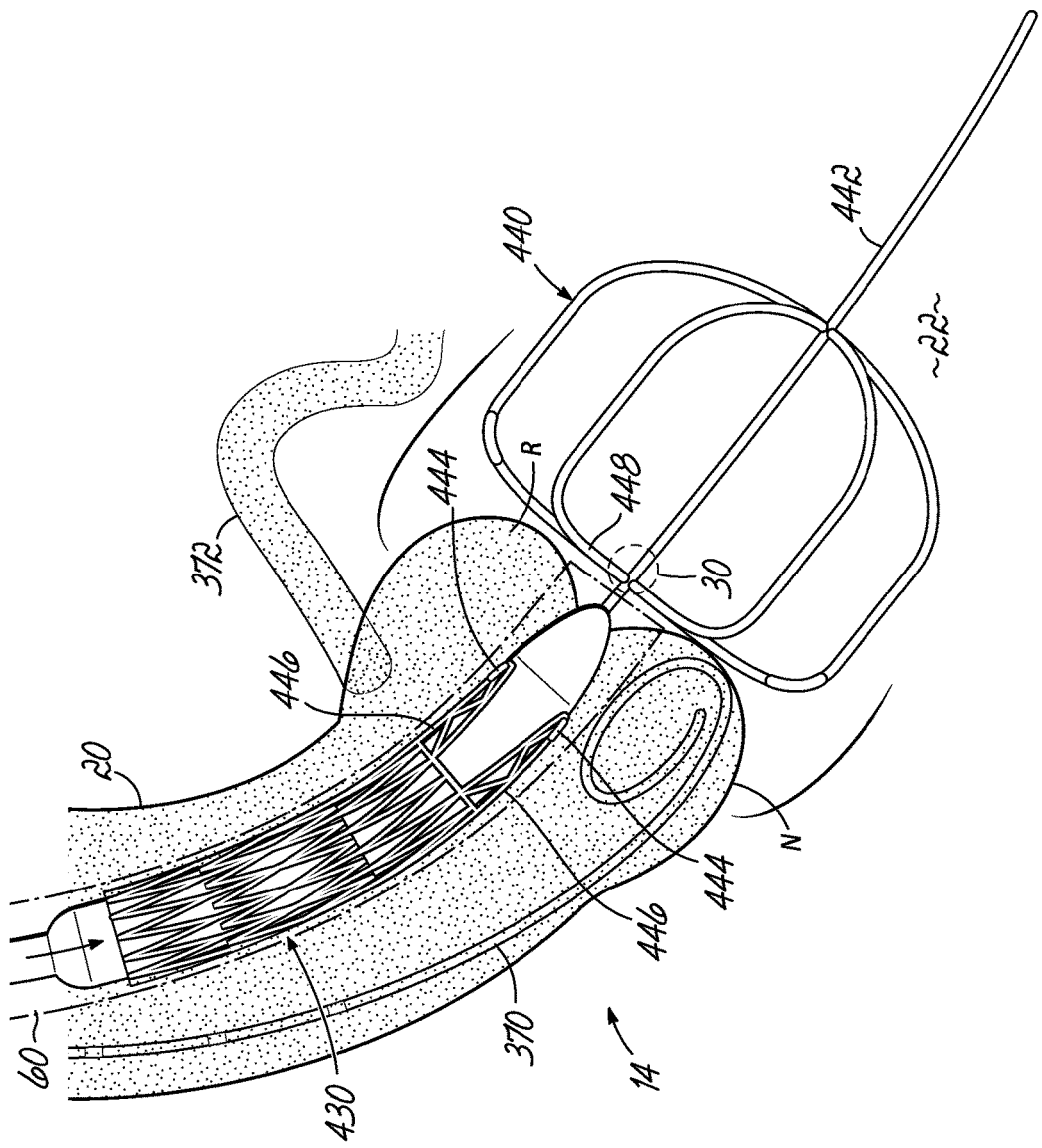

FIG. 32C shows the basket 440 expanded inside the left ventricular outflow. There are radiopaque markers 444 shown on the basket 440. The markers 444 are located on arms 446. The conduction tissue 30 in this arrangement is located in the center of the markers 444. The prosthetic valve 430 with the flanges 426 is rotated so that each flange 426 is directed toward one marker 444 on the basket 440. Many different patterns of radiopaque markers 444 could be used. The key item is that the markers 444 on the positioning device 440 can be oriented relative to the conduction tissue 30. Then the valve 430 for implantation can be oriented relative to the positioning device 440. Any marker arrangement that helps to avoid valve implantation in contact with conduction tissue 30 is useful.

The depth of the basket device 440 can be adjusted to help control the depth of the implant. Additional radiopaque markers could be placed on the straight segment 448 of the positioning device 440 to indicate to the cardiologist where to place the distal tip of the valve delivery system. Previously, the turn in the wire leading into the helix has been shown as a "stopper" for valve positioning depth. In this variation, the top 450 of the basket device 440 could be used as a "stopper" to indicate where the valve implantation should start.

The basket 440 could vary in shape. For example, there could be an indentation (not shown) at the upper end of the basket 440 to accommodate the valve.

This device 440 again serves three functions—1) It helps determine the depth of the implant of the prosthetic valve 430 inside the annulus 14a, 2) It helps center the implantation of the valve 430 inside the annulus 14a (particularly helpful in the short horizontal aorta) and 3) It helps orient the implant of the prosthetic valve 430 to avoid injury to conduction tissue 30. Further, it can make the procedure faster and safer—even for less skilled interventionists.

FIGS. 33A1, 33A2, 33B, 33C and 33D show a sequence for implantation of a Lotus type valve 450 (sold by Boston Scientific). This valve 450 is composed of a mesh of wires. The valve 450 is delivered in a lengthened shape and then the mesh shortens as the valve 450 is implanted inside the native valve 14. The valve variation in these figures show that a Lotus type valve 450 can be structurally changed to have an inflow gap 452 that avoids the conduction tissue 30. This valve 450 is shown with two gaps 452. As with all the other valves, there could be one or more gaps 452 in the construction. Radiopaque markers 456 can be added to locate the position of the flanges or tabs 458 on the valve.

Figures 2, 33A:
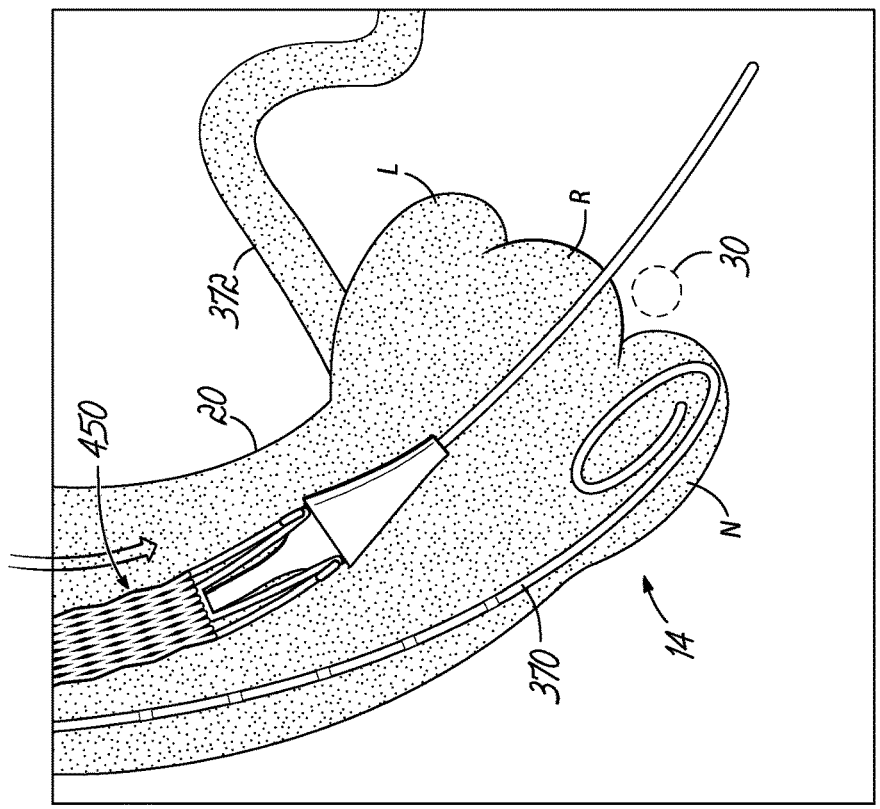
Figures 1, 33A:
Figure 33B:
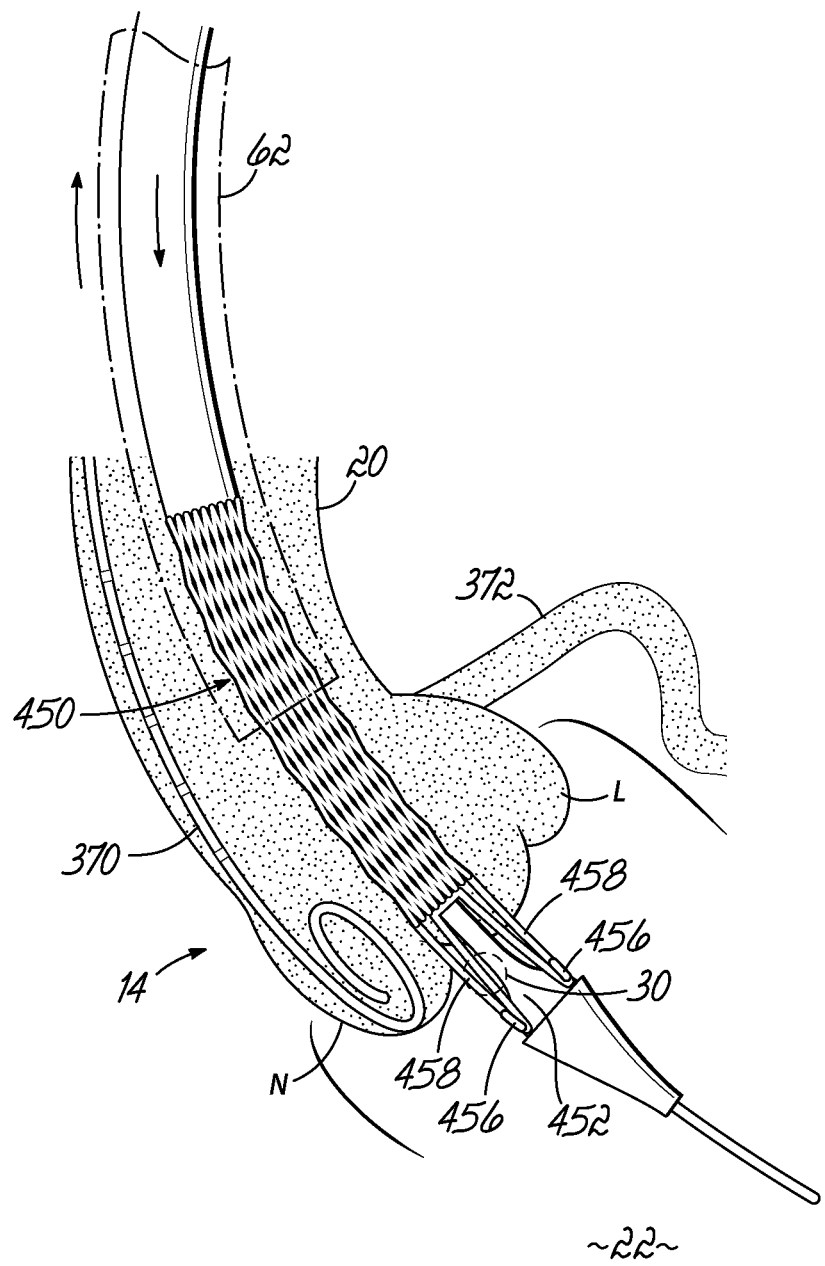
FIG. 33B is an illustration similar to FIG. 33A-2, but illustrating a further point in the procedure during which the expandable stent valve has been inserted through the native aortic valve.
Figure 33C:
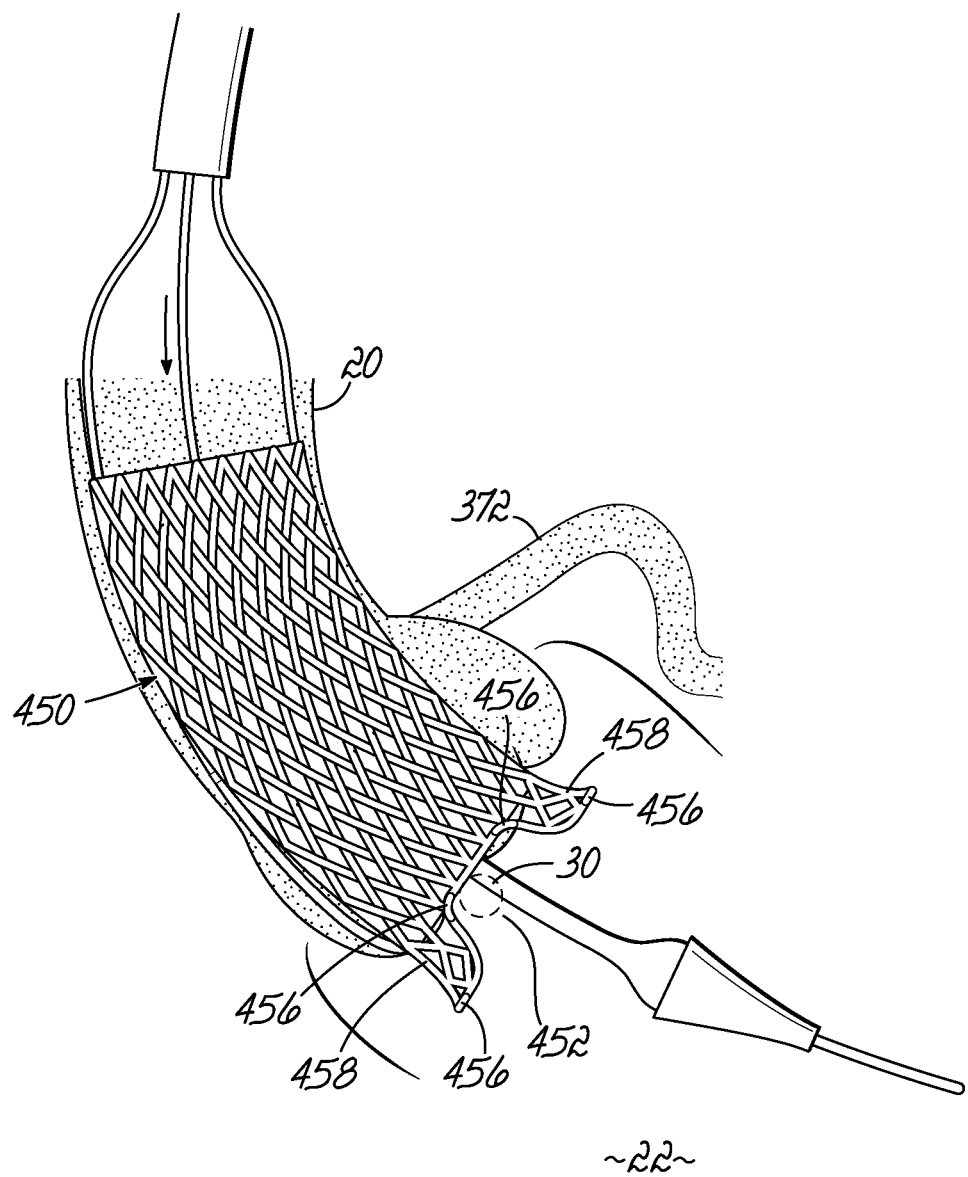
FIG. 33C is a view similar to FIG. 33B, but illustrating expansion of the stent valve within the native aortic valve.
Figure 33D:
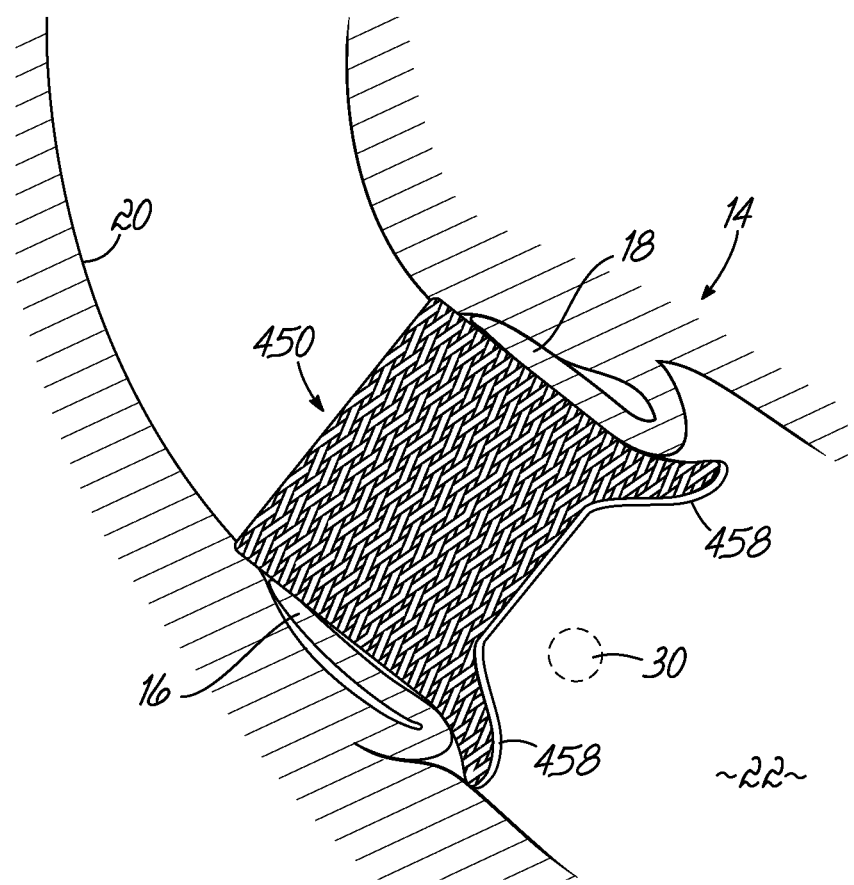
FIG. 33D is a view similar to FIG. 33C, but illustrating full expansion and implantation of the prosthetic stent valve within the native aortic valve.

These are shown in FIG. 33B. The location of the highest point on the inflow could also be identified with a radiopaque marker 460. It should be noted that the valve variations shown in all of these figure series have demonstrated two inflow flanges 458. The same concepts could apply to more or few flanges 458 or to the use of valves made with U-shaped, cut-outs or recesses or circular cut-outs or recesses that have been shown previously.

Figure 34:
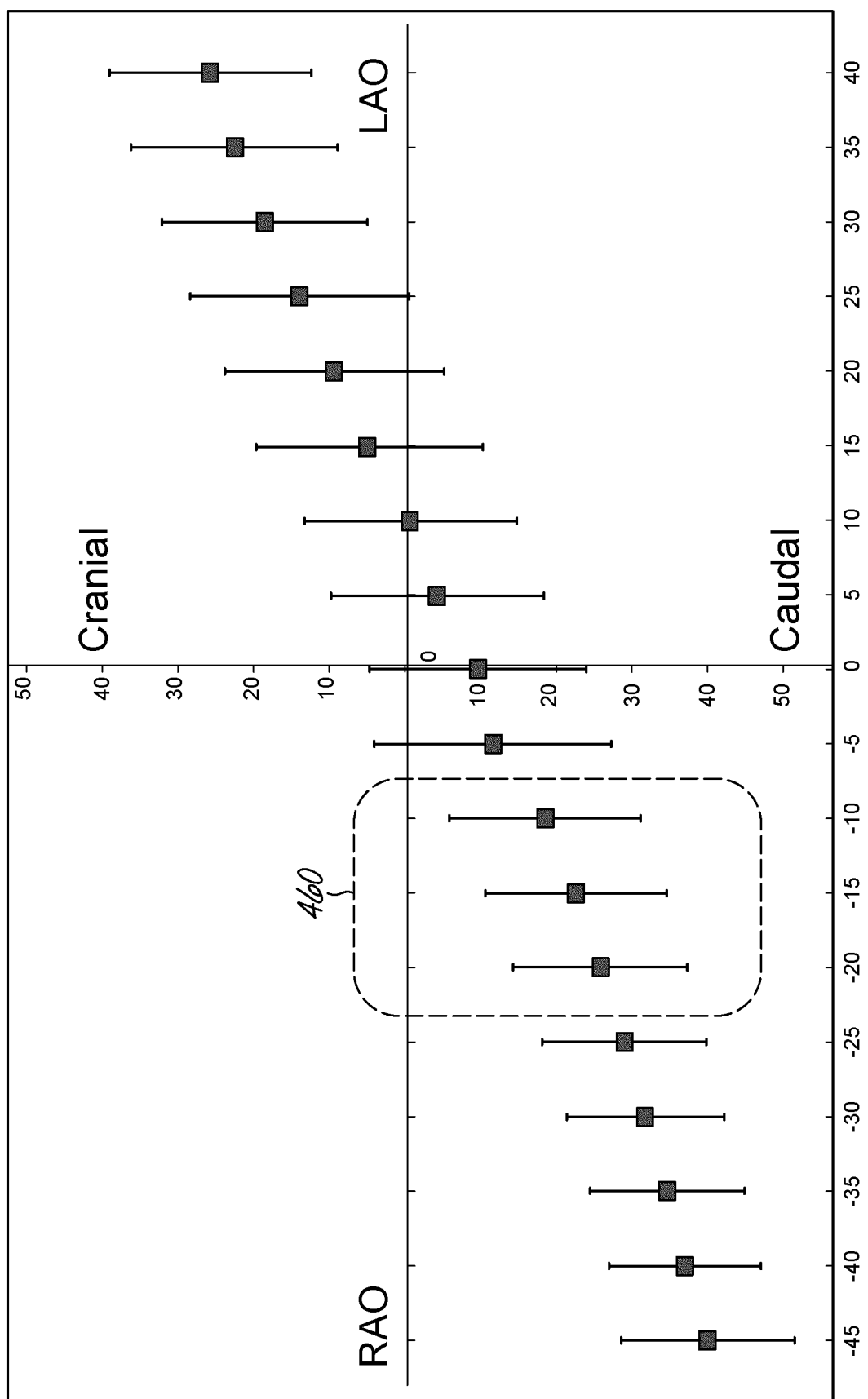
FIG. 34 is a diagram illustrating the angle of a typical native aortic valve and optimal viewing image location for a procedure conducted in accordance with the embodiments of the invention.

Referring to FIG. 34, the plane of the aortic valve in a typical patient is not horizontal. The valve plane is lower on the patient's right and higher on the patient's left side. To image in the plane of the aortic valve cardiologists have developed estimates for commonly used camera angles for visualization of the aortic valve in plane. This figure shows the range of typical camera angles in a left and right plane and in an up and down plane that are helpful in planning imaging of the aortic valve. One axis of the figure shows the left and right camera angle positions—RAO (right anterior oblique) and LAO (left anterior oblique). The other axis shows the up and down camera positions. The upper angles (toward the patient's head) are identified as Cranial. The lower angles (toward the patient's feet) are marked as Caudal. The figure shows that the plane of the aortic valve generally travels from lower on the right to upper on the left. The error bars indicate that there is a wide range of variation between individual patients.

FIG. 34 is useful because it can provide a starting estimate for imaging in the plane of the aortic valve 14. The typical location of the junction between the right and non-coronary aortic cusps R, N sits along this general plane and is most commonly a little right of the midline. So a typical junction between the right and non-coronary cusps R, N may be best imaged with a camera positioned in the region shown in the dashed area 460.

This starting information is useful. A cardiologist can start a procedure with these coordinates in mind and then refine the localization of the commissural junction by injecting a small amount of contrast dye.

CT of the aortic root with contrast is almost always done prior a valve implant procedure to assess the dimensions of the aortic annulus to assist in selection of an appropriately sized trans-catheter heart valve (THV) implant. These images can also be used to predict the optimal fluoroscopy projections to be used during implantation. These same CT images can easily be used to predict optimal imaging projections for the NC (non-coronary) to R (right) cusp commissure. Ultrasound and MR may also help to precisely guide best imaging coordinates.

Figure 35:
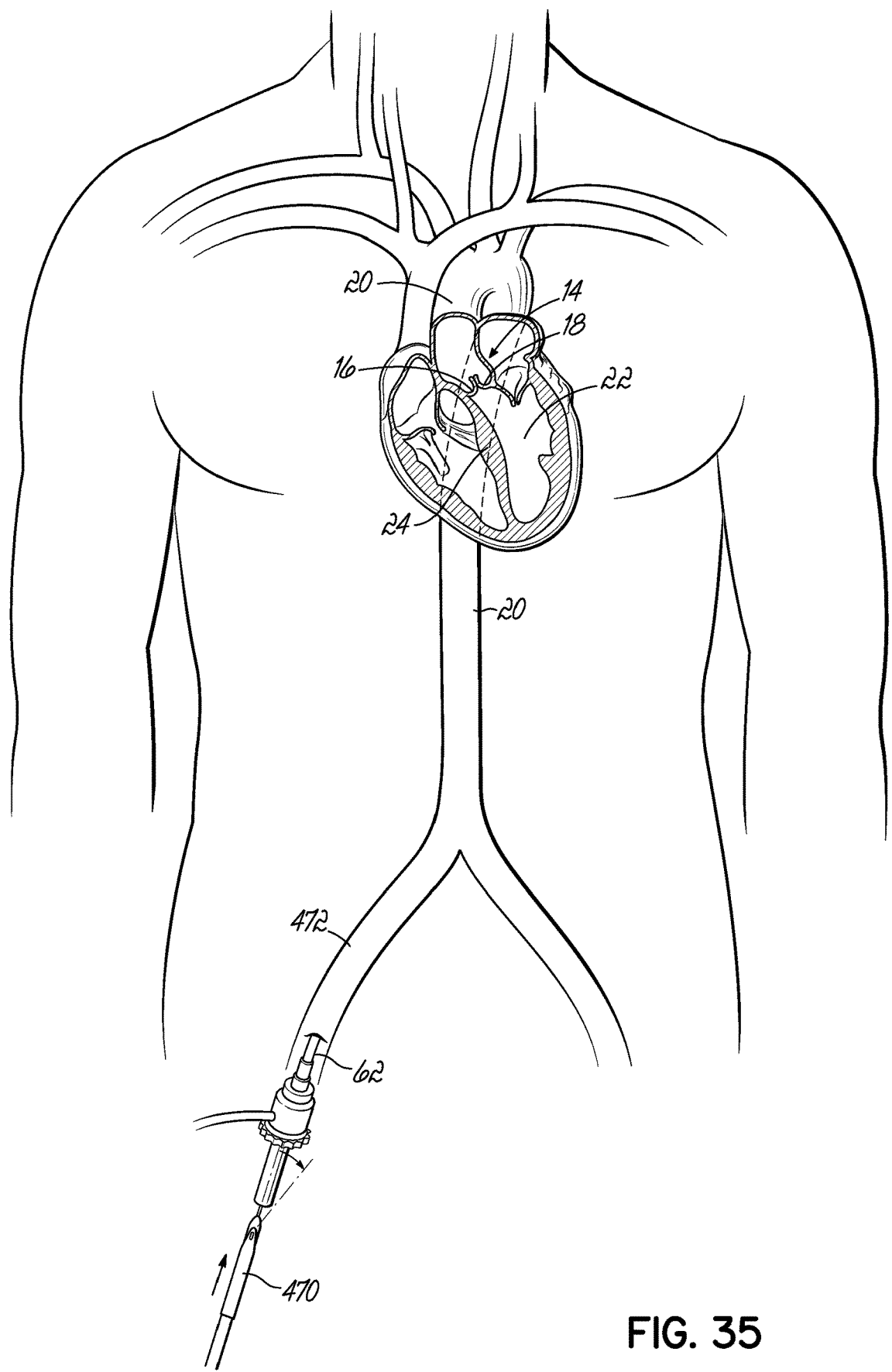
FIG. 35 is a schematic illustration of a patient and the entry location and orientation procedure associated with embodiments of the invention.

FIG. 35 shows the introduction of a percutaneous aortic valve prosthesis from the right groin region of a patient. Typically, an introducer sheath 62 is placed in the artery in a groin. The collapsed prosthetic valve 470 and its delivery system are advanced from the groin artery, up the aorta 20 and to its position inside the native aortic valve 14. The patient's aorta 20 follows close to the vertebral column, usually just on the left side of the aorta 20. So, the aorta 20 is close to the back of the patient. The aorta 20 has an arch which turns forward and to the left side of the patient. So, the prosthetic valve 470 will be directed up the aorta 20 traveling close to the patient's back, and then makes a roughly U-shaped turn forward toward the front of the patient as it simultaneously curves to the left. As an approximation, the part of the prosthetic valve 470 that is introduced at the groin will bend forward so that the part of the prosthesis 470 that is directed toward the back of the patient at entry in the groin will end up towards the front of the patient when the valve prosthesis 470 passes around the aortic arch. The ideal orientation for the part of the valve prosthesis 470 that avoids the conduction tissue 30 is approximately fifteen degrees to the right. Therefore, it is possible to avoid rotations inside the aorta 20 for the prosthesis 470 by introducing the part of the valve 470 that is intended to be placed at the junction of the right and non-coronary cusps R, N toward the back of the patient, with a rotation that brings the part of the prosthesis 470 that avoids the conduction tissue 30 rotated to account for this final, desired location or orientation.

The correct orientation, and location from a rotational standpoint for the valve prosthesis 470 can generally be estimated by the interventionist. Or, the images from CT, MR or information from echo-ultrasound or any modality can be used to precisely predict the ideal insertion orientation. The exact course of the femoral, iliac, aorta, aortic arch and the orientation of the native valve 14 can be used to predict the correct orientation. An algorism may be produced from imaging modalities to help the interventionist to improve the accuracy of the insertion orientation of the valve prosthesis 470. The more accurate the insertion, the less the need to rotate the valve prosthesis 470 once it is placed at the implantation site.

Figure 35A:
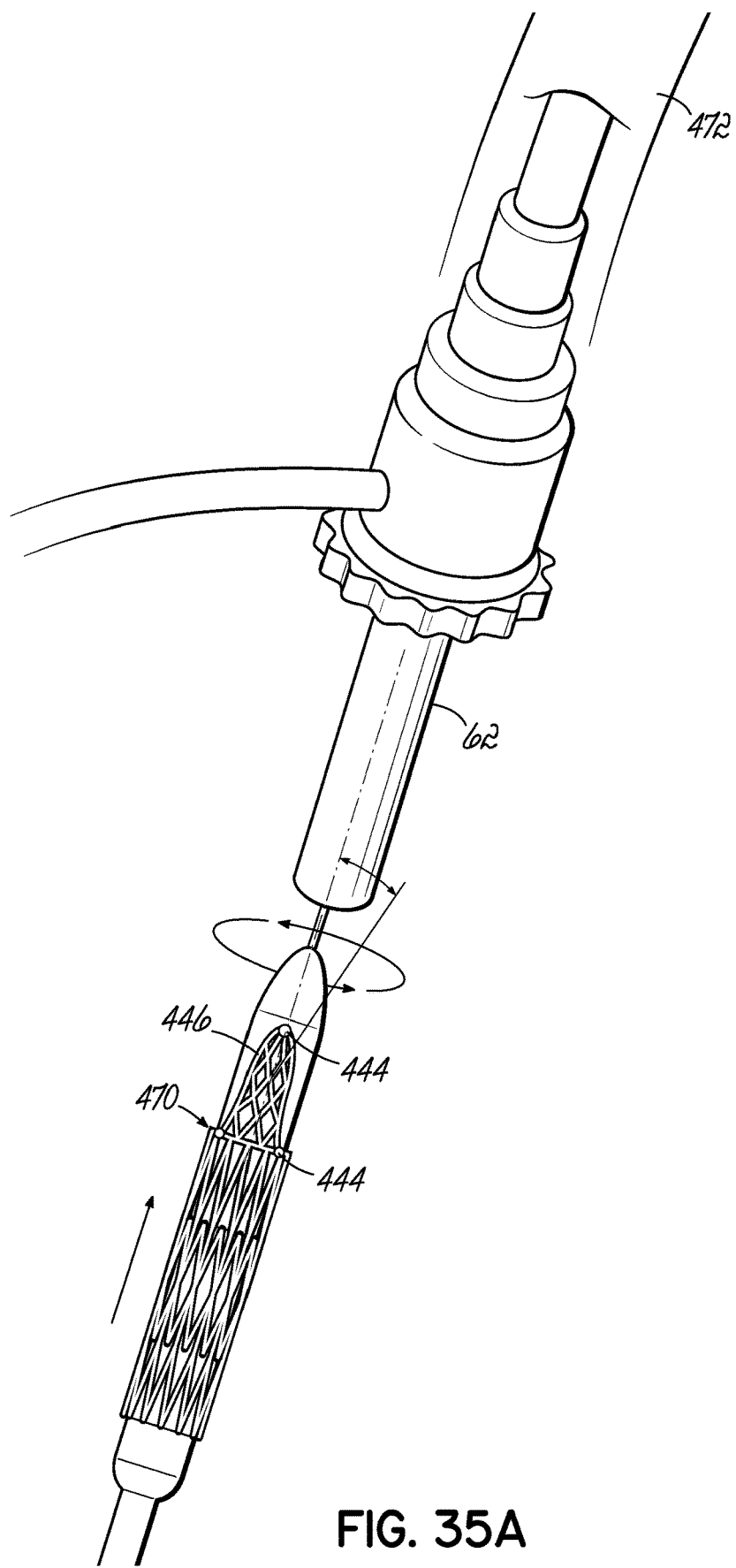
FIG. 35A is an enlarged view of the insertion location and orientation procedure for an expandable stent valve in accordance with embodiments of the invention.

FIG. 35A shows an enlarged view of the valve prosthesis 470 being oriented in an angular or rotational sense during its insertion inside the femoral artery 472. It would be very useful to introduce the valve prosthesis 470 into the femoral artery at an orientation that results in the part of the prosthetic valve 470 that is designed to avoid the conduction tissue 30 arriving at the native aortic valve 14 at the junction of the right and non-coronary cusps R, L. As previously discussed, this would place the cut-out, recess, or gap etc. that is designed to avoid the conduction tissue 30 in alignment with that conduction tissue 30. This portion of the inventive procedure can be generally predicted from understanding the course or path of the aorta 20. Further refinements may be made using data from scans showing each patient's individual anatomy. Ideally, the valve prosthesis insertion should be perfect, i.e., there would not be a need in this case to adjust the rotation of the prosthetic valve 470 inside the patient's aorta or at the implantation site. Most likely, any estimate and even an algorithm will be slightly off from the idea position. But, the need for a rotation or adjustment at the implantation site may be reduced to just a few degrees of rotation, thereby reducing the time and the risk associated with the procedure.

Figure 36A:
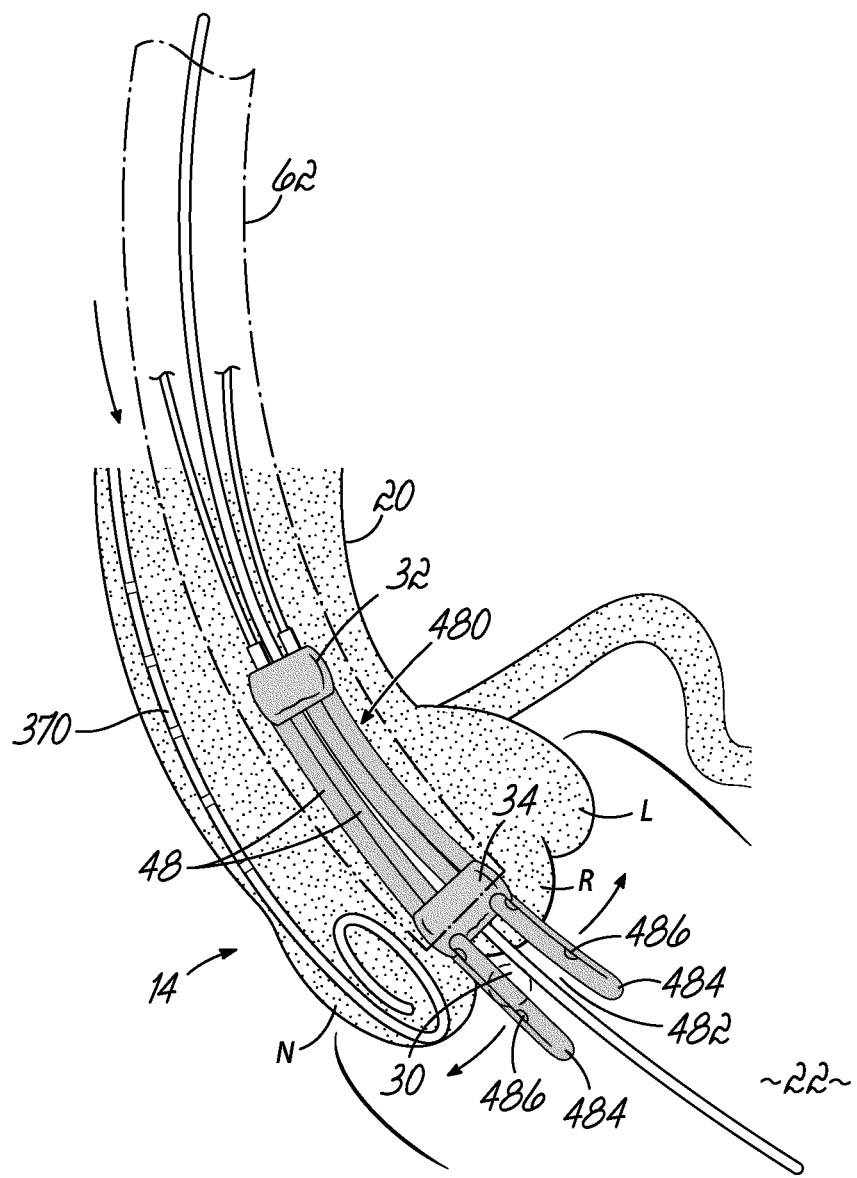
FIG. 36A is a schematic illustration of an inflatable prosthetic aortic valve constructed in accordance with an embodiment of the invention being inserted into a native aortic valve.
Figure 36B:
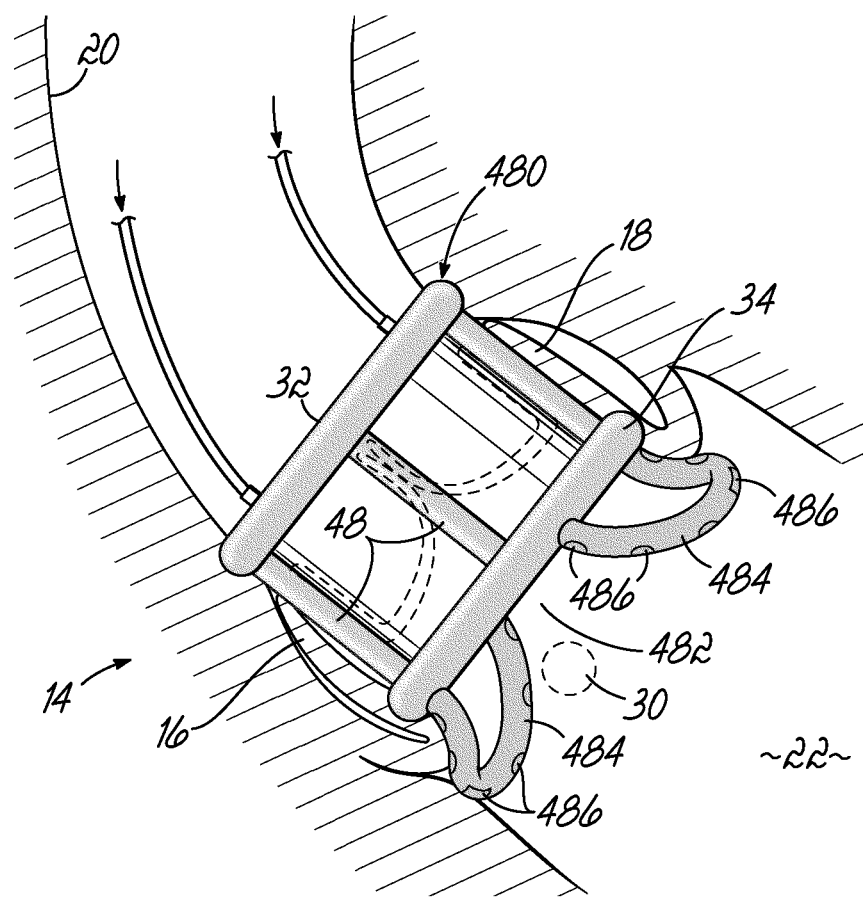
FIG. 36B is a view similar to FIG. 36A, but illustrating full expansion and implantation of the inflatable prosthetic valve within the native aortic valve.

FIGS. 36A and 36B respectively show a collapsed and an expanded version of an inflatable aortic prosthetic valve 480 that avoids contact with the conduction tissue 30 in a manner similar to those previously described. Many previous variations have been shown for the construction of prosthetic valves that avoid contact with the conduction tissue 30. While this not the only form that an inflatable prosthetic valve may take, it nevertheless illustrates the key point of avoiding contact with the conduction tissue 30 through the formation of a gap, cut-out or recess 482 in the valve 480, and orienting that gap, cut-out, recess, or other structural void in the prosthetic valve over or in alignment with the conduction tissue 30. In this embodiment the valve 480 includes cut-outs, openings or recesses 482 at the lower margin separated by arms or tabs 484 flaring or extending radially outward from the lower margin or ring 34. These tabs 484 include radiopaque markers 486 to assist the interventionist in placing and orienting the valve 480. Specifically, the interventionist will be assured that no portion of the valve 480 negatively contacts or engages the conduction tissue 30.

Various disclosure and descriptions herein have focused on implantation of a prosthetic valve with two flanges. The same procedures and methods could be used to implant a valve with one or three flanges.

A three flanged valve might best be implanted by orienting the prosthetic valve with the native aortic valve. It could follow the scallops of the native valve and the anchor for the valve would not contact conduction tissue.

Although not shown here, these same concepts could be extended to mitral or other valve implantation. Templates or guides could be constructed to improve the implant of a prosthetic mitral valve.

The invention claimed is:

1. A method of implanting a prosthetic aortic valve in a native aortic valve of patient with a delivery sheath, the prosthetic aortic valve including a stent frame having an interior and three prosthetic valve leaflets mounted within the interior and joined at three respective commissures to provide unidirectional flow of blood through the prosthetic aortic valve, the stent frame further including a portion at a lower edge thereof, the method comprising:

collapsing the prosthetic aortic valve into a collapsed configuration;

loading the prosthetic aortic valve in the collapsed configuration into the delivery sheath so that a selected point on the prosthetic valve is rotationally aligned relative to a long axis of the delivery sheath with a selected radiopaque marker on the delivery sheath;

introducing the delivery sheath along the long axis of the delivery sheath into a vasculature of the patient;

advancing the delivery sheath until a distal end of the delivery sheath is disposed in an ascending aorta of the patient with the entire prosthetic aortic valve in a position above the native aortic valve;

while the entire prosthetic aortic valve is in the position above the native aortic valve, fluoroscopically imaging the native aortic valve with a fluoroscopic camera;

setting a position of the fluoroscopic camera to establish an imaging plane in which a selected point on the native aortic valve appears on a central axis of the image of the native aortic valve;

after the advancing the delivery sheath, and while under the fluoroscopic imaging, and while the entire prosthetic aortic valve is in the position above the native aortic valve, rotating the delivery sheath about its long axis to align the selected radiopaque marker on the delivery sheath with the selected point on the native aortic valve in the imaging plane, thereby establishing a desired orientation of the prosthetic aortic valve with respect to the native aortic valve in which the prosthetic valve commissures are rotationally aligned with commissures of the native aortic valve;

after the rotating the delivery sheath, further advancing the delivery sheath along its long axis until the prosthetic aortic valve is disposed inside the native aortic valve; and deploying the prosthetic aortic valve into an implanted state inside the native aortic valve with the prosthetic aortic valve aligned in the desired orientation with respect to the native aortic valve and with the portion of the stent frame disposed adjacent to the location of conduction tissue of the native aortic valve so that the frame does not damage the conduction tissue.

2. The method of claim 1, wherein the rotating the delivery sheath is a second rotating, and further comprising, before the advancing the delivery sheath, initially rotating the delivery sheath towards the desired orientation to reduce the amount of rotation required during the second rotating.

3. The method of claim 1, further comprising, before the introducing, placing the prosthetic aortic valve mounted in the delivery sheath into an introducer sheath with the long axis of the delivery sheath in a rotational orientation relative to the introducer sheath that ensures the prosthetic aortic valve will be at least substantially aligned in the desired rotational orientation after the advancing.

4. The method of claim 1, wherein the prosthetic aortic valve includes a radiopaque marker.

5. The method of claim 4, wherein the rotating the delivery sheath includes aligning the selected radiopaque marker on the delivery sheath and the radiopaque marker on the prosthetic aortic valve.

6. The method of claim 1, wherein the selected point on the native aortic valve is one of a commissure, a cusp, a nadir of a cusp, or a coronary artery.

7. The method of claim 1, wherein the setting the position of the fluoroscopic camera incudes referencing a CT scan of the native aortic valve on which the selected point on the native aortic valve can be identified.

8. The method of claim 1, wherein the setting the position of the fluoroscopic camera incudes referencing a CT scan of the native aortic valve on which the selected point on the native aortic valve can be identified, identifying a fluoroscopic plane containing the selected point, and replicating the fluoroscopic plane for the fluoroscopic imaging.

9. The method of claim 1, wherein the portion includes a cut-out, recess, or opening.

10. The method of claim 1, further comprising, before the setting the position of the fluoroscopic camera:

predicting an initial position of the fluoroscopic camera that will establish the imaging plane based on a CT scan of the patient; and setting the initial position of the fluoroscopic camera.

11. The method of claim 10, further comprising, after the setting the initial position of the fluoroscopic camera and before the setting the position of the fluoroscopic camera, injecting a small puff of contrast dye into the native aortic valve.

* * * * *